United States Patent [19]

Sekine et al.

[11] Patent Number: 4,837,316
[45] Date of Patent: Jun. 6, 1989

[54] ALKYLAMIDE DERIVATIVES WITH H₂-RECEPTOR ANTAGONISTIC AND CYTOPROTECTIVE ACTION

[75] Inventors: Yasuo Sekine, Yokohama; Nobuhiro Hirakawa, Tokyo; Noriaki Kashiwaba, Kawasaki; Tetsuaki Yamaura, Niiza; Hisako Harada, Hino; Teruo Kutsuma, Inagi; Hajime Matsumoto; Akihiro Sekine, both of Hino; Yoshikazu Isowa, Tokyo, all of Japan

[73] Assignee: Fujirebio Kabushiki Kaisha, Tokyo, Japan

[21] Appl. No.: 900,752

[22] Filed: Aug. 27, 1986

[30] Foreign Application Priority Data

| Aug. 29, 1985 | [JP] | Japan | 60-190469 |
| Dec. 27, 1985 | [JP] | Japan | 60-292795 |
| Dec. 27, 1985 | [JP] | Japan | 60-292797 |
| Jan. 21, 1986 | [JP] | Japan | 61-008864 |
| Jan. 25, 1986 | [JP] | Japan | 61-013025 |
| Jan. 29, 1986 | [JP] | Japan | 61-015578 |
| Apr. 28, 1986 | [JP] | Japan | 61-096999 |

[51] Int. Cl.⁴ .................. C07D 405/12; A61K 31/33
[52] U.S. Cl. ................. 546/214; 540/596; 540/597; 540/602; 540/603; 540/610; 546/281; 546/337; 546/187; 546/194; 546/213; 546/233; 348/527; 348/517; 348/568; 348/179; 549/60; 549/77; 549/493; 564/179; 514/428
[58] Field of Search ......... 546/194, 187, 213, 198, 546/214, 233, 281, 337; 540/596, 597, 602, 603, 610; 548/527, 517, 568, 179; 549/60, 77, 493; 564/162

[56] References Cited

U.S. PATENT DOCUMENTS 4,588,734  5/1986  Suh et al. .................. 546/194
4,619,944 10/1986  Youssefyeh ................ 546/281

*Primary Examiner*—Robert T. Bond
*Attorney, Agent, or Firm*—Flynn, Thiel, Boutell & Tanis

[57] ABSTRACT

Alkylamide derivatives having the formula,

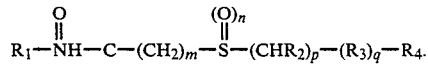

These compounds have a strong antiulcer action depend on histamine H₂-receptor antagonistic action and a cytoprotective action upon gastric mucous membrance.

11 Claims, No Drawings

ALKYLAMIDE DERIVATIVES WITH H₂-RECEPTOR ANTAGONISTIC AND CYTOPROTECTIVE ACTION

BACKGROUND OF THE INVENTION

1. Field of the Invention

This invention relates to novel alkylamide derivatives having $H_2$-receptor antagonistic and cytoprotective action.

2. Description of the Prior Art

The largest cause to form gastric ulcer and duodenal ulcer is said to be gastric hyperacid, and the compounds having antocholinergic action or neutralizing action against gastric juice were proposed as antiulcer drugs.

However, the compound having anticholinergic action is not preferable because of its strong side-effects. The compound having neutralizing action is also not suitable because of its short duration of medicinal effect.

It is also known that gastric juice is secreted by the stimulation of histamine $H_2$-receptor, some substituted phenoxypropylamide derivatives were reported to have histamine $H_2$-receptor antagonistic action and to inhibit gastric secretion (Japanese Patent KOKAI Nos. 53-149936, 55-130947, 56-7760, 56-8352, 56-115750, etc.). Besides, the amides having the following formula

in which Z represents N→O or C—NH—$Y_1$—$Y_2$ wherein $Y_1$ represents CO group or $SO_2$ group and $Y_2$ represents an alkyl group of $C_1$–$C_6$, phenyl group, pyridyl group, pyridyl-1-oxide group, pyradinyl group or thienyl group are also known to have histamine $H_2$-receptor antagonistic action (Japanese Patent KOKAI No. 58-208280).

SUMMARY OF THE INVENTION

It is an object of the invention to provide an antiulcer alkylamide derivative of which side-effects are not a problem.

It is another object of the invention to provide an antiulcer alkylamide derivative having a long duration.

It is still another object of the invention to provide an antiulcer alkylamide derivative of which histamine $H_2$-receptor antagonistic action is stronger than conventional compounds.

It is a further object of the invention to provide an antiulcer alkylamide derivative of which antiulcer effect is longer than conventional compounds.

It is a still further object of the invention to provide an antiulcer alkylamide derivative having cytoprotective effect upon gastric mucous membrane.

These objects can be achieved by the alkylamide derivatives having the formula,

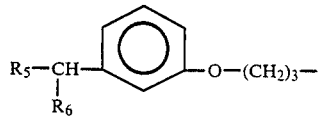

in which $R_1$ represents

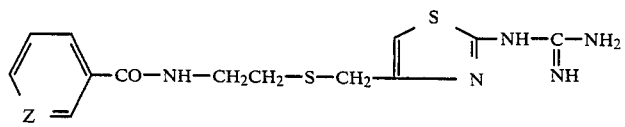

wherein $R_5$ represents piperidino group, 2-methylpiperidino group, 3-methylpiperidino group, 4-methylpiperidino group, dimethylamino group, 1-pyrrolidinyl group or 1-perhydroazepinyl group and $R_6$ represents hydrogen atom or methyl groups, $$R_7-(CH_2)_r-A-(CH_2)_s-$$

Wherein $R_7$ represents a thienyl group which is substituted with aminoalkyl group or aminoalkylene group, a furyl group which is substituted with aminoalkyl group, 2-guanidino group, a thiazolyl group which is substituted with aminoalkyl group, a oxazolyl group which is substituted with aminoalkyl group, pyridyl group, a pyridyl group which is substituted with aminoalkyl group, a imidazolyl group of which is substituted with alkyl group or dimethylpyrimidyl group, n represents 0 or 1, A represents oxygen atom or sulfur atom, s represents 2 or 3, or

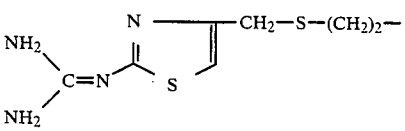

m represents 1, 2, 3, 4 or 5
n represents 0, 1 or 2
$R_2$ represents hydrogen atom, an alkyl group of which number of carbon atom is 1 to 3 or phenyl group
p represents 0 or 1
$R_3$ represents a saturated or unsaturated chain hydrocarbon residue of which number of carbon atom is 1 to 4
q represents 0 or 1
$R_4$ represents an alkyl group of which number of carbon atom is 1 to 4, thienyl group, pyridyl group, furyl group, naphthyl group, benzothiazolyl group, 2-aminothiadiazolyl group, styryl group, rinyl group, cyclohexyl group, phenyl group, a substituted phenyl group of which one hydrogen atom is substituted with an alkyl group or alkoxyl group of which number of carbon atom is 1 to 3, methoxycarbonyl group, carboxyl group, cyano group, benzothiazolyl group or a halogen atom, 2-pyrimidyl group, a substituted 2-pyrimidyl group of which one or two hydrogen atoms are substituted with methyl group, methoxycarbonylfuryl group, carboxylfuryl group, methylfuryl group, cyanofuryl group, piperidinomethylfuryl group, dimethylaminomethylfuryl group, a substituted pyridyl group of which one or two hydrogen atoms are substituted with alkyl group(s) of which number of carbon atom is 1 to 3, halogen atom(s), cyano group(s), alkoxy group(s), aminoalkyl group(s), nitro group(s), carbomethoxy group(s), carboxyl group(s) or acetoxy group(s), or a substituted thienyl group of which one hydrogen atom is substituted with an alkyl group of which number of carbon atom is 1 to 3, a halogen atom, methoxycarbonyl group, ethoxycarbonyl group or an amide group of which is 1 or 2.

DETAILED DESCRIPTION OF THE INVENTION

The aminoalkyl grops in $R_7$ group are all substituted methyl, propenyl groups of which one hydrogen atom is substituted with amino group, a substituted amino group of which one or two hydrogen atoms are substituted with methyl group(s) or ethyl group(s) or a cyclic amino group. The alkyl group(s) in the substituted imidazolyl group of $R_7$ are methyl group(s) or ethyl group(s).

The alkylamide derivatives of the invention may be divided into 6 groups.

The alkylamide derivatives of the first group are substituted phenoxypropylamide derivatives having the following general formula (I), q represents 0 or 1

$R_{41}$ represents an alkyl group of which number of carbon atom is 1 to 4, thienyl group, pyridyl group, furyl group, naphthyl group, benzothiazolyl group, 2-aminothiadiazolyl group, styryl group, rinyl group, cyclohexyl group, phenyl group, a substituted phenyl group of which one hydrogen atom is substituted with an alkyl group or alkoxyl group of which number of carbon atom is 1 to 3, methoxycarbonyl group, carboxyl group, cyano group, benzothiazolyl group or a halogen atom, 2-pyrimidyl group, a substituted 2-pyrimidyl group of which one or two hydrogen atoms are substituted with methyl group.

The alkyl group of $R_{21}$ is methyl group, ethyl group, n-propyl group or isopropyl group.

The chain hydrocarbon residue of $R_3$ is an alkylene group, an alkenylene group or an alkynylene group of each $C_1$ to $C_4$, and includes methylene group, ethylene group, trimethylene group, tetramethylene group, vinylene group, propenylene group, butenylene group, ethynylene group, propynylene group, butynylene group, propanedienylene group and butanedienylene.

The thienyl group of $R_{41}$ may be either 2-thienyl group or 3-thienyl group, and the pyridyl group may be 2-pyridyl group, 3-pyridyl group or 4-pyridyl group. The furyl group may be either 2-furyl group or 3-furyl group, and the naphthyl group may be either α-naphthyl group or β-naphthyl group. Bonding position of the substituent in the substituted phenyl group may be ortho, meta or para. Examples of the substituted phenyl group include methylphenyl group, ethylphenyl group,

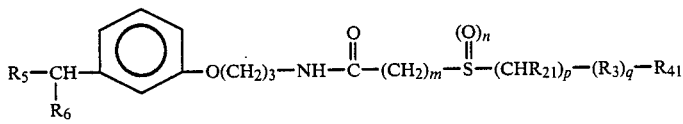

(I)

wherein
$R_5$ represents piperidino group, 2-methylpiperidino group, 3-methylpiperidino group, 4-methylpiperidino group, dimethylamino group, 1-pyrrolidinyl group or 1-perhydroazepinyl group and $R_6$ represents hydrogen atom or methyl group, m represents 1, 2, 3, 4, or 5
n represents 0, 1, or 2
$R_{21}$ represents hydrogen atom, an alkyl group of which number of carbon atom is 1 to 3 or phenyl group
p represents 0 or 1
$R_3$ represents a saturated or unsaturated chain hydrogen residue of which number of carbon atom is 1 to 4 propylphenyl group, methoxyphenyl group, ethoxyphenyl group, propoxyphenyl group, methoxycarbonylphenyl group, carboxyphenyl group, cyanophenyl group, chlorophenyl group and bromophenyl group. Bonding position(s) of methyl group(s) in the substituted 2-pyrimidyl group are not limited, and include 4-substitution, 5-substitution, 6-substitution, 4,6-substitution and 4,5-substitution. n, p and q may be 0, that is right half of the formula (I) includes the form of —$(CH_2)_m$—S—$R_{41}$.

The substituted phenoxypropylamide derivatives of the formula (I) are produced from the following compounds (III), (IV) and (V) through the following reactions.

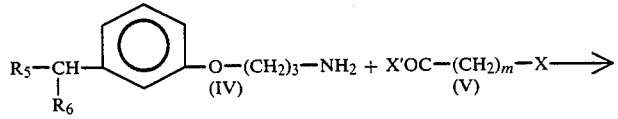

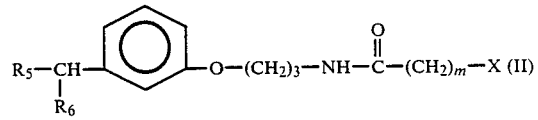

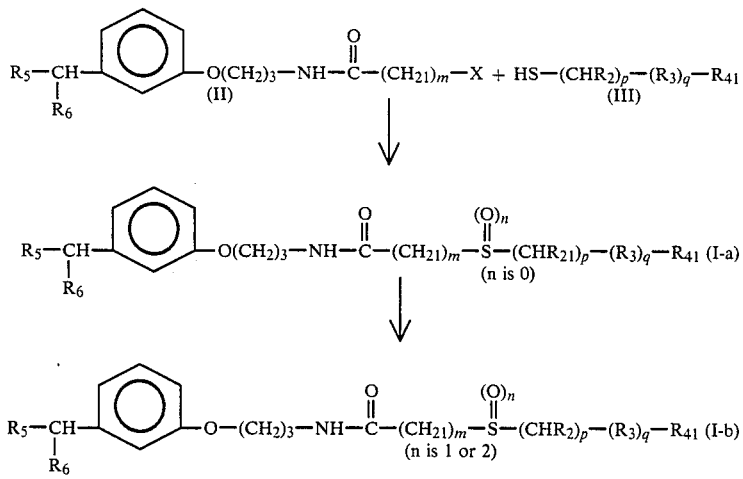

In the above formulas, X represents a halogen atom, and X' represents a halogen atom or hydroxyl group.

The amine derivatives of the formula (IV) may be prepared according to the method disclosed in Japanese Patent KOKAI No. 56-7760, etc.

The carboxylic acid derivatives of the formula (V) are commercially available or may be prepared according to a known method.

The reaction of the amine derivatives (IV) with the carboxylic acid derivatives (V) may be carried out according to an usual acylation, if necessary, in an inactive slovent such as described later.

In the case of using a carboxylic acid derivative of which X' is hydroxyl group, the reaction is carried out at 0° C. to 100° C. in the presence of a condensing agent such as 1,3-dicyclohexylcarbodiimide (DDC) or 1-ethyl-3-(3-dimethylaminopropyl) carbodiimide hydrochloride (EDC). On the other hand, in the case of using a carboxylic acid derivative of which X' is a halogen atom, the reaction is carried out in the presence of an inorganic base such as sodium hydroxide, potassium hydroxide, sodium carbonate or potassium carbonate or an organic base such as pyridine or triethylamine.

Separation of the amide compound (II) from the reaction mixture may be carried out by using a conventional manner such as liquid-liquid extraction, ion-exchange chromatography, column chromatography, thin-layer chromatography or recrystallization or a combination thereof.

Examples of the amino compound (II) are illustrated as follows;

N-[3-[3-(piperidinomethyl)phenoxy]propyl]-2-chloroacetamide
N-[3-[3-(piperidinomethyl)phenoxy]propyl]-3-chloropropylamide
N-[3-[3-(piperidinomethyl)phenoxy]propyl]-4-chlorobutylamide
N-[3-[3-(piperidinomethyl)phenoxy]propyl]-5-chloropentylamide
N-[3-[3-(piperidinomethyl)Phenoxy]Propyl]-6-bromohexlamide
N-[3-[3-(1-perhydroazepinylmethyl)phenoxy]propyl]-2-chloroacetamide
N-[3-[3-(1-perhydroazepinylmethyl)phenoxy]propyl]-4-chlorobutylamide
N-[3-[3-(1-perhydroazepinylmethyl)phenoxy]propyl]-6-bromohexylamide
N-[3-[3-[1-(1-piperidino)ethyl]phenoxy]propyl]-2-chloroacetamide
N-[3-[3-[1-(1-perhydroazepinyl)ethyl]phenoxy]propyl]-6-chlorohexylamide Condensation reaction of the compound (II) with the compound (III) to produce the compound (I) of the invention is preferably carried out in an inactive organic solvent such as halogenated hydrocarbons such as dichloromethane and chloroform, aromatic hydrocarbons such as benzene, toluene and xylene, ethers such as tetrahydrofuran and dioxane, amides such as dimethylformamide and dimethylacetamide, acetonitrile and dimethylsulfoxide. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes alkali hydrides and a combination of an alkali carbonate anhydrate and a halogenated alkali.

The reaction product from the compound (II) and the compound (III) is usually the compound (I-a) which is a thioether (n=0). The compound (I-b) which is a sulfinyl compound (n=1) or a sulfonyl compound (n=2) is produced by oxidation of the compound (I-a). The oxidation may be carried out according to an usual oxidation such as using an oxidizing agent in a suitable solvent. For example, the sulfinyl compound may be produced by using sodium metaperiodate in an aqueous alcohol, and the sulfonyl compound may be produced by using hydrogen peroxide in an organic acid.

The substituted phenoxypropylamide derivatives of the formula (I) are also produced from the following compounds (IV) and (VI) by condensation between them.

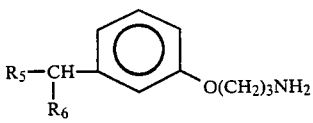 (IV)

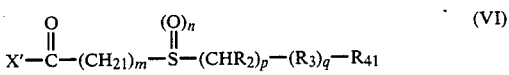 (VI)

The amine derivatives of the formula (IV) may be prepared according to the method disclosed in Japanese Patent KOKAI No. 56-7760, etc. as mentioned previously.

The compound of the formula (VI) is prepared as follows:

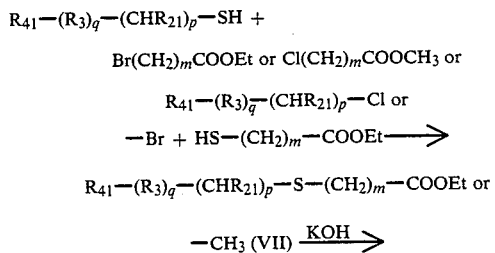

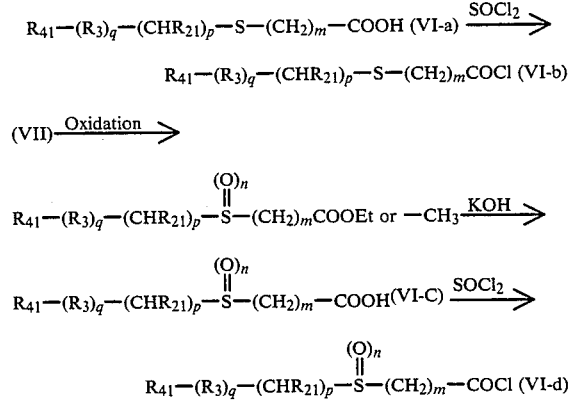

The compound (VI-c or d) which is a sulfinyl compound (n=1) or a sulfonyl compound (n=2) is produced by oxidation of the compound (VII) which is a thioether (n=0). The oxidation may be carried out according to an usual oxidation such as using an oxidizing agent in a suitable solvent. For example, the sulfinyl compound may be produced by using sodium metaperiodate in an aqueous alcohol, and the sulfonyl compound may be produced by using hydrogen peroxide in an organic acid.

Condensation reaction of the compound (IV) with the compound (VI-a) or (VI-c) to produce the compound (I) of the invention is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent such as DDC or EDC may preferably by added.

Condensation reaction of the compound (IV) with the compound (VI-b) or (VI-d) is preferably in the inactive organic solvent mentioned previously, water or a mixture thereof. Reaction temperature and reaction pressure are varied according to the raw compound etc., and usually, the reaction is carried out at 0° C. to the reflux temperature under ordinary pressure. The reaction is carried out in the presence of an inorganic base such as sodium hydroxide, potassium hydroxide, sodium carbonate or potassium carbonate or an organic solvent such as pyridine or triethylamine.

The substituted phenoxypropylamide derivatives (I) may be separated from the reaction mixture by using a conventional manner such as liquid-liquid extraction, ion-exchange chromatography, column chromatography, thin-layer chromatography or recrystallization or a combination thereof.

The alkylamide derivatives of the second group are substituted phenoxypropylamide derivatives having the follwing general formula (VIII)

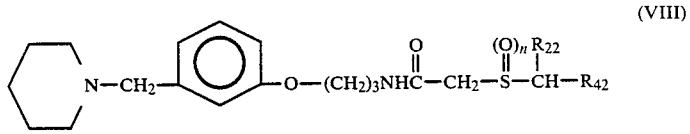 (VIII)

in which n represents 0, 1 or 2

$R_{22}$ represents hydrogen atom or an alkyl group of which number of carbon atom is 1 to 4

$R_{42}$ represents methoxycarbonylfuryl group, carboxylfuryl group, methylfuryl group, cyanofuryl group, piperidinomethylfuryl group, dimethylaminomethylfuryl group.

The alkyl group of $R_{22}$ includes methyl group, ethyl group, propyl group, isopropyl group and n-butyl group.

Every substituted furyl group of $R_{42}$ may be either 2-2-furyl or 3-furyl. Bonding position of each substituent is also not limited. Examples of the methoxycarbonylfuryl group include 2- or 3-(5-methoxycarbonyl)furyl group, 2- or 3-(4-methoxycarbonyl)furyl group, 2-(3-methoxycarbonyl)furyl group and 3-(2-methoxycarbonyl)furyl group. The carboxylfuryl group includes 2- or 3-(5-carboxy)furyl group, 2- or 3-(4-carboxy)furyl group, 2-(3-calboxy)furyl group and 3-(2-carboxy)furyl group, and the methylfuryl group includes 2- or 3-(5-methyl)furyl group, 2- or 3-(4-methyl)furyl group, 2-(3-methyl)furyl group and 3-(2-methyl)furyl group. The cyanofuryl group includes 2- or 3-(5-cyano)furyl group, 2- or 3-(4-cyano)furyl group, 2-(3-cyano)furyl group and 3-(2-cyano)furyl group, and the piperidinomethylfuryl group includes 2- or 3-(5-piperidinomethyl)furyl group, 2- or 3-(4-piperidinomethyl)furyl group, 2-(3-piperidinomethyl)furyl group and 3-(2-piperidinomethyl)furyl group. The dimethylaminomethylfuryl group includes 2- or 3-(5-dimethylaminomethyl)furyl group, 2- or 3-(4-dimethylaminomethyl)furyl group, 2-(3-dimethylaminomethyl)furyl group and 3-(2-dimethylaminomethyl)furyl group.

The substituted phenoxypropylamide derivatives (VIII) are produced from the following compounds (IX) and (X) through condensation between them.

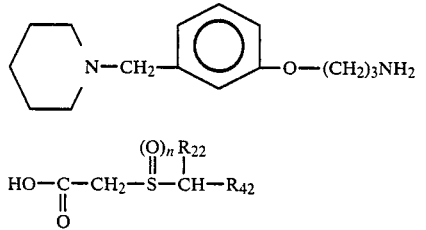
(IX)

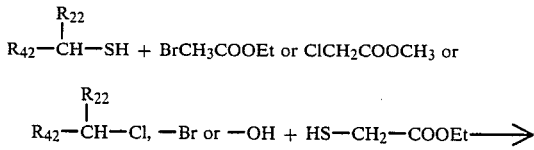
(X)

The amine derivatives of the formula (IV) may be prepared according to the method disclosed in Japanese Patent KOKAI No. 56-7760, etc.

The compound of the formula (X) is prepared as follows;

$$R_{42}-\overset{R_{22}}{\underset{|}{CH}}-SH + BrCH_3COOEt \text{ or } ClCH_2COOCH_3 \text{ or}$$

$$R_{42}-\overset{R_{22}}{\underset{|}{CH}}-Cl, -Br \text{ or } -OH + HS-CH_2-COOEt \longrightarrow$$

$$R_{42}-\overset{R_{22}}{\underset{|}{CH}}-S-CH_2COOEt \text{ or } -CH_3 \xrightarrow[\text{or}]{KOH}$$

$$R_{42}-\overset{R_{22}}{\underset{|}{CH}}-S-CH_2-COOH(X\text{-a}) \xrightarrow{\text{Oxidation}}$$

$$R_{42}-\overset{R_{22}}{\underset{|}{CH}}-\overset{(O)_n}{\underset{\|}{S}}-CH_2-COOEt \text{ or } -CH_3 \xrightarrow{KOH}$$

$$R_{42}-\overset{R_{22}}{\underset{|}{CH}}-\overset{(O)_n}{\underset{\|}{S}}-CH_2-COOH \text{ (X-b)}$$

The compound (X-b) which is a sulfinyl compound (n=1) or a sulfonyl compound (n=2) is produced by oxidation of the compound (X-a) which is a thioether (n=0). The oxidation may be carried out according to an usual oxidation such as using an oxidizing agent in a suitable solvent. For example, the sulfinyl compound may be produced by using sodium metaperiodate in an aqueous alcohol, and the sulfonyl compound may be produced by using hydrogen peroxide in an organic acid.

Condensation reaction of the compound (IX) with the compound (X) to produce the compound (VIII) of the invention is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent such as DCC or EDC may preferably be added.

The substituted phenoxypropylamide derivatives (VIII) are also produced from the following compounds

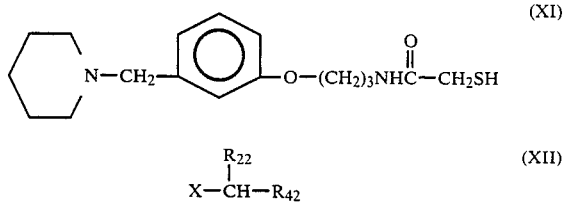
(XI)

$$\overset{R_{22}}{\underset{|}{X-CH-R_{42}}}$$
(XII)

The compound of the formula (XI) is prepared as follows;

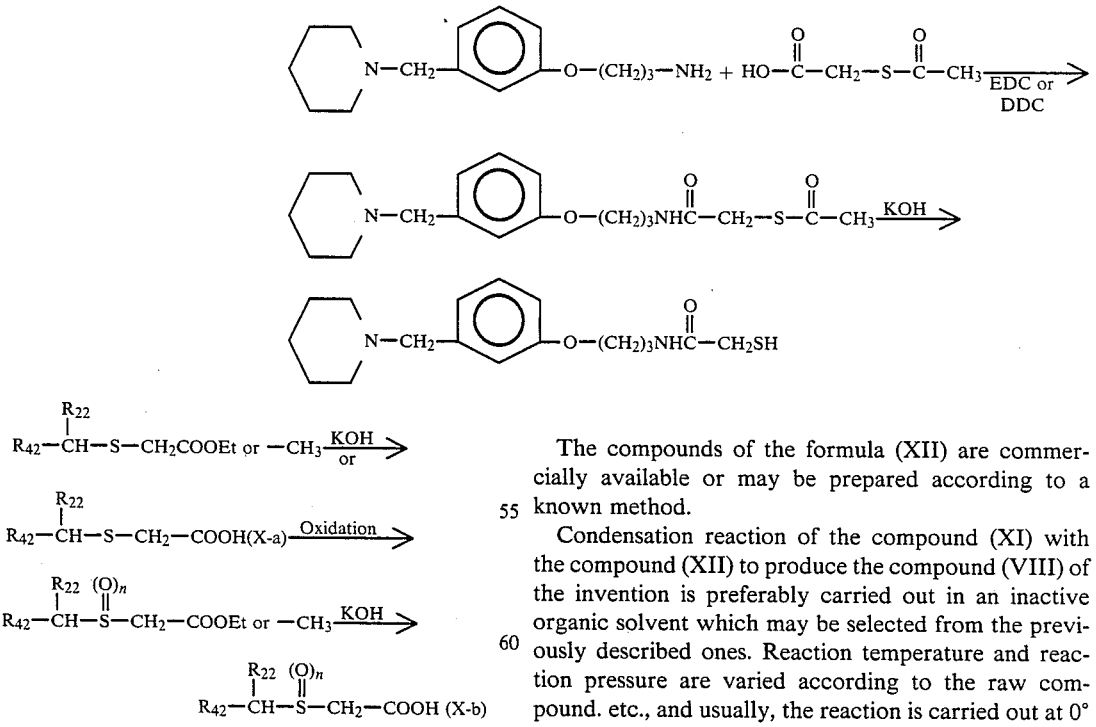

The compounds of the formula (XII) are commercially available or may be prepared according to a known method.

Condensation reaction of the compound (XI) with the compound (XII) to produce the compound (VIII) of the invention is preferably carried out in an inactive organic solvent which may be selected from the previously described ones. Reaction temperature and reaction pressure are varied according to the raw compound. etc., and usually, the reaction is carried out at 0° C. to the reflux temperature under ordinary pressure. A condensing agent may preferably be added. The condensing agent may be usual, and includes alkali hydrides and a combination of an alkali carbonate anhydrate and a halogenated alkali.

Separation of the substituted phenoxypropylamide derivatives (VIII) from the reaction mixture may be carried out by using a conventional manner such as liquid-liquid extraction, ion-exchange chromatography, column chromatography, thin-layer chromatography or recrystallization or a combination thereof.

The alkylamide derivatives of the third group are substituted phenoxypropylamide derivatives having the following general formula (XIII)

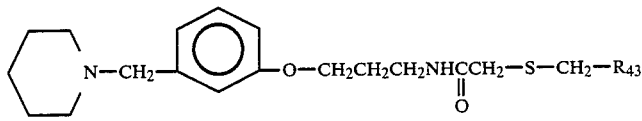
(XIII)

in which $R_{43}$ represents a pyridyl group of which one or two hydrogen atoms are substituted with alkyl group(s) of which number of carbon atom is 1 to 3, halogen atom(s), cyano group(s), alkoxy group(s), aminoalkyl group(s), nitro group(s), carbomethoxy group(s), carboxyl group(s) or acetoxy group(s).

The substituted pyridyl group may be 2-pyridyl, 3-pyridyl or 4-pyridyl. Bonding position(s) of the substituent(s) are also not limited. The alkyl group is methyl group, ethyl group, propyl group or isopropyl group. The halogen atom includes chlorine atom and bromine atom. Number of carbon atom in the alkoxyl group is 1 to 3, and examples are methoxy group, ethoxy group and propoxy group. The aminoalkyl group consists of an alkyl group having number of carbon atom of 1 or 2 and a secondary amino group bonded thereto, and includes dimethylaminomethyl group, diethylaminomethyl group, dimethylaminoethyl group, diethylaminoethyl group, piperidinomethyl group, piperidinoethyl group, pyrrolidinomethyl group and pyrrolidinoethyl group.

The substituted phenoxypropylamine derivatives (XIII) are produced from the following compounds (IX) and (XIV) through condensation between them.

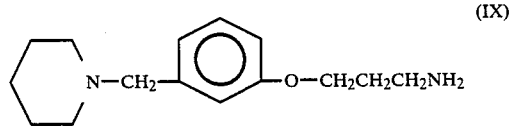
(IX)

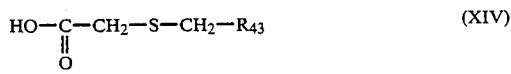
(XIV)

The compound (XIV) is prepared as follows;

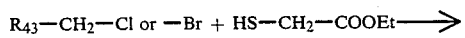

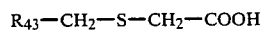

Condensation reaction of the compound (II) with the compound (III) to produce the compound (I) of the invention is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes DDC and EDC.

The substituted phenoxypropylamide derivatives (XIII) are also produced from the following compounds (XI) and (XV) through condensation between them.

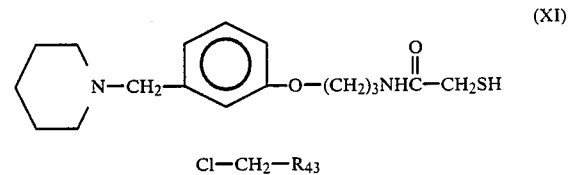
(XI)

$Cl-CH_2-R_{43}$

The compounds of the formula (XV) are commercially available or may be prepared according to a known method.

Condensation reaction of the compound (XI) with the compound (XV) is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes alkali hydrides and a combination of an alkali carbonate anhydrate and a halogenated alkali.

Separation of the substituted phenoxypropylamide derivatives (XIII) from the reaction mixture may be carried out by using a conventional manner such as liquid-liquid extraction, ion-exchange chromatography, column chromatography, thin-layer chromatography or recrystallization or a combination thereof.

The alkylamide derivatives of the fourth group are furylmethylthioacetamide derivatives having the following general formula (XVI)

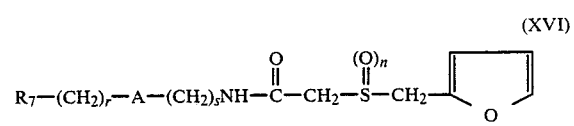
(XVI)

Wherein $R_7$ represents a thienyl group which is substituted with aminoalkyl group or aminoalkylene group, a furyl group which is substituted with aminoalkyl group, 2-guanidino group, a thiazolyl group which is substituted with aminoalkyl group, a oxazolyl group which is substituted with aminoalkyl group, pyridyl group, a pyridyl group which is substituted with aminoalkyl group, a imidazolyl group of which is substituted with alkyl group or dimethylpyrimidyl group, r represents 0 or 1, A represents oxygen atom or sulfur atom, s represents 2 or 3, and n represents 0, 1 or 2.

Every aminoalkyl group(s) in the above substituted groups consists of methyl group and an amino group bonded thereto. The amino group is primary, secondary or tertiary, and includes cyclic. Examples of the aminoalkyl group include monoaminomethyl group, dimethylaminomethyl group, diethylaminomethyl group, piperidinomethyl group, 2-methylpiperidino group, 3-methylpiperidino group, 4-methylpiperidino group, 1-pyrrolidinylmethyl group and 1-perhydroazepinylmethyl group. When two or more aminoalkyl groups are bonded, they may be identical with or different from each other. The aminoalkylene group(s) in the substituted thienyl group consists of propenyl group and an amino group bonded thereto. The amino group is primary, secondary or tertiary, and includes cyclic. Examples of the aminoalkylene group include 3-(1-pyrrolidinyl)-1-propenyl group, 3piperidino-1-propenyl group, 3-dimethylamino-1propenyl group, 3-diethylamino-1-propenyl group, and 3-(1-perhydroazepinyl)-1-propenyl group. The alkyl group in the substituted imidazolyl group is methyl group or ethyl group. Bonding position(s) of the above groups is not limited.

The thienyl group in the substituted thienyl group may be either 2-thienyl or 3-thienyl, and the furyl group may also be either 2-furyl or 3-furyl. The thiazolyl group may be 2-thiazolyl, 4-thiazolyl or 5-thiazolyl, and the oxazolyl group may be 2-oxazolyl, 4-oxazolyl or 5-oxazolyl.

The pyridyl group may be 2-pyridyl, 3-pyridyl or 4-pyridyl. Examples of the substituted pyridyl group are 4-piperidinomethyl-2-pyridyl group, 4-dimethylaminomethyl-2-pyridyl group, 4-diethylaminomethyl-2-pyridyl group, 4-(1-pyrrolidinylmethyl)-2-pyridyl group, 4-(1-perhydroazepinylmethyl)-2-pyridyl group, 5-piperidinomethyl-3-pyridyl group, 5-dimethylaminomethyl-3-pyridyl group, 5-diethylaminomethyl-3-pyridyl group, 4-(1-pyrrolidinylmethyl)-3pyridyl group, 4-(1-perhydroazepinylmethyl)-3-pyridyl group, 2-piperidinomethyl-4-pyridyl group, 2-dimethylaminomethyl-4-pyridyl group, 2-dimethylaminomethyl-4-pyridyl group, 4-(1-pyrrolidinylmethyl)-4-pyridyl group and 4(1-perhydroazepinylmethyl)-4-pyridyl group.

The imidazolyl group in the substituted imidazolyl group is 5-imidazolyl. Examples of the substituted imidazolyl group are 4-methyl-5-imidazolyl group and 4-ethyl-5-imidazolyl group.

The pyrimidyl group may be 2-pyrimidyl, 4-pyrimidyl or 5-pyrimidyl, and examples are 4, 6-dimethyl-2-pyrimidyl group, 2, 6-dimethyl-4-pyrimidyl group and 2, 4-dimethyl-5-pyrimidyl group.

The furylmethylthioacetamide derivatives (XVI) are produced from the following compounds (XVII-1) or (XVII-2) and (XVIII) through condensation between them.

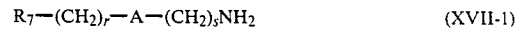

$R_7-(CH_2)_r-A-(CH_2)_sNH_2$ (XVII-1)

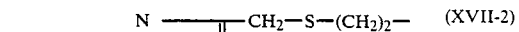

(XVII-2)

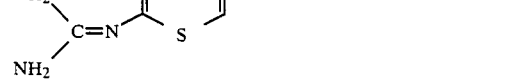

(XVIII)

The compounds (XVII-1) may be produced according to the method disclosed in Japanese Patent KOKAI Nos. 54-115385, 56-119685, 55-10591, 57-91980, 57-91986, 58-170779, 49-102668 or 53-147069 or Tetrabedron Letters, vol. 24, No. 22, pp 2287–2290(1983)

The compounds (XVIII) are commercially available or may be prepared according to a known method.

Condensation reaction of the compound (XVII-1) or (XVII-2) with the compound (XVIII) is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes DCC and EDC.

Separation of the furylmethylthioacetamide derivatives (XVI) from the reaction mixture may be carried out by using a conventional manner such as liquid-liquid extraction, ion-exchange chromatography, column chromatogrphy, thin-layer chromatography or recrystallization or a combination thereof.

The alkylamide derivatives of the fifth group are 2-guanidinothiazole derivatives having the following general formula (XIX)

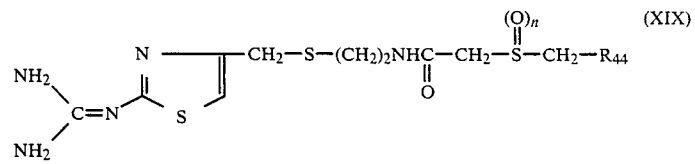

in which $R_{44}$ represents phenyl group, furyl group, thienyl group, pyridyl group, naphthyl group or cyclohexyl group, and n represents 0, 1 or 2.

The furyl group may be 2-furyl or 3-furyl, and the thienyl group may be 2-thienyl or 3-thienyl. The pyridyl group may be 2-pyridyl, 3-pyridyl or 4-pyridyl, and the naphthyl group may be α-naphthyl or β-naphthyl.

The 2-guanidinothiazole derivatives (XIX) are produced from the following compounds (XX) and (XXI) through condensation between them.

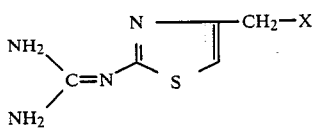  (XX)

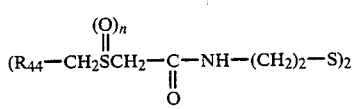  (XXI)

The compound (XX) may be produced according to the method disclosed in Japanese Patent KOKAI No. 53-147069.

The compounds (XXI) may be produced by the following synthesis A or B.

Synthesis A

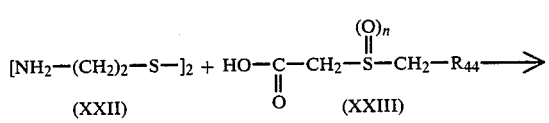

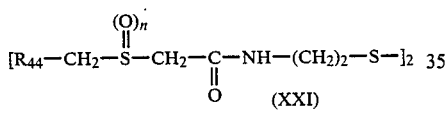

Condensation reaction of the compound (XXII) with the compound (XXIII) is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes DDC and EDC.

Synthesis B

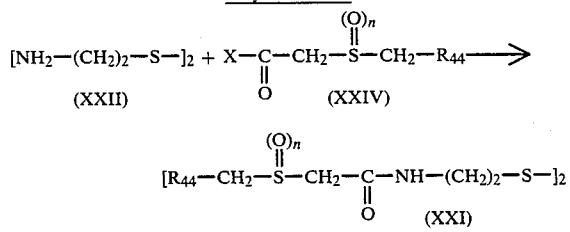

Condensation reaction of the compound (XXII) with the compound (XXIV) is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. The reaction is carried out in the presence of an inorganic base or an organic base such as illustrated previously.

Condensation reaction of the compound (XX) with the compound (XXI) is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes DDC and EDC.

Separation of the 2-guanidinothiazole derivatives (XIX) from the reaction mixture may be carried out by using a conventional manner such as liquid-liquid extraction, ion-exchange chromatography, column chromatography, thin-layer chromatography or recrystallization or a combination thereof.

The alkylamide derivatives of the sixth group are substituted phenoxypropylamide derivatives having the following general formula (XXV)

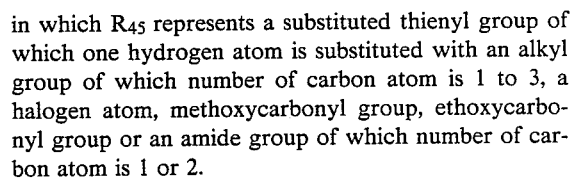  (XXV)

in which $R_{45}$ represents a substituted thienyl group of which one hydrogen atom is substituted with an alkyl group of which number of carbon atom is 1 to 3, a halogen atom, methoxycarbonyl group, ethoxycarbonyl group or an amide group of which number of carbon atom is 1 or 2.

The thienyl group may be 2-thienyl or 3-thienyl, and bonding position of the substituent may be any of the remaining positions.

The substituted phenoxypropylamide derivatives (XXV) are produced from the following compounds (IX) and (XXVI) through condensation between them.

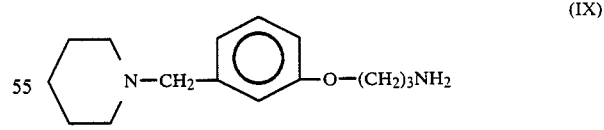  (IX)

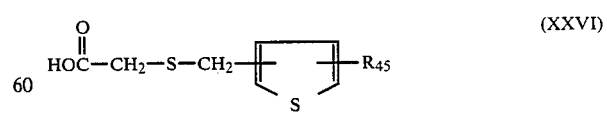  (XXVI)

The compound (XXVI) is prepared as follows

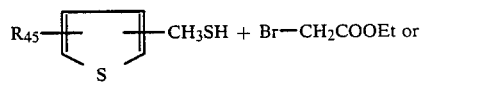  CH$_3$SH + Br—CH$_2$COOEt or

Cl—CH$_2$—COOCH$_3$

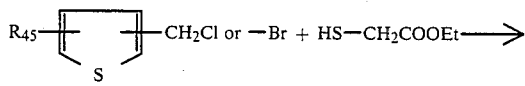

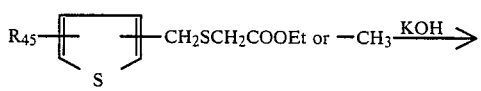

Condensation reaction of the compound (IX) with the compound (XXVI) is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes DDC and EDC.

The substituted phenoxypropylamide derivatives (XXV) are also produced from the following compounds

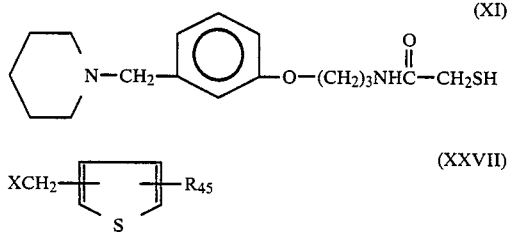

The compounds (XXVII) are commercially available or may be prepared according to a known method.

Condensation reaction of the compound (XI) with the compound (XXVII) is preferably carried out in an inactive organic solvent which may be selected from the previously described ones. Reaction temperature and reaction pressure are varied according to the raw compound etc., and usually, the reaction is carried out at 0° C. to the reflux temperature under ordinary pressure. A condensing agent may preferably be added. The condensing agent may be usual, and includes alkali hydrides and a combination of an alkali carbonate anhydrate and a halogenated alkali.

Separation of the substituted phenoxypropylamide derivatives (XXV) from the reaction mixture may be carried out by using a conventional manner such as liquid-liquid extraction, ion-exchange chromatography, column chromatography, thin-layer chromatography or recrystallization or a combination thereof.

Among various forgoing alkylamide derivatives of the invention, the following compounds (XXVIII) are superior in $H_2$-receptor antagonistic action and cytoprotective action.

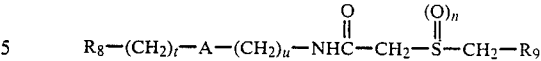

in which
$R_8$ represents

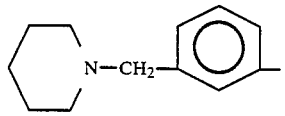

$t$ represents 0
$A$ represents $O$
$u$ represents 3
$n$ represents 0, 1 or 2
$R_9$ represents phenyl group, furyl group, pyridyl group or thienyl group. The furyl group may be 2-furyl or 3-furyl, and the pyridyl group may be 2-pyridyl, 3-pyridyl or 4-pyridyl. The thienyl group may also be 2-thienyl or 3-thienyl.

or in which
$R_8$ represents

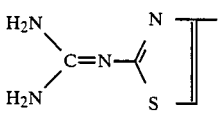

$t$ represents 1
$A$ represents $S$
$u$ represents 2
$n$ represents 0, 1 or 2
$R_9$ represents phenyl group, furyl group or pyridyl group. The furyl group may be 2-furyl or 3-furyl, and the pyridyl group may be 2-pyridyl, 3-pyridyl or 4-pyridyl.

Any alkylamide derivative of the invention may be used as an acid adduct salt. Such an acid includes inorganic acids such as hydrochloric acid, hydrobromic acid, phosphoric acid, sulfuric acid and nitric acid and organic acids such as acetic acid, propionic acid, lactic acid, citric acid, oxalic acid and maleic acid. The acid adduct salts may be prepared according to an known method.

The alkylamide derivatives of the invention have superior histamine $H_2$-receptor antagonistic action and an inhibitory action against gastric secretion due to this antagonistic action. The alkylamide derivatives have also protective action upon gastric mucous membrane, and they may be usable as antiulcer drogs. Administration forms may be tablet, capsule, solution or suppository. The productions of the alkylamide derivatives are easy, and they may be produced in a high yield by the foregoing methods. These methods are also suitable for masu-protection.

EXAMPLES
Examples of Production
Example 1

1.0 g of N-[3-{3-(piperidinomethyl)phenoxy}-propyl]-2-chloroacetamide was dissolved in 20 ml of acetonitrile, and 0.46 g (0.43 ml, 3.7 mmol.) of α-toluenethiol, 0.51 g of anhydrous potassium carbonate and 0.061 g of potassium iodide were added to the solution. The above solution was refluxed for 4 hours, and then cooled. 50 ml of water was added, and extraction was carried out by using 50 ml of dichloromethane. The dichloromethane layer was dried over anhydrous magnesium sulfate, and thereafter the solvent was evaporated. The residue was purified by silica gel column chromatography using methanol:dichloromethane=1.19 as developing solvent, and 0.68 g of the following oily compound was obtained.

Structure and properties of this compound are as follows:

Compound 1
N-[3-{3-(piperidinomethyl)phenoxy}propyl]-2-(benzylthio)acetamide

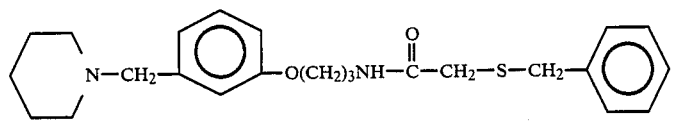

NMR (CDCl$_3$, δ) 1.40–1.65(6H, m), 1.96(2H, tt, J=6 Hz, 6 Hz), 2.30–2.50(4H, m), 3.16(2H, s), 3.40(2H, t, J=6 Hz), 3.45(2H, s), 3.70(2H, s), 4.04(2H, t, J=6 Hz), 6.80–7.35(10H, m).

IR (cm$^{-1}$, film, ν) 1650 (C=O).

High Resolution Mass Spectrum Molecular Weight: Calcd. for C$_{24}$H$_{32}$N$_2$O$_2$S 412.2184. Found 412.2162.

Examples 2–29

Various compounds were produced in the same method as Example 1 where each 3.7 mmole of the following thiols was employed instead of (1) α-toluenethiol 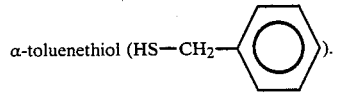

(2) Benzenethiol 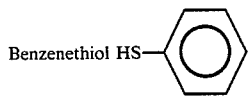

(3) 4-Pyridinethiol 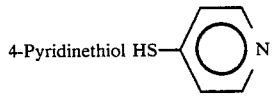

(4) 2-Benzothiazolthiol 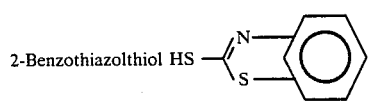

(5) 2-Naphthalenethiol 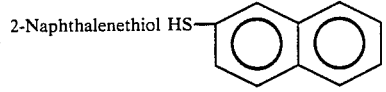

(6) Cyclohexanethiol 

(7) 4-Methoxybenzenethiol 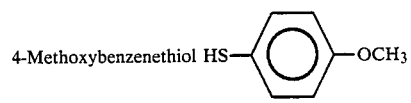

(8) 3-Methylbenzenethiol 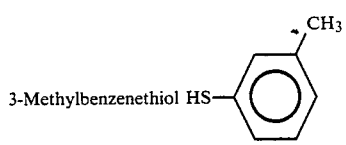

(9) 4,6-Dimethyl-2-pyrimidinethiol 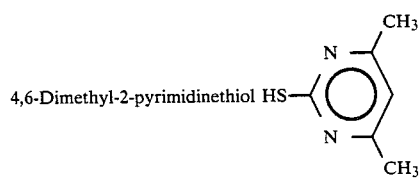

(10) 4-Chlorobenzenethiol 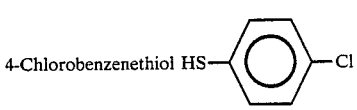

(11) 2-Methoxybenzenethiol 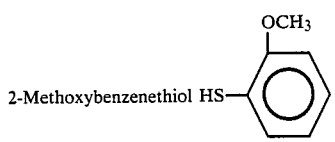

(12) 4-Methoxyphenylmethanethiol 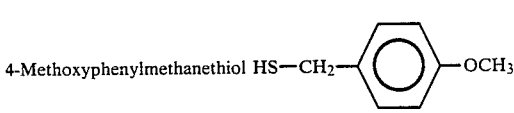

(13) Diphenylmethanethiol 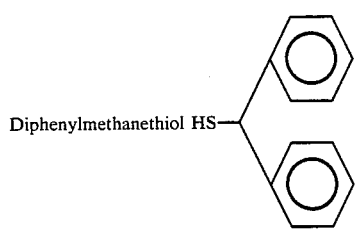

(14) 3-Phenylpropane-1-thiol 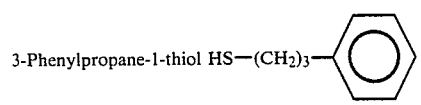

-continued

3-Phenyl-2-propene-1-thiol 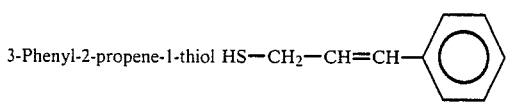 (15)

Cyclohexylmethanethiol 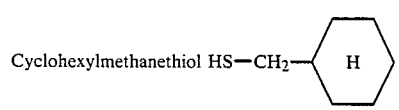 (16)

1-Phenylethane-1-thiol 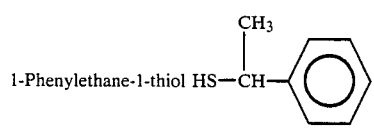 (17)

5-Amino-1,3,4-thiadiazole-2-thiol 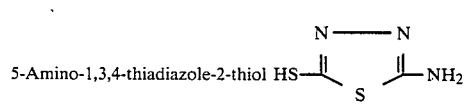 (18)

2-Furylmethanethiol 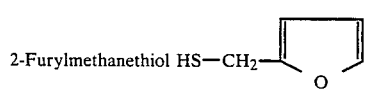 (19)

2-Thienylmethanethiol 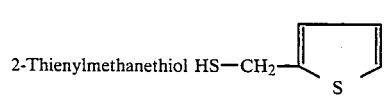 (20)

2-Naphthylmethanethiol 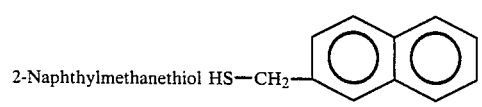 (21)

2-Propene-1-thiol HS—CH$_2$—CH=CH$_2$ (22)

4-Cyanophenylmethanethiol 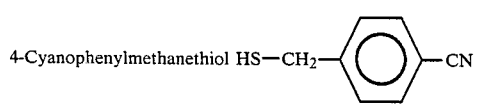 (23)

4-Methoxycarbonylphenylmethanethiol (24)
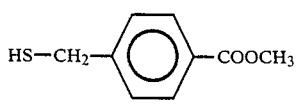

5-Phenylpentane-1-thiol 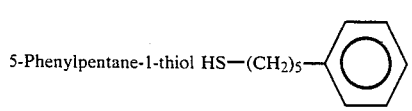 (25)

-continued

4-Chlorophenylmethanethiol  (26)

4-Methylphenylmethanethiol 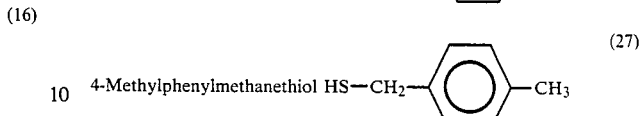 (27)

4-Pyridylmethanethiol 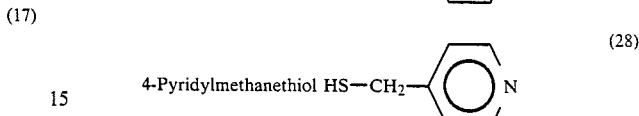 (28)

2-Benzothiazolylmethanethiol 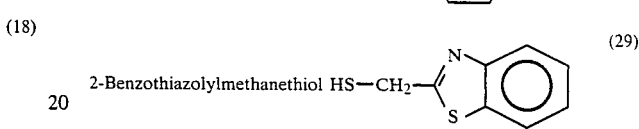 (29)

Structures and properties of the compound obtained are as follows:

Compound 2

N-[3-{3-(piperidinomethyl)phenoxy}propyl]-2-(phenylthio)acetamide

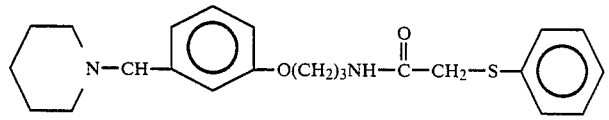

NMR (CDCl$_3$, δ) 1.20–1.77(6H, m), 1.90(2H, tt, J=6 Hz, 6 Hz), 2.23–2.58(4H, m), 3.40(2H, t, J=6 Hz), 3.44(2H, s), 3.46(1H, brs), 3.64(2H, s), 3.90(2H, t, J=6 Hz), 7.21(5H, s), 6.57–7.38(4H, m).

IR (cm$^{-1}$, film, ν) 1650 (C=O).

High Resolution Mass Spectrum Molecular Weight: Calcd. for C$_{23}$H$_{30}$N$_2$O$_2$S 398.2027. Found 398.2024.

Compound 3

N-[3-{3-(piperidinomethyl)phenoxy}propyl]-2-(4-pyridylthio)acetamide

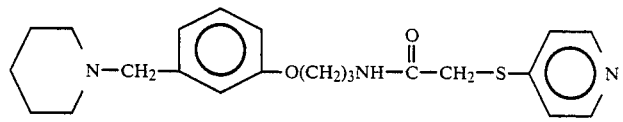

NMR (CDCl$_3$, δ) 1.30–1.70(6H, m), 1.89(2H, tt, J=6 Hz, 6 Hz), 2.20–2.50(4H, m), 3.39(2H, t, J=6 Hz), 3.40(2H, s), 3.63(2H, s), 3.90(2H, t, J=6 Hz), 6.50–7.40(7H, m), 8.20–8.40(2H, m).

IR (cm$^{-1}$, film, ν) 1640 (C=O).

High Resolution Mass Spectrum Molecular Weight: Calcd. for C$_{22}$H$_{29}$N$_3$O$_2$S 399.1980. Found 399.1947.

Compound 4
N-[3-{3-(piperidinomethyl)phenoxy}propyl]-2-(2-benzothiazolylthio)acetamide

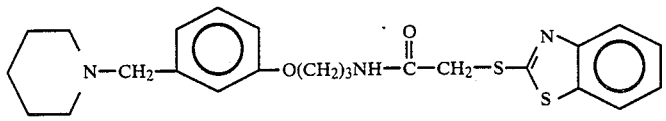

NMR (CDCl₃, δ) 1.30–1.70(6H, m), 1.93(2H, tt, J=6 Hz, 6 Hz), 2.20–2.50(4H, m), 3.41(2H, t, J=6 Hz), 3.41(2H, s), 3.94(2H, t, J=6 Hz), 3.95(2H, s), 6.47–7.84(8H, m), 6.80(1H, brs).
IR (cm⁻¹, film, ν) 1655 (C=O).
High Resolution Mass Spectrum Molecular Weight: Calcd. for C₂₄H₂₉N₃O₂S 455.1701. Found 455.1669.

Compound 5
N-[3-{3-(piperidinomethyl)phenoxy}propyl]-2-(2-naphthylthio)acetamide

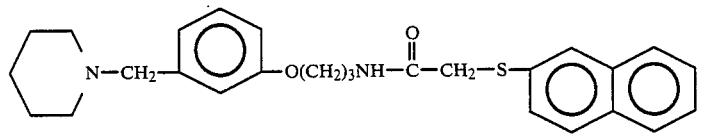

NMR (CDCl₃, δ) 1.30–1.60(6H, m), 1.85(2H, tt, J=6 Hz, 6Hz), 2.20–2.50(4H, m), 3.39(2H, s), 3.48(2H, t, J=6 Hz), 3.70(2H, s), 3.81(2H, t, J=6 Hz), 6.50–7.90(12H, m).
IR (cm⁻¹, film, ν) 1650 (C=O).
High Resolution Mass Spectrum Molecular Weight: Calcd. for C₂₇H₃₂N₂O₃S 448.2184. Found 448.2100.

Compound 6
N-[3-{3-(piperidinomethyl)phenoxy}propyl]-2-(cyclohexylthio)actamide

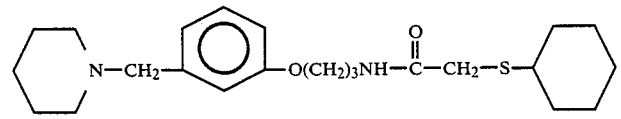

NMR (CDCl₃, δ) 1.05–2.60(23H, m), 3.20(2H, s), 3.41(2H, s), 3.52(2H, t, J=6 Hz), 4.01(2H, t, J=6 Hz), 6.60–7.50 (5H, m).

IR (cm⁻¹, film, ν) 1650 (C=O).
High Resolution Mass Spectrum Molecular Weight: Calcd. for C₂₃H₃₆N₂O₂S 404.2496. Found 404.2479.

Compound 7
N-[3-{3-(piperidinomethyl)phenoxy}propyl]-2-(3-methoxyphenylthio)acetamide

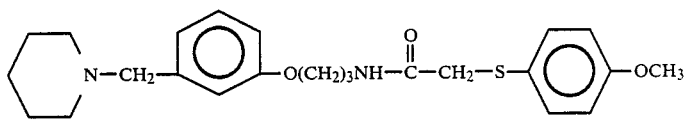

NMR (CDCl₃, δ) 1.30–1.70(6H, m), 1.90(2H, tt, J=6 Hz, 6 Hz), 2.20–2.50(4H, m), 3.33(2H, t, J=6 Hz), 3.37(2H, s), 3.46(2H, s), 3.67(3H, s), 3.89(2H, t, J=6 Hz), 6.50–7.30(9H, m).
IR (cm⁻¹, film, ν) 1650 (C=O).
High Resolution Mass Spectrum Molecular Weight: Calcd. for C₂₄H₃₂N₂O₃S 428.2133. Found 428.2107.

Compound 8
N-[3-{3-(piperidinomethyl)phenoxy}propyl]-2-(3-methylphenylthio)acetamide

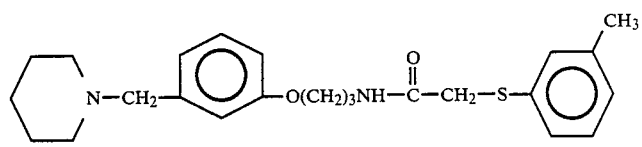

NMR (CDCl₃, δ) 1.30–1.70(6H, m), 1.89(2H, tt, J=6 Hz, 6 Hz), 2.24(3H, s), 2.20–2.50(4H, m), 3.36(2H, t, J=6 Hz), 3.38(2H, s), 3.58(2H, s), 3.87(2H, t, J=6 Hz), 6.50–7.40(9H, m).
IR (cm⁻¹, film, ν) 1650 (C=O).
High Resolution Mass Spectrum Molecular Weight: Calcd. for C₂₄H₃₂N₂O₂S 412.2184. Found 412.2153.

Compound 9

N-[3-{3-(piperidinomethyl)phenoxy}propyl]-2-{2-(4,6-dimethylpyrimidyl)thio}acetamide

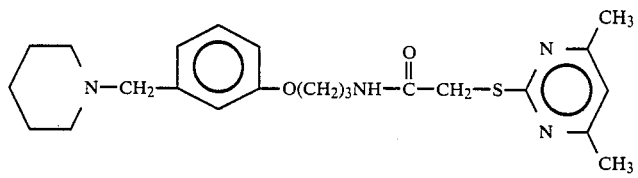

NMR (CDCl₃, δ) 1.30–1.70(6H, m), 1.92(2H, tt, J=6 Hz, 6 Hz), 2.20–2.50(4H, m), 2.32(6H, s), 3.38(2H, t, J=6 Hz), 3.39(2H, s), 3.75(2H, s), 3.85(2H, t, J=6 Hz), 6.50–7.50(5H, m).

IR (cm⁻¹, film, ν) 1660 (C=O).

High Resolution Mass Spectrum Molecular Weight: Calcd. for $C_{23}H_{32}N_4O_2S$ 428.2245. Found 428.2207.

Compound 10

N-[3-{3-(piperidinomethyl)phenoxy}propyl]-2-(4-chlorophenylthio)acetamide

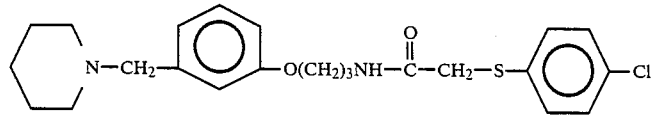

NMR (CDCl₃, δ) 1.30–1.70(6H, m), 1.90(2H, tt, J=6 Hz, 6 Hz), 2.20–2.50(4H, m), 3.38(2H, t, J=6 Hz), 3.38(2H, s), 3.55(2H, s), 3.89(2H, t, J=6 Hz), 6.50–7.30(9H, m).

IR (cm⁻¹, film, ν) 1650 (C=O).

High Resolution Mass Spectrum Molecular Weight: Calcd. for $C_{23}H_{29}N_2O_2ClS$ 432.1637. Found 432.1614.

Compound 11

N-[3-{3-(piperidinomethyl)phenoxy}propyl]-2-(2-methoxyphenylthio)acetamide

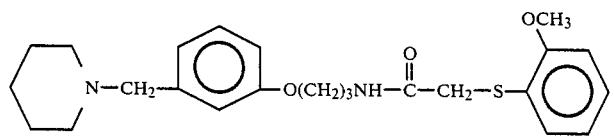

NMR (CDCl₃, δ) 1.30–1.70(6H, m), 1.89(2H, tt, J=6 Hz, 6 Hz), 2.20–2.50(4H, m), 3.35(2H, t, J=6 Hz), 3.40(2H, s), 3.55(2H, s), 3.80(3H, s), 3.83(2H, t, J=6 Hz), 6.50–7.40(9H, m).

IR (cm⁻¹, film, ν) 1655 (C=O).

High Resolution Mass Spectrum Molecular Weight: Calcd. for $C_{24}H_{32}N_2O_3S$ 428.2132. Found 428.2051.

Compound 12

N-[3-{3-(piperidinomethyl)phenoxy}propyl]-2-(4-methoxybenzylthio)acetamide

NMR (CDCl₃, δ) 1.40–1.50(2H, m), 1.50–1.65(4H, m), 1.97(2H, tt, J=6 Hz, 6 Hz), 2.35–2.50(4H, m), 3.14(2H, s), 3.44(2H, t, J=6 Hz), 3.46(2H, s), 3.66(2H, s), 3.78(3H, s), 4.05(2H, t, J=6), 6.81(2H, d, J=8.8 Hz), 6.80–7.00(2H, m), 7.15(2H, d, J=8.8 Hz), 7.10–7.30(2H, m).

IR (cm⁻¹, film, ν) 1650 (C=O).

High Resolution Mass Spectrum Molecular Weight: Calcd. for $C_{24}H_{34}N_2O_3S$ 442.2290. Found 442.2256.

Compound 13

N-[3-{3-(piperidinomethyl)phenoxy}propyl-2-(diphenylmethylthio)acetamide

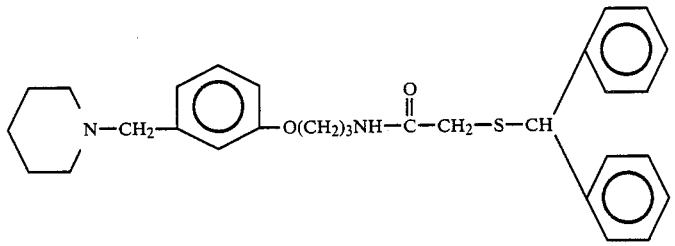

NMR (CDCl₃, δ) 1.20–1.70(6H, m), 1.92(2H, tt, J=6 Hz, 6 Hz), 2.10–2.50(4H, m), 3.08(2H, s), 3.32(2H, t, J=6 Hz), 3.48(2H, s), 3.98(2H, t, J=6 Hz), 5.12(1H, s), 6.50–7.50(15H, m).

IR (cm⁻¹, film, ν) 1650 (C=O).

High Resolution Mass Spectrum Molecular Weight: Calcd. for $C_{30}H_{36}N_2O_2S$ 488.2496. Found 488.2432.

Compound 14

N-[3-{3-(piperidinomethyl)phenoxy}propyl]-2-(3-phenylpropyl-1-thio)acetamide

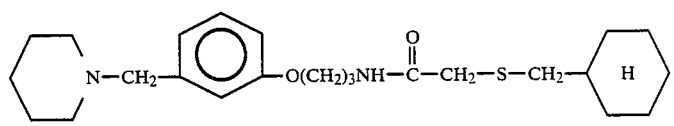

NMR (CDCl₃, δ) 1.20–2.80(18H, m), 3.15(2H, s), 3.38(2H, s), 3.38(2H, t, J=6 Hz), 3.98(2H, t, J=6 Hz), 6.60–7.40(10H, m).

IR (cm⁻¹, film, ν) 1650 (C=O).

High Resolution Mass Spectrum Molecular Weight: Calcd. for $C_{26}H_{36}N_2O_2S$ 440.2497. Found 440.2475.

Compound 15

N-[3-{3-(piperidinomethyl)phenoxy}propyl]-2-(3-phenyl-2-propenyl-1-thio)acetamide

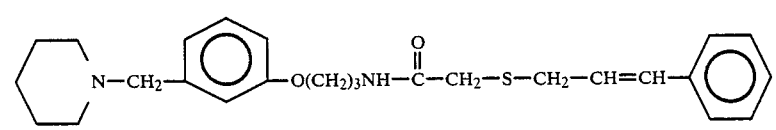

NMR (CDCl₃, δ) 1.30–1.70(6H, m), 1.82(2H, tt, J=6 Hz, 6 Hz), 2.20–2.50(4H, m), 3.20–3.50(4H, m), 3.40(2H, s), 3.92(2H, t, J=6 Hz), 5.80–7.40(12H, m).

IR (cm⁻¹, film, ν) 1650 (C=O).

High Resolution Mass Spectrum Molecular Weight: Calcd. for $C_{26}H_{34}H_2O_2S$ 438.2341. Found 438.2358.

Compound 16

N-[3-{3-(piperidinomethyl)phenoxy}propyl]-2-(cyclohexylmethylthio)acetamide

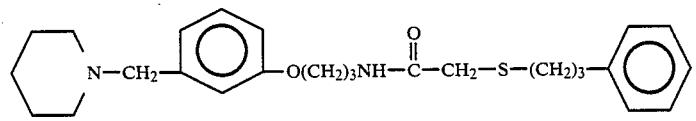

NMR (CDCl₃, δ) 0.80–1.90(19H, m), 2.03(2H, tt, J=6 Hz, 6 Hz), 2.30–2.50(4H, m), 2.39(2H, d, J=7 Hz), 3.27(2H, s), 3.48(2H, s), 3.53(2H, t, J=6 Hz), 4.08(2H, t, J=6 Hz), 6.80–7.30(4H, m), 7.35–7.45(1H, brs).

IR (cm⁻¹, film, ν) 1650 (C=O).

High Resolution Mass Spectrum Molecular Weight: Calcd. for $C_{24}H_{38}N_2O_2S$ 418.2654. Found 418.2672.

Compound 17

N-[3-{3-(piperidinomethyl)phenoxy}propyl]-2-(1-phenylethyl-1-thio)acetamide

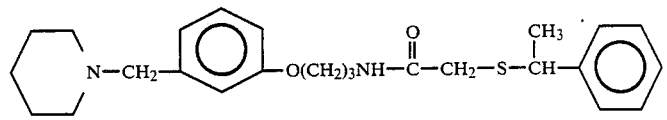

NMR (CDCl₃, δ) 1.20–1.80(8H, m), 1.90(2H, tt, J=6 Hz, 6 Hz), 2.20–2.55(4H, m), 3.03(2H, s), 3.40(2H, t, J=6 Hz), 3.43(2H, s), 3.75–4.15(3H, m), 6.65–7.40(10H, m).

IR (cm$^{-1}$, film, $\nu$) 1650 (C=O).
High Resolution Mass Spectrum Molecular Weight:
Calcd. for $C_{25}H_{34}N_2O_2S$ 426.2340. Found 426.2333.

Compound 18

N-[3-{3-(piperidinomethyl)phenoxy}propyl]-2-(5-amino-1,3,4-thiadiazolylthio)acetamide

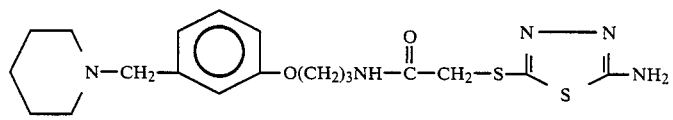

NMR (CDCl$_3$, $\delta$) 1.40–1.80(7H, m), 1.96(2H, tt, J=6.4 Hz, 6.4 Hz), 2.23–2.64(4H, m), 3.45(2H, s), 3.47(2H, t, J=6.4 Hz), 3.78(2H, t, J=6.4 Hz), 3.80(2H, s), 5.86(2H, s), 6.74–7.34(4H, m).

IR (cm$^{-1}$, film, $\nu$), 1660 (C=O).
High Resolution Mass Spectrum Molecular Weight:
Calcd. for $C_{19}H_{27}N_5O_2S_2$ 421.1606. Found 421.1646.

Compound 19

N-[3-{3-(piperidinomethyl)phenoxy}propyl]-2-(furfurylthio)acetamide

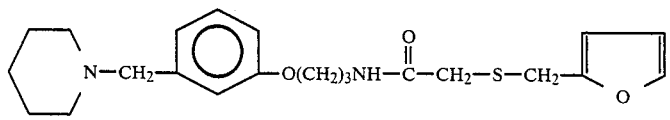

NMR (CDCl$_3$, $\delta$) 1.40–1.70(6H, m), 1.99(2H, tt, J=6 Hz, 6 Hz), 2.30–2.45(4H, m), 3.23(2H, s), 3.43(2H, t, J=6 Hz), 3.44(2H, s), 3.73(2H, s), 4.05(2H, t, J=6 Hz), 6.18–6.28(2H, m), 6.76–7.00(3H, m), 7.15–7.40(3H, m).

IR (cm$^{-1}$, film, $\nu$) 1655 (C=O).
High Resolution Mass Spectrum Molecular Weight:
Calcd. for $C_{22}H_{30}N_2O_3S$ 402.1977. Found 402.1972.

Compound 20

N-[3-{3-(piperidinomethyl)phenoxy}propyl]-2-(2-thienylthio)acetamide

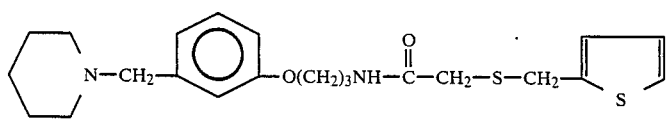

NMR (CDCl$_3$, $\delta$) 1.35–1.70(6H, m), 1.99(2H, tt, J=6 Hz, 6 Hz), 2.30–2.45(4H, m), 3.22(2H, s), 3.44(2H, s), 3.46(2H, t, J=6 Hz), 3.94(2H, s), 4.05(2H, t, J=6 Hz), 6.75–7.30(8H, m).

IR (cm$^{-1}$, film, $\nu$) 1650 (C=O).
High Resolution Mass Spectrum Molecular Weight:
Calcd. for $C_{22}H_{30}N_2O_2S_2$ 418.1749. Found 418.1757.

Compound 21

N-[3-{3-(piperidinomethyl)phenoxy}propyl]-2-(2-naphthylmethylthio)acetamide

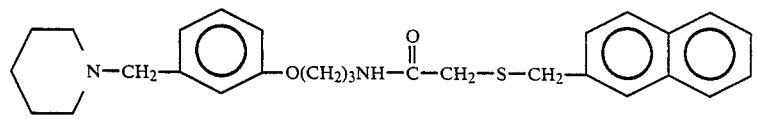

NMR (CDCl$_3$, $\delta$) 1.35–1.70(6H, m), 1.87(2H, tt, J=6 Hz, 6 Hz), 2.30–2.50(4H, m), 3.17(2H, s), 3.34(2H, t, J=6 Hz), 3.46(2H, s), 3.87(2H, s), 3.97(2H, t, J=6 Hz), 6.75–7.85(12H, m).

IR (cm$^{-1}$, film, $\nu$) 1650 (C=O).
High Resolution Mass Spectrum Molecular Weight:
Calcd. for $C_{28}H_{34}N_2O_2S$ 462.2340. Found 462.2302.

Compound 22

N-[3-{3-(piperidinomethyl)phenoxy}propyl]-2-(2-propenyl-1-thio)acetamide

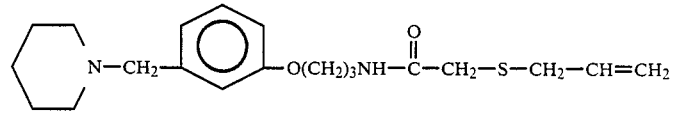

NMR (CDCl$_3$, $\delta$) 1.40–1.70(6H, m), 2.05(2H, tt, J=6.3 Hz, 6.3 Hz), 2.35–2.50(4H, m), 3.15(2H, d, J=6.8 Hz), 3.21(2H, s), 3.49(2H, s), 3.55(2H, t, J=6.3 Hz), 4.10(2H, t, J=6.3 Hz), 5.10–5.20(2H, m), 5.7–5.85(1H, m), 6.80–7.40(5H, m).

IR (cm$^{-1}$, film, $\nu$) 1650 (C=O).
High Resolution Mass Spectrum Molecular Weight:
Calcd. for $C_{20}H_{30}N_2O_2S$ 362.2027. Found 362.1984.

Compound 23
N-[3-{3-(piperidinomethyl)phenoxy}propyl]-2-(4-cyanobenzylthio)acetamide

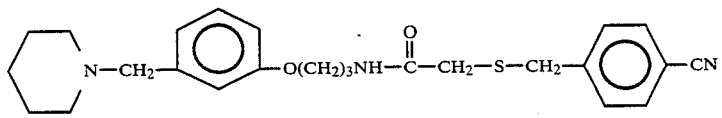

NMR (CDCl$_3$, δ) 1.35–1.70(6H, m), 2.00(2H, tt, J=6 Hz, 6 Hz), 2.30–2.45(4H, m), 3.11(2H, s), 3.44(2H, s), 3.46(2H, t, J=6 Hz), 3.73(2H, s), 4.07(2H, t, J=6 Hz), 6.40–7.30(5H, m), 7.35(2H, d, J=8 Hz), 7.57(2H, d, J=8 Hz).

IR (cm$^{-1}$, film, ν) 1650 (C=O).
High Resolution Mass Spectrum Molecular Weight:
Calcd. for C$_{25}$H$_{31}$N$_3$O$_2$S 437.2136. Found 437.2109.

Compound 24
N-[3-{3-(piperidinomethyl)phenoxy}propyl]-2-(4-methoxycarbonylbenzylthio)acetamide

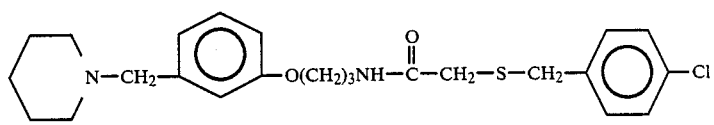

NMr (CDCl$_3$, δ) 1.30–1.80(6H, m), 1.98(2H, tt, J=6 Hz, 6 Hz), 2.30–2.50(4H, m), 3.14(2H, s), 3.44(2H, t, J=6 Hz), 3.47(2H, s), 3.74(2H, s), 3.91(3H, s), 4.06(2H, t, J=6 Hz), 6.80–7.30(5H, m), 7.32(2H, d, J=8 Hz), 7.96(2H, d, J=8 Hz).

IR (cm$^{-1}$, film, ν) 1655, 1730 (C=O).
High Resolution Mass Spectrum Molecular Weight:
Calcd. for C$_{26}$H$_{34}$N$_2$O$_4$S 470.2238. Found 470.2225.

Compound 25
N-[3-{3-(piperidinomethyl)phenoxy}propyl]-2-(5-phenylpentyl-1-thio)acetamide

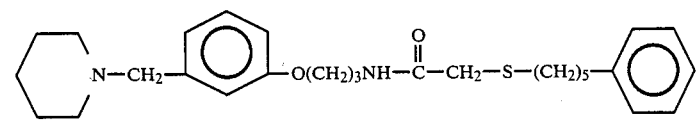

NMR (CDCl$_3$, δ) 1.30–2.70(12H, m), 2.02(2H, tt, J=6 Hz, 6Hz), 2.30–2.55(4H, m), 2.50(2H, t, J=7 Hz), 2.57(2H, t, J=7 Hz), 3.22(2H, s), 3.44(2H, s), 3.52(2H, t, J=6 Hz), 4.06(2H, t, J=6 Hz), 6.80–7.45(10H, m).

IR (cm$^{-1}$, film, ν) 1650 (C=O).
High Resolution Mass Spectrum Molecular Weight:
Calcd. for C$_{28}$H$_{40}$N$_2$O$_2$S 468.2810. Found 468.2796.

Compound 26
N-[3-{3-(piperidinomethyl)phenoxy}propyl]-2-(4-chlorobenzylthio)acetamide

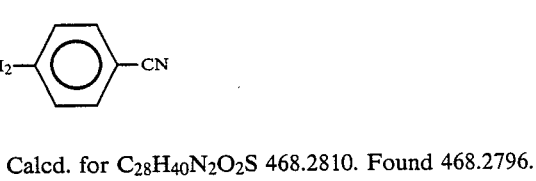

NMR (CDCl$_3$, δ) 1.40–1.70(6H, m), 1.97(2H, tt, J=6 Hz, 6 Hz), 2.30–2.45(4H, m), 3.14(2H, s), 3.42(2H, t, J=6 Hz), 3.44(2H, s), 3.67(2H, s), 4.06(2H, t, J=6 Hz), 6.80–7.30(4H, m), 7.19(2H, dd, J=9 Hz), 7.25(2H, dd, J=9 Hz).

IR (cm$^{-1}$, film, ν) 1650 (C=O).
High Resolution Mass Spectrum Molecular Weight:
Calcd. for C$_{24}$H$_{31}$N$_2$O$_2$ClS 446.1794. Found 446.1789.

Compound 27
N-[3-{3-(piperidinomethyl)phenoxy}propyl]-2-(4-methylbenzylthio)acetamide

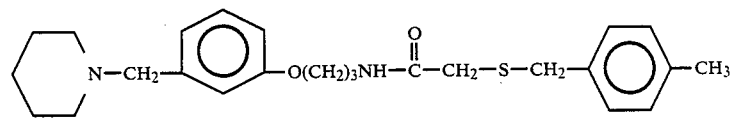

NMR (CDCl$_3$, δ) 1.30–1.60(6H, m), 1.89(2H, tt, J=6 Hz, 6 Hz), 2.24(3H, s), 2.20–2.40(4H, m), 3.08(2H, s), 3.34(2H, t, J=6 Hz), 3.37(2H, s), 3.60(2H, s), 3.96(2H, t, J=6 Hz), 6.70–7.20(8H, m).

IR (cm$^{-1}$, film, ν) 1650 (C=O).
High Resolution Mass Spectrum Molecular Weight:
Calcd. for C$_{25}$H$_{34}$N$_2$O$_2$S 426.2341. Found 426.2357.

Compound 28

[N-[3-{3-(piperidinomethyl)phenoxy}propyl]-2-(4-pyridylmethylthio)acetamide

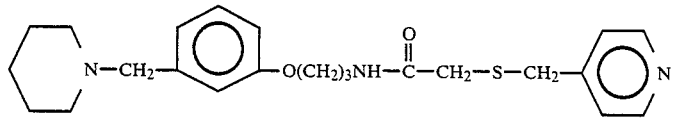

NMR (CDCl₃, δ) 1.35–1.80(6H, m), 1.97(2H, tt, J=6.4 Hz, 6.4 Hz), 2.35–2.70(4H, m), 3.14(2H, s), 3.43(2H, t, J=6.4 Hz), 3.60(2H, s), 3.68(2H, s), 4.08(2H, t, J=6.4 Hz), 6.80–7.40(7H, m), 8.45–8.60(2H, m).

IR (cm⁻¹, film, ν) 1655 (C=O).

High Resolution Mass Spectrum Molecular Weight: Calcd. for C₂₃H₃₁N₃O₂S 413.2136. Found 413.2121.

Compound 29

N-[3-{3-(piperidinomethyl)phenoxy}propyl]-2-(2-(2-benzothiazolylmethylthio)acetamide

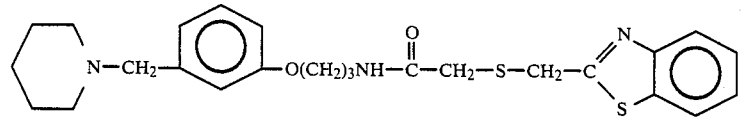

NMR (CDCl₃, δ) 1.33–1.73(7H, m), 1.96(2H, tt, J=6.0 Hz, 6.0 Hz), 2.24–2.48(4H, m), 3.30(2H, s), 3.42(2H, s), 3.44(2H, t, J=6.0 Hz), 4.03(2H, t, J=6.0 Hz), 4.14(2H, s), 6.78–7.95(8H, m).

IR (cm⁻¹, film, ν) 1645 (C=O).

High Resolution Mass Spectrum Molecular Weight: Calcd. for C₂₅H₃₁N₃O₂S₂ 469.1858. Found 469.1891.

Example 30

The compound 30 was produced in the same method as Example 1 where 1.09 g of N-[3{3-(piperidinomethyl)phenoxy}propyl]-4-chlorobutylamide was employed instead of 1.0 g of N-[3-{3-(piperidinomethyl)phenoxy}propyl]-2-chloroacetamide.

Compound 30

N-[3-{3-(piperidinomethyl)phenoxy{propyl]-4-(benzylthio)butylamide

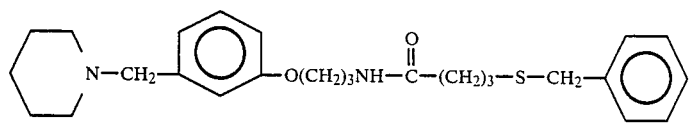

NMR (CDCl₃, δ) 1.20–2.70(18H, m), 3.32(2H, t, J=6 Hz), 3.40(2H, s), 3.63(2H, s), 3.98(2H, t, J=6 Hz), 5.80–6.10(1H, brs), 6.60–7.35(9H, m).

IR (cm⁻¹, film, ν) 1650.

High Resolution Mass Spectrum Molecular Weight: Calcd. for C₂₆H₃₆N₂O₂S 440.2470. Found 440.2497.

Examples 31–34

The compounds 31–34 were produced in the same method as Example 30 where each 3.7 mmol of the following thiols was employed instead of α-toluene-thiol.

(31) Benzenethiol
(32) 4-Methoxyphenylmethanethiol
(33) 3-Phenylpropane-1-thiol
(34) 3-Phenyl-2-propene-1-thiol

Compound 31

N-[3-{3-(piperidinomethyl)phenoxy}propyl]-4-(phenylthio)butylamide

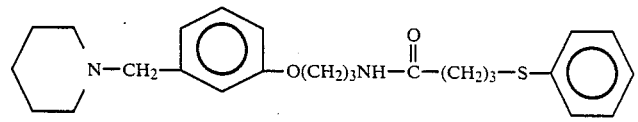

NMR (CDCl₃, δ) 1.20–2.50(16H, m), 2.90(2H, t, J=6 Hz, 6 Hz), 3.31(2H, t, J=6 Hz), 3.39(2H, s), 3.93(2H, t, J=6 Hz), 6.00–6.30(H, brs), 6.50–7.35(9H, m).

IR (cm⁻¹, film, ν) 1650 (C=O).

High Resolution Mass Spectrum Molecular Weight: Calcd. for C₂₅H₃₄N₂O₂S 426.2340. Found 246.2290.

Compound 32

N-[3-{3-(piperidinomethyl)phenoxy}propyl]-4-(4-methoxybenzylthio)butylamide

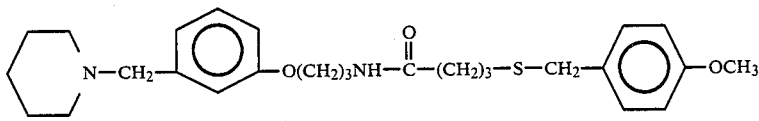

NMR (CDCl$_3$, δ) 1.30–2.60(18H, m), 3.36(2H, t, J=6 Hz), 3.45(2H, s), 3.61(2H, s), 4.02(2H, t, J=6 Hz), 5.80–6.00(H, brs), 6.70–7.30(8H, m).
IR (cm$^{-1}$, film, ν) 1650 (C=O).
High Resolution Mass Spectrum Molecular Weight: Calcd. for C$_{27}$H$_{38}$N$_2$O$_3$S 470.2603. Found 470.2594.

Compound 33

N-[3-{3-(piperidinomethyl)phenoxy}propyl]-4-(3-phenylpropyl-1-thio)butylamide

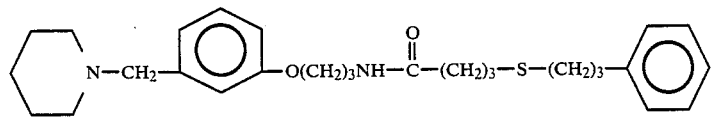

NMR (CDCl$_3$, δ) 1.30–2.90(24H, m), 3.40(2H, s), 3.45(2H, t, J=6 Hz), 3.98(2H, t, J=6 Hz), 6.05–6.35(H, brs), 6.50–7.30(9H, m),
IR (cm$^{-1}$, film, ν) 1650 (C=O).
High Resolution Mass Spectrum Molecular Weight: Calcd. for C$_{28}$H$_{40}$N$_2$O$_2$S 468.2809. Found 468.2784.

Compound 34

N-[3-{3-(piperidinomethyl)phenoxy}propyl]-4-(3-phenyl-2-propenyl-1-thio)butylamide

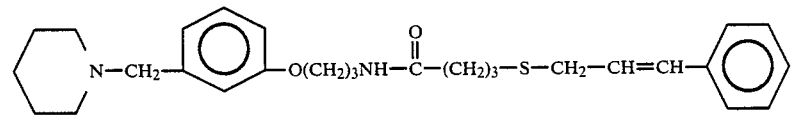

NMR (CDCl$_3$, δ) 1.30–2.80(18H, m), 3.10–3.60(4H, m), 3.41(2H, s), 3.96(2H, t, J=6 Hz), 5.90–7.40(11H, m).
IR (cm$^{-1}$, film, ν) 1650 (C=O).
High Resolution Mass Spectrum Molecular Weight: Calcd. for C$_{28}$H$_{38}$N$_2$O$_2$S 477.2653. Found 466.2607.

Example 35

The compound 35 was produced in the same method as Example 1 where 1.72 g of N-[3-{3-(piperidinomethyl)phenoxy}propyl]-6-bromohexylamide was employed instead of 1.0 g of N-[3-{3-(piperidinomethyl)phenoxy}propyl]-2-chloroacetamide.

Compound 35

N-[3-{3-(piperidinomethyl)phenoxy}propyl]-6-(benzylthio)hexylamide

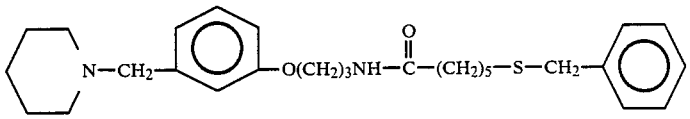

NMR (CDCl$_3$, δ) 1.20–2.60(22H, m), 3.37(2H, t, J=6 Hz), 3.40(2H, s), 3.62(2H, s), 3.98(2H, t, J=6 Hz), 5.90–6.20(1H, brs), 6.60–7.40(9H, m).
IR (cm$^{-1}$, film, ν) 1640 (C=O).
High Resolution Mass Spectrum Molecular Weight: Calcd. for C$_{28}$H$_{40}$N$_2$O$_2$S 468.2810. Found 468.2724.

Examples 36–39

The compounds 36–39 were produced in the same method as Example 35 where each 3.7 mmole of the following thiols was employed instead of α-toluenethiol.

(36) Benzenethiol
(37) 4-Methoxyphenylmethanethiol
(38) 3-Phenylpropane-1-thiol
(39) 3-Phenyl-2-propene-1-thiol

Compound 36
N-[3-{3-(piperidinomethyl)phenoxy}propyl]-6-(phenylthio)hexylamide

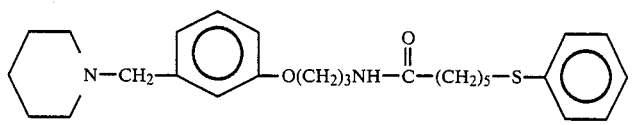

NMR (CDCl$_3$, δ) 1.20–3.00(22H, m), 3.35(2H, t, J=6 Hz), 3.40(2H, s), 3.97(2H, t, J=6 Hz), 5.90–6.10(H, brs), 6.70–7.40(9H, m).
IR (cm$^{-1}$, film, ν) 1650 (C=O).
High Resolution Mass Spectrum Molecular Weight: Calcd. for C$_{27}$H$_{38}$N$_2$O$_2$S 454.2654. Found 454.2638.

Compound 37
N-[3-{3-(piperidinomethyl)phenoxy}propyl]-6-(4-methoxybenzylthio)hexylamide

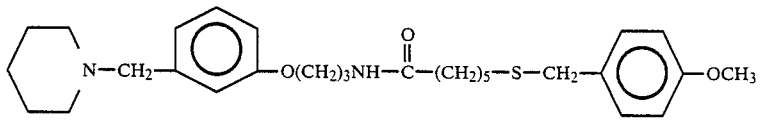

NMR (CDCl$_3$, δ) 1.20–2.60(22H, m), 3.40(2H, s), 3.40(2H, t, J=6 Hz), 3.60(2H, s), 3.73(3H, s), 3.99(2H, t, J=6 Hz), 5.80–6.10(H, brs), 6.55–7.35(8H, m).
IR (cm$^{-1}$, film, ν) 1650.
High Resolution Mass Spectrum Molecular Weight: Calcd. for C$_{29}$H$_{42}$N$_2$O$_3$S 498.2915. Found 498.2913.

Compound 38
N-[3-{3-(piperidinomethyl)phenoxy}propyl]-6-(3-phenylpropyl-1-thio)hexylamide

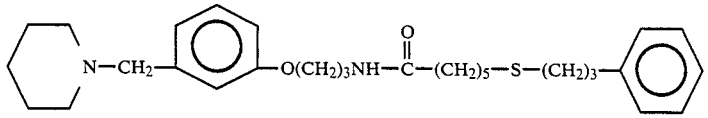

NMR (CDCl$_3$, δ) 1.35–1.70(6H, m), 1.80–2.05(4H, m), 2.17(2H, t, J=6.3 Hz), 2.30–2.45(4H, m), 2.45–2.55(4H, m), 2.71(2H, t, J=7.3 Hz), 3.44(2H, s), 3.46(2H, t, J=5.9 Hz), 4.05(2H, t, J=5.9 Hz), 5.85(1H, brs), 6.80–7.30(9H, m).
IR (cm$^{-1}$, film, ν) 1640 (C=O).
High Resolution Mass Spectrum Molecular Weight: Calcd. for C$_{30}$H$_{44}$N$_2$O$_2$S 496.3122. Found 496.3113.

Compound 39
N-[3-{3-(piperidinomehtyl)phenoxy}propyl]-6-(3-phenyl-2-propenyl-1-thio)hexylamide

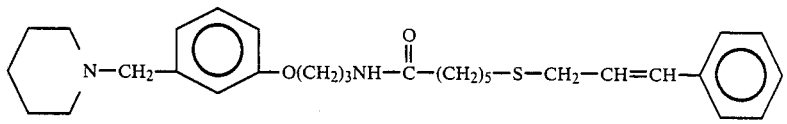

NMR (CDCl$_3$, δ) 1.20–2.60(22H, m), 3.00–3.60(6H, m), 4.00(2H, t, J=6 Hz), 5.80–7.40(10H, m).
IR (cm$^{-1}$, film, ν) 1650 (C=O).
High Resolution Mass Spectrum Molecular Weight: Calcd. for C$_{30}$H$_{42}$N$_2$O$_2$S 494.2966. Found 494.2909.

Example 40
To a solution of 0.1 ml of 2-propanethiol in 4 ml of dimethylformamide was added 0.044 g of 60% sodium hydride in an ice bath. The mixture was stirred at room tempercture for 30 minutes, and then N-[3-{3-(piperidinomethyl)phenoxy}propyl]-2-chloroacetamide solution prepared by dissolving 0.3 g of the above amide in 6 ml of dimethylformamide was added dropwise to this mixture. The mixture was stirred overnight, and extraction was carried out by adding benzene and water. The benzene layer was dried over anhydrous magnesium sulfate, and the solvent was evaporated in vacuo. The residue was purified by silica gel column chromtography using methanol:dichloromethane=1:19 as developing solvent, and 0.18 g of the following oily compound was obtained.

Compound 40

N-[3-{3-(piperidinomethyl)phenoxy}propyl]-2-(2-propylthio)acetamide

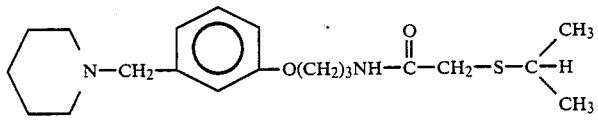

NMR (CDCl$_3$, δ) 1.26(6H, d, J=6 Hz), 1.40–1.70(6H, m), 2.04(2H, tt, J=6 Hz, 6 Hz), 2.30–2.45(4H, m), 2.92(H, qq, J=6 Hz, 6 Hz), 3.27(2H, s), 3.45(2H, s), 3.54(2H, t, J=6 Hz), 4.08(2H, t, J=6 Hz), 6.80–7.30(4H, m), 7.35–7.45(H, brs).

IR (cm$^{-1}$, film, ν) 1650 (C=O).

High Resolution Mass Spectrum Molecular Weight: Calcd. for C$_{20}$H$_{32}$N$_2$O$_2$S 364.2184. Found 364.2171.

Examples 41–43

The compounds 41–43 were produced in the same method as Example 1 in which either of the following chloroacetamides was employed instead of 1.0 g of N-[3-{3-piperidinomethyl)phenoxy}propyl]-2-chloroacetamide.

(41) N-[3-{3-(N',N'-dimethylaminomethyl)phenoxy}propyl]-2-chloroacetamide 0.88 g
(42) N-[3-{3-(1-pyrrolidinylmethyl)phenoxy}propyl]-2-chloroacetamide 0.96 g
(43) N-[3-{3-(1-perhydroazepinylmethyl)phenoxy}propyl]-2-chloroacetamide 1.04 g

Compound 41

N-[3-{3-(N',N'-dimethylaminomethyl)phenoxy}propyl]-2-(benzylthio)acetamide

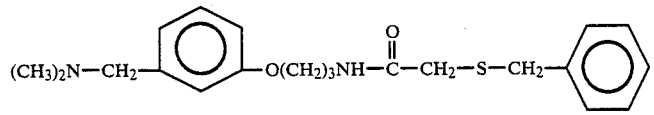

NMR (CDCl$_3$, δ) 1.97(2H, tt, J=6 Hz, 6 Hz), 2.26(1H, t, J=6Hz), 2.26(6H, s), 3.17(2H, s), 3.40(2H, d, t, J=6 Hz, 6 Hz), 3.42(2H, s), 3.71(2H, s, 4.05(2H, t, J=6 Hz), 6.80–7.40(9H, m).

IR (cm$^{-1}$, film, ν) 1650 (C=O).

High Resolution Mass Spectrum Molecular Weight: Calcd. for C$_{21}$H$_{28}$N$_2$O$_2$S 372.1871. Found 372.1838.

Compound 42

N-[3-{3-(1-pyrrolidinylmethyl)phenoxy}propyl]-2-(benzylthio)acetamide

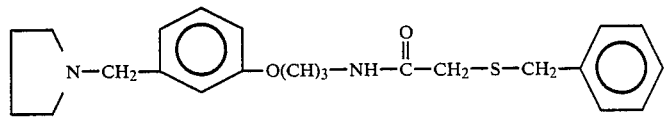

NMR (CDCl$_3$, δ) 1.17(1H, t, J=6 Hz), 1.70–1.90(4H, m), 1.95(2H, tt, J=6 Hz, 6Hz), 2.45–2.58(4H, m), 3.15(2H, s), 3.40(2H, d, t, J=6 Hz), 3.59(2H, s), 3.70(2H, s), 4.04(2H, t, J=6 Hz), 6.68–7.39(9H, m).

IR (cm$^{-1}$, film, ν) 1665 (C=O).

High Resolution Mass Spectrum Molecular Weight: Calcd. for C$_{23}$H$_{30}$N$_2$O$_2$S 398.2028. Found 398.2043.

Compound 43

N-[3-{3-(1-perhydroazepinylmethyl)phenoxy}propyl]-2-(benzylthio)acetamide

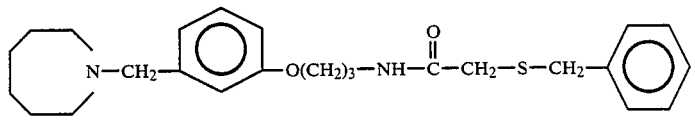

NMR (CDCl$_3$, δ) 1.40–1.75(8H, m), 1.96(2H, tt, J=6 Hz, 6 Hz), 2.50–2.74(4H, m), 3.17(2H, s), 3.41(2H, d, t, J=6 Hz, 6 Hz), 3.60(2H, brs), 3.70(2H, s), 4.04(2H, t, J=6 Hz), 6.80–7.35(9H, m).

IR (cm$^{-1}$, film, ν) 1650 (C=O).

High Resolution Mass Spectrum Molecular Weight: Calcd. for C$_{25}$H$_{34}$N$_2$O$_2$S 426.2341. Found 426.2341.

Example 44

0.11 g of the compound 1 (N-[3-{3-(piperidinomethyl)phenoxy}propyl]-2-(benzylthio)acetamide) was dissolved in a mixed solvent of 4 ml of methanol and 2 ml of water, and stirred. 0.063 g of sodium metaperiodate was added to this solution, and stirred for 24 hours. 10 ml of water and 50 ml of dichloromethane were added, and extraction was carried out. The dicloromethane layer was dried over anhydrous magnesium sulfate, and the solvent was evaporated in vacuo. The residue was purified by silica gel column chromatography using methanol:dichloromethane=1:19 as developing solvent, and 0.08 g of the following colorless glassy compound was obtained.

Compound 44

N-[3-{3-(piperidinomehtyl)phenoxy}propyl]-2-(benzyl-sulfinyl)acetamide

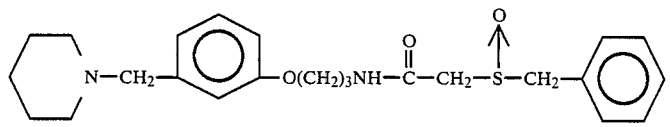

NMR (CDCl$_3$, δ) 1.35–1.65(6H, m), 2.05(2H, tt, J=6.3 Hz), 3.19(1H, d, J=13 Hz), 3.44(2H, s), 3.52(H, d, J=13 Hz), 3.56(2H, t, J=6.3 Hz), 4.06(2H, t, J=6.3 Hz), 4.09(1H, d, J=13 Hz), 4.17(1H, d, J=13 Hz), 6.75–7.40(10H, m).

IR (cm$^{-1}$, film, ν) 1660 (C=O), 1030 (S→O).

High Resolution Mass Spectrum Molecular Weight: Calcd. for C$_{24}$H$_{32}$N$_2$O$_3$S 428.2133. Found 428.2152.

Example 45

0.13 g of the compound 1 was dissolved in 2 ml of acetic acid, and this solution was heated to 100° C. To the solution was added dropwise 0.04 ml of 60% aqueous hydrogen peroxide solution, and stirred for one hour. After cooling, the solution was neutralized by using aqueous sodium hydrogen carbonate solution. 20 ml of water and 40 ml of dichloromethane were added to the neutralized solution, and extraction was carried out. The dichloromethane layer was dried over anhydrous magnesium sulfate, and solvent was evaporated in vacuo. The residue was purified by silica gel column chromatography using methanol:dichloromethane=1:19 as developing solvent, and 0.04 g of the following colorless glassy compound was obtained.

Compound 45

N-[3-{3-(piperidinomethyl)phenoxy}propyl]-2-(benzyl-sulfonyl)acetamide

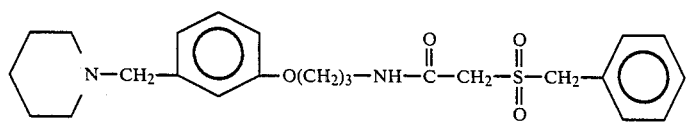

NMR (CDCl$_3$, δ) 1.40–1.55(6H, m), 2.03(2H, tt, J=6.3 Hz), 2.30–2.45(4H, m), 3.45(2H, s), 3.51(2H, t, J=6.3 Hz), 3.72(2H, s), 4.07(2H, t, J=6.3 Hz), 4.42(2H, s), 6.70–7.50(10H, m).

IR (cm$^{-1}$, film, ν) 1660 (C=O), 1120, 1310 (S=O).

High Resolution Mass Spectrum Molecular Weight: Calcd. for C$_{24}$H$_{32}$N$_2$O$_4$S 444.2083. Found 444.2102.

Example 46

The compound 46 was produced in the same method as Example 44 in which 0.11 g of the compound 19 was employed instead of the compound 1.

Compound 46

N-[3-[3-(piperidinomethyl)phenoxy}propyl]-2-(furfurylsulfinyl)acetamide

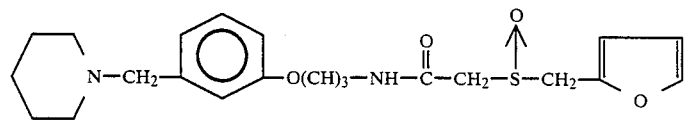

NMR (CDCl$_3$, δ) 1.40–1.70(6H, m), 2.04(2H, tt, J=6.3 Hz, J=6.3 Hz), 2.30–2.50(4H, m), 3.31(1H, d, J=14.2 Hz), 3.44(2H, s), 3.55(2H, dt, J=6.3Hz, J=6.3 Hz), 3.58(1H, d, J=14.2 Hz), 4.05(2H, t, J=6.3 Hz), 4.16(1H, d, J=14.2 Hz), 4.26(1H, d, J=14.2 Hz), 6.39(1H, t, J=1.5 Hz), 6.46(1H, d, J=1.5 Hz), 6.75–7.30(5H, m), 7.43(1H, d, J=1.5 Hz).

IR (cm$^{-1}$, film, ν) 1660 (C=O), 1020 (S→O).

High Resolution Mass Spectrum Molecular Weight: Calcl. for C$_{22}$H$_{30}$N$_2$O$_5$S 418.1926. Found 418.1922.

Example 47

The compound 47 was produced in the same method as Example 45 in which 0.13 g of the compound 19 was employed instead of the compound 1.

Compound 47

N-[3-[3-(piperidinomethyl)phenoxy]propyl]-2-(furfurylsulfonyl)acetamide

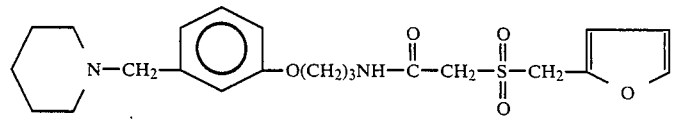

NMR (CDCl$_3$, δ) 1.40–1.70(6H, m), 2.03(2H, tt, J=6.3 Hz, J=6.3 Hz), 2.30–2.50(4H, m), 3.44(2H, s), 3.53(2H, dt, J=6.3 Hz, J=6.3 Hz), 3.83(2H, s), 4.06(2H, t, J=6.3 Hz), 4.53(2H, s), 6.43(1H, t, J=1.5 Hz), 6.59(1H, d, J=1.5 Hz), 6.70–7.25(5H, m), 7.49(1H, d, J=1.5 Hz).

IR (cm$^{-1}$, KBr, ν) 1660 (C=O), 1140, 1315 (S=O). Melting Point 107.4°–108.8° C.

High Resolution Mass Spectrum Molecular Weight: Calcd. for $C_{22}H_{30}N_2O_5S$ 434.1875. Found 434.1871.

Examples 48–61

The compounds 48–61 were produced in the same method as Example 1 where each 3.7 mmole of the following thiols was employed instead of α-toluenethiol.

(48) 4-Carboxybenzylthiol
(49) 4-Nitrobenzylthiol
(50) 4-Methylthiobenzylthiol
(51) 2,3-Dimethoxybenzylthiol
(52) 4-Acetoxybenzylthiol
(53) 4-Hydroxybenzylthiol
(54) 3,4-Methylenedioxybenzylthiol
(55) 4-Acetamidebenzylthiol
(56) 4-Trifluoromethylbenzylthiol
(57) 3-Furylmethanethiol
(58) 1-(2-Furyl)ethanethiol
(59) 2-Pyridylmethanethiol
(60) 3-Pyridylmethanethiol
(61) 3-Thenylthiol The thiol (48) was obtained by hydrolysis of the thiol (24), and the thiol (53) was obtained by hydrolysis of the thiol (52). Each hydrolysis was carried out in aqueous methanol-alkali.

Compound 48
N-[3-{3-(piperidinomethyl)phenoxy}propyl]-2-(4-carboxylbenzylthio)acetamide

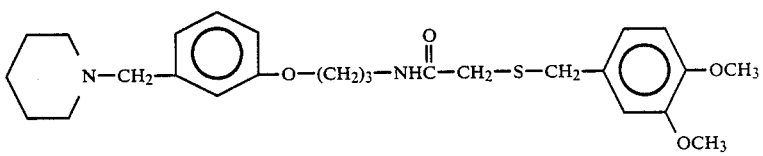

NMR (300 MHz, CDCl$_3$, δ) 1.50–1.75(2H, m), 1.61(2H, tt, J=6.3 Hz, 6.3 Hz), 1.80–2.10(4H, m), 2.80–3.20(4H, m), 2.91(2H, dt, J=6.3 Hz, 6.3 Hz), 3.25(2H, s), 3.69(2H, t, J=6.3 Hz), 3.76(2H, s), 3.95(2H, s), 5.93(1H, brs), 6.70–6.90(2H, m), 7.20–7.40(2H, m), 7.29(2H, d, J=8.3 Hz), 8.09(2H, d, J=8.3 Hz).

IR (cm$^{-1}$, KBr, ν) 1660 (C=O), 1600 (C=O).

High Resolution Mass Spectrum Molecular Weight: Calcd. for $C_{25}H_{32}N_2O_4S$ 456.2083. Found 456.2088.

Compound 49
N-[3-{3-(piperidinomethyl)phenoxy}propyl]-2-(4-nitrobenzylthio)acetamide

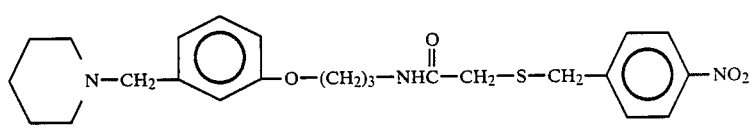

NMR (300 MHz, CDCl$_3$, δ) 1.40–1.70(6H, m), 2.00(2H, tt, J=6.3 Hz, 6.3 Hz), 2.30–2.45(4H, m), 3.12(2H, s), 3.44(2H, s), 3.45(2H, dt, J=6.3 Hz, 6.3 Hz), 4.07(2H, t, J=6.3 Hz), 6.80–7.30(5H, m), 7.41(2H, d, J=6.8 Hz), 8.14(2H, d, J=6.8 Hz).

IR (cm$^{-1}$, film, ν) 1650 (C=O).

High Resolution Mass Spectrum Molecular Weight: Calcd. for $C_{24}H_{31}N_3O_4S$ 457.2034. Found 457.2024.

Compound 50
N-[3-{3-(piperidinomethyl)phenoxy}propyl]-2-(4-methylthiobenzylthio)acetamide

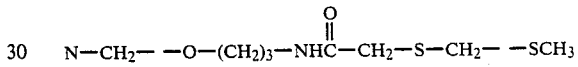

NMR (300 MHz, CDCl$_3$, δ) 1.40–1.70(6H, m), 1.97(2H, tt, J=6.3 Hz, 6.3 Hz), 2.30–2.45(4H, m), 2.46(3H, s), 3.14(2H, s), 3.41(2H, dt, J=6.3 Hz, 6.3 Hz), 3.44(2H, s), 4.05(2H, t, J=6.3 Hz), 6.80–7.30(9H, m).

IR (cm$^{-1}$, KBr, ν) 1650 (C=O).

High Resolution Mass Spectrum Molecular Weight: Calcd. for $C_{25}H_{34}N_2O_2S_2$ 458.2062. Found 458.2071.

Compound 51
N-[3-{3-(piperidinomethyl)phenoxy}propyl]-2-(3,4-dimethoxybenzylthio)acetamide

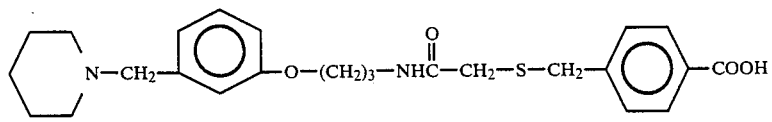

NMR (300 MHz, CDCl$_3$, δ) 1.40–1.65(6H, m), 1.97(2H, tt, J=6.3 Hz, 6.3 Hz), 2.30–2.45(4H, m), 3.15(2H, s), 3.44(2H, s), 3.45(2H, dt, J=6.3 Hz, 6.3 Hz), 3.67(2H, s), 3.83(3H, s), 3.85(3H, s), 4.05(2H, t, J=6.3 Hz), 6.75–7.00(6H, m), 7.15–7.30(2H, m).

IR (cm$^{-1}$, film, ν) 1650 (C=O).

High Resolution Mass Spectrum Molecular Weight: Calcd. for $C_{26}H_{36}N_2O_4S$ 472.2396. Found 472.2396.

Compound 52

N-[3-{3-(piperidinomethyl)phenoxy}propyl]-2-(4-acetoxybenzylthio)acetamide

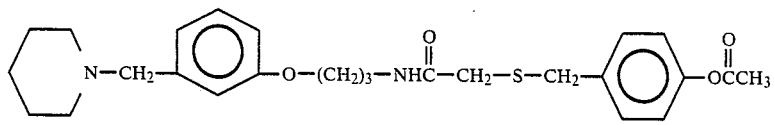

NMR (300 MHz, CDCl₃, δ) 1.40–1.65 (6H, m), 1.97(2H, tt, J=6.3 Hz, 6.3 Hz), 2.29(3H, s), 2.30–2.45(4H, m), 3.16(2H, s), 3.43(2H, dt, J=6.3 Hz, 6.3 Hz), 3.44(2H, s), 3.69(2H, s), 4.05(2H, t, J=6.3 Hz), 6.80–7.30(5H, m), 6.90(2H, d, J=8.3 Hz), 7.26(2H, d, J=8.3 Hz).

IR (cm⁻¹, film, ν) 1660 (C=O).

High Resolution Mass Spectrum Molecular Weight: Calcd. for C₂₆H₃₄N₂O₄S 470.2239. Found 470.2250.

Compound 53

N-[3-{3-(piperidinomethyl)phenoxy}propyl]-2-(4-hydroxybenzylthio)acetamide

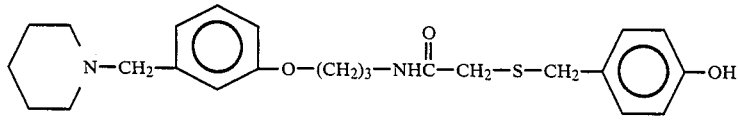

NMR (300 MHz, CDCl₃, δ) 1.40–1.70(6H, m), 1.70(2H, tt, J=6.0 Hz, 6.0 Hz), 2.50–2.65(4H, m), 3.22(2H, dt, J=6.0 Hz, 6.0 Hz), 3.32(2H, s), 3.52(2H, s), 3.55(2H, t, J=6.0 Hz), 6.45(1H, brs), 6.50(2H, d, J=8.3 Hz), 6.75–7.20(4H, m), 7.01(2H, d, J=8.3 Hz).

IR (cm⁻¹, film, ν) 1645 (C=O).

High Resolution Mass Spectrum Molecular Weight: Calcd. for C₂₄H₃₂N₂O₃S 428.2133. Found 428.2120.

Compound 54

N-[3-{3-(piperidinomethyl)phenoxy}propyl]-2-(3,4-methylenedioxybenzylthio)acetamide

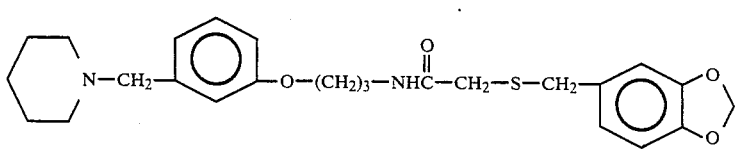

NMR (300 MHz, CDCl₃, δ) 1.40–1.65(6H, m), 1.99(2H, tt, J=6.3 Hz, 6.3 Hz), 2.30–2.45(4H, m), 3.15(2H, s), 2.38(2H, dt, J=6.3 Hz, 6.3 Hz), 2.39(2H, s), 3.15(2H, s), 4.06(2H, t, J=6.3 Hz), 5.93(2H, s), 6.65–7.00(6H, m), 7.15–7.30(2H, m).

IR (cm⁻¹, film, ν) 1650 (C=O).

High Resolution Mass Spectrum Molecular Weight: Calcd. for C₂₅H₃₂N₂O₄S 456.2083. Found 456.2088.

Compound 55

N-[3-{3-(piperidinomethyl)phenoxy}propyl]-2-(4-acetamidebenzylthio)acetamide

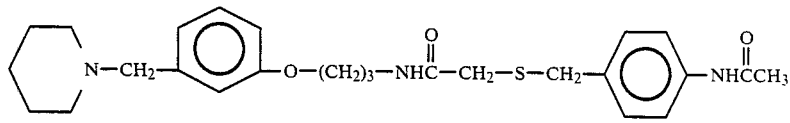

NMR (300 MHz, CDCl₃, δ) 1.40–1.65(6H, m), 1.95(2H, tt, J=6.0 Hz, 6.0 Hz), 2.15(3H, s), 2.30–2.45(4H, m), 3.14(2H, s), 3.40(2H, dt, J=6.0 Hz, 6.0 Hz), 3.45(2H, s), 3.67(2H, s), 4.02(2H, t, J=6.0 Hz), 6.80–7.00(3H, m), 7.10–7.25(2H, m), 7.17(2H, d, J=8.3 Hz), 7.41(2H, d, J=8.3 Hz).

IR (cm⁻¹, film, ν) 1650 (C=O).

High Resolution Mass Spectrum Molecular Weight: Calcd. for C₂₆H₃₅N₃O₃S 469.2399. Found 469.2399.

Compound 56

N-[3-{3-(piperidinomethyl)phenoxy}propyl]-2-(4-trifluoromethylbenzylthio)acetamide

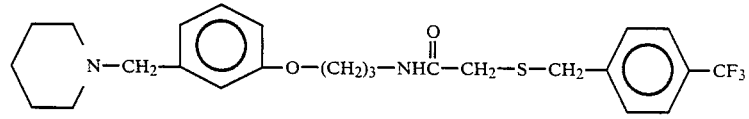

NMR (300 MHz, CDCl₃, δ) 1.40–1.65(6H, m), 1.97(2H, tt, J=6.0 Hz, 6.0 Hz), 2.30–2.45(4H, m), 3.14(2H, s), 3.42(2H, dt, J=6.0 Hz, 6.0 Hz), 3.44(2H, s), 3.74(2H, s), 4.05(2H, t, J=6.0 Hz), 6.80–7.00(3H, m), 7.13(1H, brs), 7.20–7.30(1H, m), 7.35(2H, d, J=8.3 Hz), 7.53(2H, d, J=8.3 Hz).

IR (cm$^{-1}$, film, $\nu$) 1650 (C=O).

High Resolution Mass Spectrum Molecular Weight: Calcd. for $C_{25}H_{31}N_2O_2SF_3$ 480.2058. Found 480.2052.

Compound 57
N-[3-{3-(piperidinomethyl)phenoxy}propyl]-2-(3-furyl-methylthio)acetamide

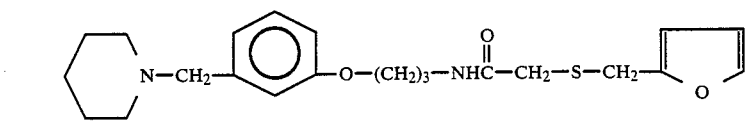

NMR (300 MHz, CDCl$_3$, $\delta$) 1.36–1.72(6H, m), 2.00(2H, tt, J=6.0 Hz, 6.0 Hz), 2.30–2.46(4H, m), 3.17(2H, s), 3.44(2H, s), 3.47(2H, dt, J=6.0 Hz, 6.0 Hz), 3.56(2H, s), 4.06(2H, t, J=6.0 Hz), 6.34(1H, d, J=1.5 Hz), 6.82(1H, dd, J=7.5 Hz, 2.5 Hz), 6.92(1H, d, J=7.5 Hz), 6.95(1H, brs), 7.17–7.27(1H, m), 7.22(1H, dd, J=7.5 Hz, 7.5 Hz), 7.32(1H, s), 7.36(1H, d, J=1.5 Hz).

IR (cm$^{-1}$, film, $\nu$) 1642 (C=O).

High Resolution Mass Spectrum Molecular Weight: Calcd. for $C_{22}H_{30}N_2O_3S$ 402.1977. Found 402.1969.

Compound 58
N-[3-{3-(piperidinomethyl)phenoxy}propyl]-2-{1-(2-furyl)ethylthio}acetamide

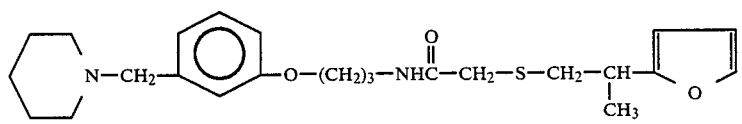

NMR (300 MHz, CDCl$_3$, $\delta$) 1.35–1.65(6H, m), 1.59(3H, d, J=7.3 Hz), 1.97(2H, tt, J=6.3 Hz, 6.3 Hz), 2.30–2.45(4H, m), 3.21(2H, s), 3.43(2H, dt, J=6.3 Hz, 6.3 Hz), 3.45(2H, s), 4.03(2H, t, J=6.3 Hz), 4.05(1H, q, J=7.3 Hz), 6.15(1H, d, J=2.9 Hz), 6.27(1H, dd, J=2.9 Hz, 3.4 Hz), 6.80–7.35(6H, m).

IR (cm$^{-1}$, film, $\nu$) 1650 (C=O).

High Resolution Mass Spectrum Molecular Weight: Calcd. for $C_{23}H_{32}N_2O_3S$ 416.2134. Found 416.2145.

Compound 59
N-[3-{3-(piperidinomethyl)phenoxy}propyl]-2-(2-pyridylmethylthio)acetamide

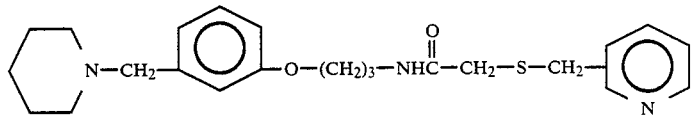

NMR (300 MHz, CDCl$_3$, $\delta$) 1.40–1.65(6H, m), 2.02(2H, tt, J=5.9 Hz, 5.9 Hz), 2.30–2.45(4H, m), 3.17(2H, s), 3.44(2H, s), 3.47(2H, dt, J=5.9 Hz, 5.9 Hz), 3.84(2H, s), 4.05(2H, t, J=5.9 Hz), 6.75–7.00(3H, m), 7.10–7.30(3H, m), 7.60–7.80(2H, m), 8.48(1H, d, J=5.0 Hz).

IR (cm$^{-1}$, film, $\nu$) 1660 (C=O).

High Resolution Mass Spectrum Molecular Weight: Calcd. for $C_{23}H_{31}N_3O_2S$ 413.2137. Found 413.2138.

Compound 60
N-[3-{3-(piperidinomethyl)phenoxy}propyl]-2-(3-pyridylmethylthio)acetamide

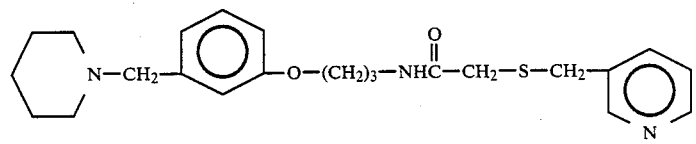

NMR (300 MHz, CDCl$_3$, $\delta$) 1.40–1.65(6H, m), 2.00(2H, tt, J=6.3 Hz, 6.3 Hz), 2.30–2.45(4H, m), 3.15(2H, s), 3.44(2H, s), 3.46(2H, dt, J=6.3 Hz), 4.07(2H, t, J=6.3 Hz), 6.80–7.00(3H, m), 7.10–7.30(3H, m), 7.50–7.60(1H, m), 8.50–8.60(2H, m).

IR (cm$^{-1}$, film, $\nu$) 1650 (C=O).

High Resolution Mass Spectrum Molecular Weight: Calcd. for $C_{23}H_{31}N_3O_2S$ 413.2137. Found 413.2139.

Compound 61
N-[3-{3-(piperidinomethyl)phenoxy}propyl]-2-(3-thenylthio)acetamide

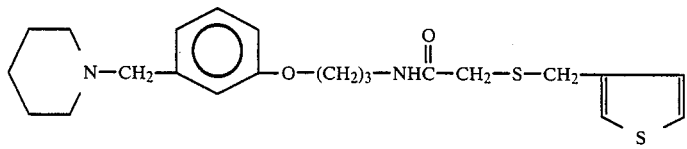

NMR (300 MHz, CDCl₃, δ) 1.38–1.65(6H, m), 1.98(2H, tt, J=6.3 Hz, 6.3 Hz), 2.35–2.45(4H, m), 3.16(2H, s), 3.43(2H, dt, J=6.3 Hz, 6.3 Hz), 3.73(2H, s), 4.05(2H, t, J=6.3 Hz), 6.80–7.30(8H, m).
IR (cm⁻¹, film, ν) 1675 (C=O).

Example 62
The compound 62 was produced in the same method as Example 1 where N-[3-{3-(N,N'-dimethylaminomethyl)phenoxy}propyl]-2-chloroacetamide and 2-furylmethanethiol were employed.

Compound 62
N-[3-{3-(dimethylaminomethyl)phenoxy}propyl]-2-(furfurylthio)acetamide

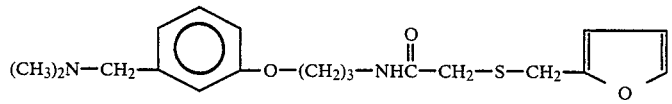

NMR (300 MHz, CDCl₃, δ) 1.99(2H, tt, J=6.3 Hz, 6.3 Hz), 2.25(6H, s), 3.25(2H, s), 3.40(2H, s), 3.45(2H, dt, J=6.3 Hz, 6.3 Hz), 3.73(2H, s), 4.05(2H, t, J=6.3 Hz), 6.18(1H, d, J=3.0 Hz), 6.29(1H, dd, J=3.0 Hz, 1.9 Hz), 6.80–7.40(6H, m).
IR (cm⁻¹, film, ν) 1650 (C=O).
High Resolution Mass Spectrum Molecular Weight: Calcd. for C₁₉H₂₆N₂O₃S 362.1663. Found 362.1653.

Example 63
The compound 63 was produced in the same method as Example 1 where N-[3-{3-(1-pyrrolidinylmethyl)phenoxy}propyl]-2-chloroacetamide and 2-furylmethanethiol were employed.

Compound 63
N-[3-{3-(1-pyrrolidinylmethyl)phenoxy}propyl]-2-(furfurylthio)acetamide

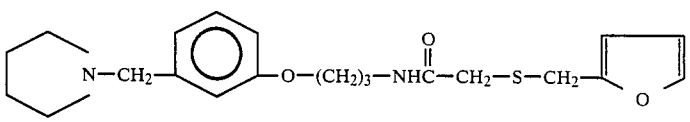

NMR (300 MHz, CDCl₃, δ) 1.80–1.95(4H, m), 1.99(2h, tt, J=5.9 Hz, 5.9 Hz), 2.50–2.70(4H, m), 3.23(2H, s), 3.45(2H, dt, J=5.9 Hz, 5.9 Hz), 3.64(2H, s), 3.74(2H, s), 4.06(2H, t, J=5.9 Hz), 6.18(1H, d, J=2.8 Hz), 6.28(1H, dd, J=2.8 Hz, 3.1 Hz), 6.80–7.35(6H, m).
IR (cm⁻¹, film, ν) 1650 (C=O).
High Resolution Mass Spectrum Molecular Weight: Calcd. for C₂₁H₂₈N₂O₃S 388.1821. Found 388.1826.

Example 64
The compound 64 was produced in the same method as Example 1 where N-[3-{3-(4-hydroxypiperidinomethyl)phenoxy}propyl]-2-chloroacetamide and 2-furylmethanethiol were employed.

Compound 64
N-[3-{3-(4-hydroxypiperidinomethyl)phenoxy}propyl]-2-(furfurylthio)acetamide

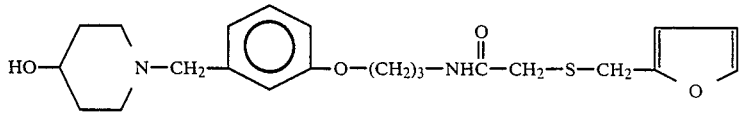

NMR (300 MHz, CDCl₃, δ) 1.55–1.80(3H, m), 1.85–1.95(2H, m), 1.99(2H, tt, J=6.0 Hz, 6.0 Hz), 2.15–2.25(2H, m), 2.70–2.85(2H, m), 3.23(2H, s), 3.44(2H, dt, J=6.0 Hz, 6.0 Hz), 3.50(2H, s), 3.73(2H, s), 3.70–3.80(1H, m), 4.05(2H, t, J=6.0 Hz), 6.18(1h, d, J=3.2 Hz), 6.28(1H, dd, J=1.1 Hz, 3.2 Hz), 6.80–7.00(3H, m), 7.15–7.30(2H, m), 7.33(1H, d, J=1.1 Hz).
IR (cm⁻¹, film, ν) 1650 (C=O).
High Resolution Mass Spectrum Molecular Weight: Calcd. for C₂₂H₃₀N₂O₄S 418.1926. Found 418.1910.

Example 65

1.51 g (3.75 mmol) of the compound 19 (N-[3-{3-(piperidinomethyl)phenoxy}propyl]-2-(furfurylthio)acetamide) was added to ethanol solution containing 3.75 mmole of hydrogen chloride gas, and stirred at room temperature for one hour. Ethanol was evaporated under reduced pressure to obtain white crystals. This crystals were dissolved in a small amount of ethanol, and ether was added. The crystals deposited were collected, and dried to obtain hydrochloride of the compound 19.

Yield: 9.92 g.
M.P.: 98.0°-99.5° C.

Example 66

0.50 g (1.24 mmol) of the compound 19 was dissolved in 3 ml of ethanol. 1.24 mmole of oxalic acid was added to this solution, and stirred at room temperature for one hour. This mixture was treated in the same manner as Example 65, and white crystals of oxalate of the compound 19 were obtained.

Yield: 0.53 g.
M.P.: 111.6°-112.0° C.

Example 67

The compound 67 was produced in the same method as Example 44 where 0.11 g of the compound 57 (N-[3-{3-(piperidinomethyl)phenoxy}propyl]-2-(3-furylmethylthioacetamide) was employed.

Compound 67

N-[3-{3-(piperidinomethyl)phenoxy}propyl]-2-(3-furylmethylsulfinyl)acetamide

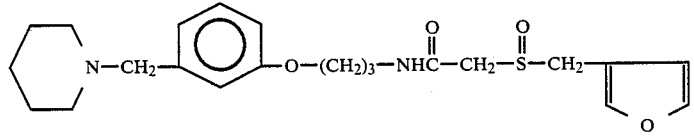

NMR (300 MHz, CDCl$_3$, δ) 1.40-1.50(2H, m), 1.55-1.70(4H, m), 2.04(2H, tt, J=6.3 Hz, 6.3 Hz), 2.30-2.50(4H, m), 3.27(1H, d, J=14.1 Hz), 3.47(2H, s), 3.54(2H, dt, J=6.3 Hz, 6.3 Hz), 3.55(1H, d, J=14.1 Hz), 3.93(1H, d, J=13.7 Hz), 4.04(1H, d, J=13.7 Hz), 4.06(2H, t, J=6.3 Hz), 6.45(1H, s), 6.75-6.95(3H, m), 7.02(1H, brs), 7.15-7.25(1H, m), 7.43(1H, s), 7.51(1H, s).

IR (cm$^{-1}$, film, ν) 1650 (C=O), 1025 (S→O).

High Resolution Mass Spectrum Molecular Weight: Calcd. for C$_{23}$H$_{30}$N$_2$O$_4$S 418.1925. Found 418.1907.

Example 68

The compound 68 was produced in the same method as Example 45 where 0.13 g of the compound 57 (N-[3-{3-(piperidinomethyl)phenoxy}propyl]-2-(3-furylmethylthio)acetamide was employed.

Compound 68

N-[3-{3-(piperidinomethyl)phenoxy}propyl]-2-(3-furylmethylsulfonyl)acetamide

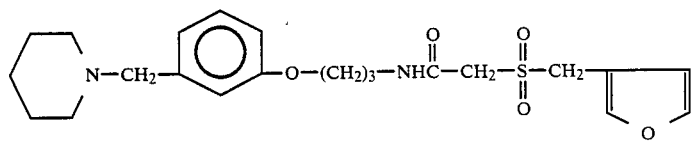

NMR (300 MHz, CDCl$_3$, δ) 1.40-1.50(2H, m), 1.40-1.65(4H, m), 2.04(2H, tt, J=6.1 Hz, 6.1 Hz), 2.35-2.50(4H, m), 3.48(2H, s), 3.52(2H, dt, J=6.1 Hz, 6.1 Hz), 3.76(2H, s), 4.08(2H, t, J=6.1 Hz), 4.29(2H, s), 6.57(1H, d, J=1.1 Hz), 6.75-7.00(3H, m), 6.96(1H, brs), 7.20-7.30(1H, m), 7.45(1H, d, J=1.1 Hz), 7.62(1H, s).

IR (cm$^{-1}$, film, ν) 1670 (C=O), 1670 (C=O), 1320 (S=O), 1120 (S=O).

High Resolution Mass Spectrum Molecular Weight: Calcd. for C$_{22}$H$_{30}$N$_2$O$_5$S 434.1876. Found 434.1884.

m.p. 64.9°-65.7° C.

Example 69

0.72 g (2.9 mmol) of 3-{3-(piperidinomethyl)phenoxy}propylamine and 0.50 g (2.9 mmol) of 2-(furfurylthio)acetic acid were dissolved in 30 ml of dichloromethane, and 0.56 g of EDC was added to this solution. This mixture was stirred overnight, and extraction was carried out by adding 30 ml of dichloromethane and 30 ml of water. The dichloromethane layer was washed with 30 ml of water, and dried over anhydrous magnesium sulfate. The solvent was evaporated in vacuo, and the residue was purified by silica gel column chromatography using methanol:dichloromethane=1:19 as developing solvent to obtain 0.58 g of the oily compound 19 (N-[3-{3-(piperidinomethyl)phenoxy}propyl]-2-(furfurylthio)acetamide).

Examples 70-78

Various compounds were produced in the same method as Example 69 where each 2.9 mmole of the following acetic acids was employed instead of 2-(furfurylthio)acetic acid.

| Acetic Acid | Product |
| --- | --- |
| 2-{1-(2-furyl)ethylthio}acetic acid | Compound 58 |
| 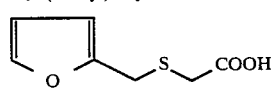 | |
| 2-(3-furyl)methylthioacetic acid | Compound 57 |

| Acetic Acid | Product |
|---|---|
| -continued | |
| 2-(furfurylsulfinyl)acetic acid | Compound 46 |
| 2-(furfurylsulfonyl)acetic acid | Compound 47 |
| 2-(benzylthio)acetic acid | Compound 1 |
| 2-(benzylsulfinyl)acetic acid | Compound 44 |
| 2-(benzylsulfonyl)acetic acid | Compound 45 |
| 2-(4-pyridylmethylthio)acetic acid | Compound 28 |
| 2-(2-thienylthio)acetic acid | Compound 20 |

Example 79

0.40 g of 3-{3-(piperidinomethyl)phenoxy}propylamine and 0.26 g of anhydrous potassium carbonate were dissolved in 10 ml of water, and vigorously stirred under cooling in an ice bath. 2-(Benzoylthio)acetylchloride solution prepared by dissolving 0.38 g of this acetylchloride in 10 ml of dichloromethane was added dropwise to this reaction solution, and stirred for 30 minutes under cooling in an ice bath. The aqueous layer was separated, and extraction was carried out by adding 20 ml of dichloromethane to the aqueous layer. This dichloromethane was combined with the dichloromethane layer, and washed with water. Then, the dichloromethane was dried over anhydrous magnesium sulfate, and the solvent was evaporated. The residue was purified by silica gel column chromatography using a methanol:dichloromethane=1:19 as developing solvent, and 0.48 g of the oily compound 1 was obtained.

Example 80

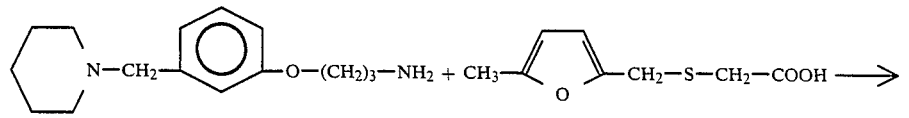

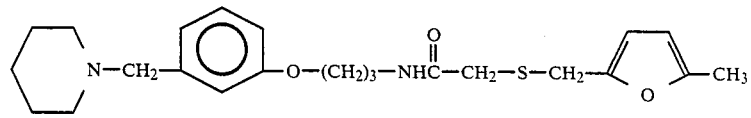

0.40 g of 3-{3-(piperidinomethyl)phenoxy}propylamine was dissolved in 20 ml of dichloromethane, and cooled in an ice bath. 0.30 g of 2-(5-methylfurfurylthio)acetic acid and 0.31 g of EDC were added to this solution and stirred at 0° C. for 30 minutes and further at room temperature overnight. 20 ml of water and 20 ml of dichloromethane were added to the reaction solution, and extraction was carried out. The dichloromethane layer was washed twice with water, and dried by anhydrous magnesium sulfate. The solvent was evaporated, and the residue was purified by silica gel column chromatography to obtain 0.17 g of the following compound 69 as colorless oily material.

Compound 69

N-[3-{3-(piperidinomethyl)phenoxy}propyl]-2-(5-methyl-furfurylthio)acetamide

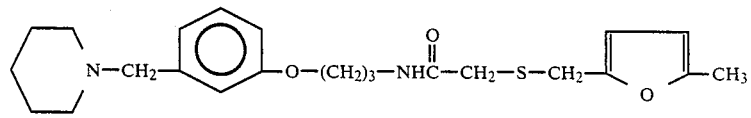

NMR (CDCl$_3$, δ) 1.37–1.66(6H, m), 1.99(2H, tt, J=6.0, 16.0 Hz), 2.25(3H, s), 2.30–2.47(4H, m), 3.24(2H, s), 3.44(2H, s), 3.45(2H, dt, J=6.0, 6.0 Hz), 3.68(2H, s), 4.05(2H, t, J=6.0 Hz), 5.85(1H, d, J=3.0), 6.04(1H, d, J=3.0), 6.77–7.40(5H, m).

IR (cm$^{-1}$, film, ν) 1650 (C=O).

Mass as $C_{23}H_{32}N_2O_3S$: Calculated: 416.2133. Found: 416.2126.

Examples 81-85

The following compounds 70-74 were produced according to the method of Example 80.

Compound 70

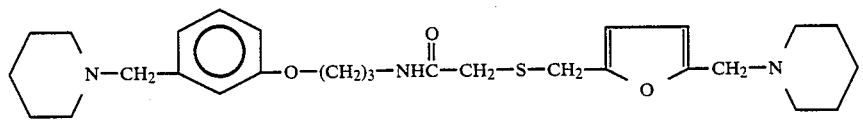

NMR (CDCl$_3$, δ) 1.35-1.70(12H, m), 2.00(2H, tt, J=6.0, 6.0 Hz), 2.27-2.54(8H, m), 3.20(2H, s), 3.45(2H, s), 3.47(2H, s), 3.46(2H, dd, J=6.0, 6.0 Hz), 3.71(2H, s), 4.06(2H, t, J=6.0 Hz), 6.09(1H, d, J=3.5 Hz), 6.11(1H, d, J=3.5 Hz), 6.81(1H, dd, J=7.5, 2.0 Hz), 6.91(1H, d, J=7.5 Hz), 7.21(1H, dd, J=7.5, 7.5 Hz), 6.96(1H, brs), 7.30-7.37(1H, m).

IR (cm$^{-1}$, film, ν) 1650 (C=O).

Mass as $C_{28}H_{41}N_3O_3S$: Calculated: 449.2868. Found: 499.2859.

Compound 71

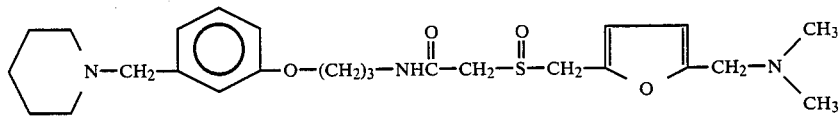

NMR (CDCl$_3$, δ) 1.60-1.90(6H, m), 2.25(2H, tt, J=6.0, 6.0 Hz), 2.46(6H, s), 2.57-2.70(4H, m), 3.57(1H, d, J=14.0 Hz), 3.67(1H, d, J=14.0 Hz), 3.64(2H, s), 3.69(2H, s), 3.72(2H, dd, J=6.0, 6.0 Hz), 4.27(2H, t, J=6.0 Hz), 4.32(1H, d, J=14.0 Hz), 4.42(1H, d, J=14.0 Hz), 6.42(1H, d, J=3.50 Hz), 6.61(1H, d, J=3.50 Hz), 7.00(1H, dd, J=7.50, 2.0 Hz), 7.10(1H, d, J=7.50 Hz), 7.15(1H, brs), 7.39(1H, dd, J=7.50, 7.50 Hz), 7.61(1H, brt, J=6.0 Hz).

IR (cm$^{-1}$, film, ν) 1650 (C=O), 1040 (S—O).

Mass as $C_{25}H_{37}N_3O_3S$: Calculated: 459.2556. Found: 459.2578.

Compound 72

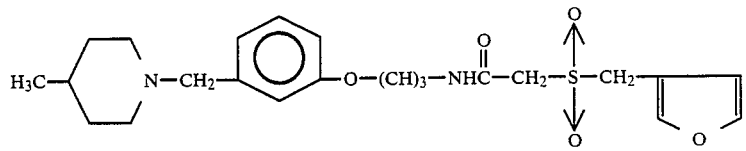

NMR (CDCl$_3$, δ) 0.93(3H, d, 5.5 Hz), 1.20-2.10(8H, m), 2.85-3.00(2H, m), 3.52(2H, dt, 6.0, 6.0 Hz), 3.53(2H, s), 3.79(2H, s), 2.04(2H, tt, 6.0, 6.0 Hz), 4.10(2H, t, 6.0 Hz), 4.30(2H, s), 6.58(1H, d, 1.5 Hz), 6.81(1H, dd, 8.0, 2.0 Hz), 6.89(1H, d, 8.0 Hz), 7.21(1H, dd, 8.0, 8.0 Hz), 7.45(1H, dd, 1.5, 1.5 Hz), 7.63(1H, s).

IR (cm$^{-1}$, ν) 1670 (C=O).

Compound 73

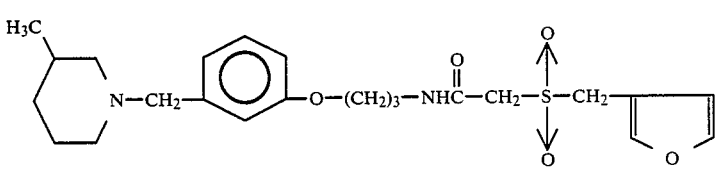

NMR (CDCl$_3$, δ) 0.76(3H, d, 6.5 Hz), 1.76-1.90(1H, m), 1.45-1.70(4H, m), 2.66-2.97(3H, m), 1.74(2H, tt, 6.6 Hz), 3.41(2H, s), 3.71(2H, s), 3.92(2H, dt, 6.0, 6.0 Hz), 3.99(2H, t, 6.0 Hz), 6.50(1H, d, 1.0 Hz), 6.73(1H, dd, 8.0, 2.5 Hz), 6.88(1H, s), 6.81(1H, d, 8.0 Hz), 6.98-7.10(1H, m), 4.23(2H, s), 7.13(1H, dd, 8.0, 8.0 Hz), 7.36(1H, s), 7.55(1H, d, 1.0 Hz), 7.50-8.50(1H, m).

IR (cm$^{-1}$, ν) 1680 (C=O).

Compound 74

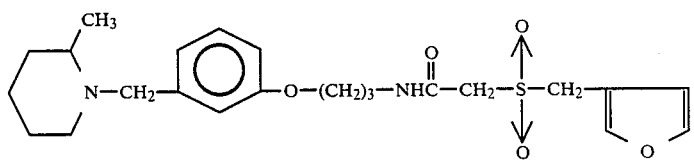

NMR (CDCl$_3$, δ) 1.23(3H, d, 6.5 Hz), 1.15–1.75(6H, m), 1.96–2.15(1H, m), 2.35–2.53(1H, m), 2.03(2H, tt, 6.0, 6.0 Hz), 2.79(1H, dt, 13.5, 4.5 Hz), 3.25(1H, d, 13.5), 3.50(2H, dt, 6.0, 6.0 Hz), 4.06(1H, d, 13.5), 4.09(2H, s), 4.10(2H, t, 6.0 Hz), 4.31(2H, s), 6.57(1H, d, 1.5 Hz), 6.80(1H, dd, 7.5, 1.0 Hz), 6.89(1H, d, 7.5 Hz), 7.04(1H, s), 7.20(1H, dd, 7.5, 7.5 Hz), 7.44(1H, dd, 1.5, 1.5 Hz), 7.62(1H, s), 7.10–7.13(1H, m).

IR (cm$^{-1}$, ν) 1680 (C=O) 1665.

Example 86

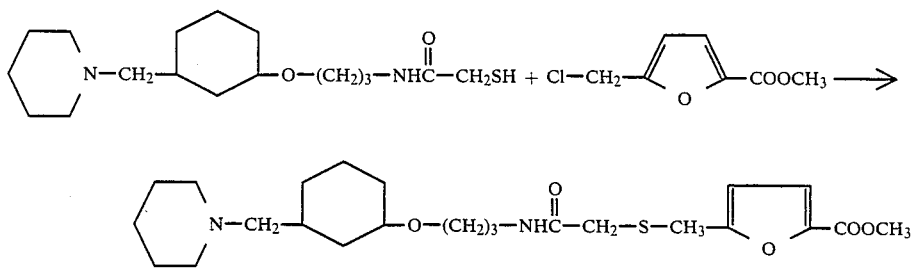

0.70 g of N-[3-{3-(piperidinomethyl)phenoxy}propyl]-2-mercaptoacetamide was dissolved in 10 ml of dimethylformamide, and stirred under cooling in an ice bath. 0.087 g of 60% sodium hydride was added, and stirred for 10 minutes under cooling in an ice bath and further for 10 minutes at room temperature. This reaction solution was cooled in an ice bath again, and the solution prepared by dissolving 0.38 g of methyl-5-chloromethyl-2-furan carboxylate in 5 ml of dimethylformamide was added dropwise. The mixture was stirred for 20 minutes under cooling in an ice bath, and then stirred overnight at room temperature. The product was extracted twice with benzene, and the benzene layer was washed twice with water. The benzene layer was dried over anhydrous magnesium sulfate, and the solvent was evaporated in vacuo. The residue was purified by silica gel column chromatography using methanol:dichloromethane=1:19 as developing solvent, and 0.40 g of the colorless oily compound 75 was obtained.

Compound 75

N-[3-{3-(piperidinomethyl)phenoxy}propyl]-2-{(5-methoxycarbonyl)furfurylthio}acetamide NMR (CDCl$_3$, δ) 1.40–1.65(6H, m), 2.00(2H, tt, J=6.5, 6.5 Hz), 2.30–2.45(4H, m), 3.23(2H, s), 3.44(2H, s), 3.45(2H, dt, J=6.5, 6.5 Hz), 3.77(2H, s), 3.87(3H, s), 4.05(2H, t, J=6.5 Hz), 6.33(1H, d, J=3.5 Hz), 6.97(1H, d, J=3.5 Hz), 6.80–7.30(5H, m).

IR (cm$^{-1}$, film, ν) 1650 (C=O), 1730 (C=O).

Mass as C$_{24}$H$_{32}$N$_2$O$_5$S: Calculated: 460.2032. Found: 460.2041.

Example 87

The following compound 76 was produced according to the method of Example 86.

Compound 76

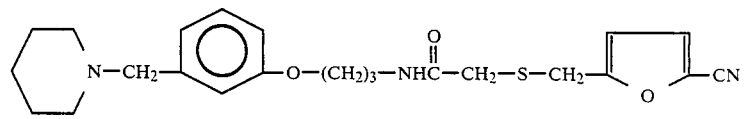

NMR (CDCl$_3$, δ) 1.37–1.50(6H, m), 2.02(2H, tt, J=6.0, 6.0 Hz), 2.28–2.53(4H, m), 3.22(2H, s), 3.47(2H, dt, J=6.0, 6.0 Hz), 3.49(2H, s), 3.77(2H, s), 4.10(2H, t, J=6.0 Hz), 6.34(1H, d, J=3.50), 6.84(1H, d, J=7.5 Hz), 6.93(1H, d, J=7.5 Hz), 6.98(1H, s), 7.01(1H, d, J=3.50 Hz), 7.13–7.21(1H, m), 7.23(1H, dd, J=7.5, 7.5 Hz).

IR (cm$^{-1}$, film, ν) 2225 (C≡N), 1650 (C=O).

Mass as C$_{23}$H$_{29}$N$_3$O$_3$P: Calculated: 427.1930. Found: 427.1934.

Example 88

510 mg of the compound 69 obtained in Example 80 was dissolved in 10 ml of methanol, and 3 ml of water and 88 mg of 85% potassium hydroxide were added to this. The solution was stirred for 7 hours at room temperature, and after the reaction, it was neutralized with 2N aqueous hydrochloric acid. Water and methanol were evaporated under reduced pressure. 100 ml of dichloromethane and anhydrous magnesium sulfate was added to the residue, and stirred for one hour at room temperature. Insoluble residue was filtered off, and solvent was evaporated from the filtrate to obtain 490 mg of the following compound 77.

Compound 77

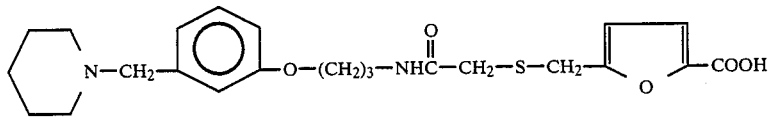

NMR (CDCl$_3$, δ) 1.70-2.20(6H, m), 1.77(2H, tt, J=6.5, 6.5 Hz), 2.40-2.70(2H, m), 3.23(2H, td, J=6.5, 6.5 Hz), 3.65-3.80(2H, m), 3.76(2H, s), 3.86(2H, t, J=6.5 Hz), 4.09(2H, s), 6.23(1H, d, J=3.0 Hz), 6.75-7.50(6H, m).

IR (cm$^{-1}$, film, ν) 1650 (C=O), 1710 (C=O).

Mass as C$_{23}$H$_{30}$O$_5$S: Calculated: 446.1875. Found: 446.1884.

Example 89

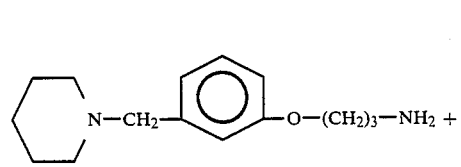

630 mg of 3-{3-(1-piperidinomethyl)phenoxy}propylamine and 600 mg of 2-(4-methyl-2-pyridylmethylthio)acetic acid were dissolved in 40 ml of dichloromethane, and cooled in an ice bath. 530 mg of EDC was added, and stirred at room temperature for 18 hours. This reaction solution was washed three times with water, and dried over anhydrous magnesium sulfate. The solvent was evaporated, and the residue was purified by silica gel column chromatography using methanol:chloroform=1:9 as developing solvent to obtain 1.125 g of the compound 78.

Compound 78

N-[3-{3-(piperidinomethyl)phenoxy}propyl](4-methyl-2-pyridylmethylthio)acetamide NMR (CDCl$_3$, δ) 1.40-1.65(6H, m), 2.02(2H, tt, J=6.0 Hz, 6.0 Hz), 2.32(3H, s), 2.30-2.45(4H, m), 3.15(2H, s), 3.43(2H, s), 3.47(2H, dt, J=6.0 Hz, 6.0 Hz), 3.80(2H, s), 4.05(2H, t, J=6.0 Hz), 6.79(1H, dd, J=8.0 Hz, 1.5 Hz), 6.90(1H, d, J=8.0 Hz), 6.91(1H, s), 6.98(1H, d, J=4.5 Hz), 7.09(1H, s), 7.20(1H, t, J=8.0 Hz), 7.82(1H, brs), 8.31(1H, d, J=4.5 Hz).

IR (cm$^{-1}$, film, ν) 1670 (C=O).

Mass as C$_{24}$H$_{33}$N$_3$O$_2$S: Calculated: 427.2293. Found: 427.2264.

Examples 90-92

The compounds 79-81 were produced according to the method of Example 89.

Compound 79

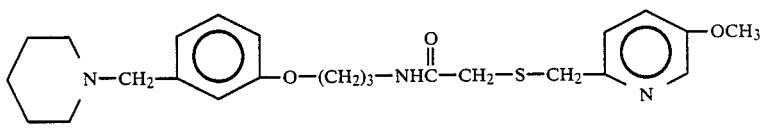

NMR (CDCl$_3$, δ) 1.40-1.65(6H, m), 2.02(2H, tt, J=6.0 Hz), 2.30-2.45(4H, m), 3.15(2H, s), 3.43(2H, s), 3.45(2H, dt, J=6.0, 6.0 Hz), 3.80(2H, s), 3.82(3H, s), 4.06(2H, t, J=6.0 Hz), 6.80(1H, d, J=8.3 Hz), 6.90(1H, d, J=8.3 Hz), 6.92(1H, s), 7.13-7.23(3H, m), 7.66(1H, brs), 8.17(1H, d, J=3.0 Hz).

IR (cm$^{-1}$, film, ν) 1640 (C=O).

Mass as C$_{24}$H$_{33}$N$_3$O$_3$S: Calculated: 443.2242. Found: 443.2224.

Compound 80

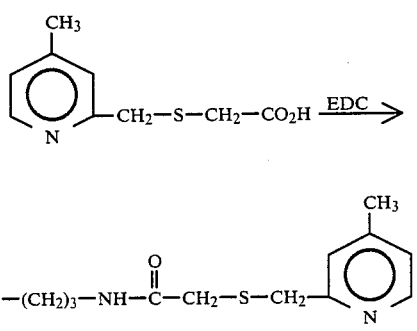

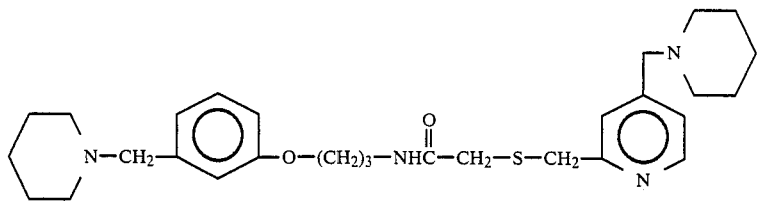

NMR (CDCl$_3$, δ) 1.40–1.65(12H, m), 2.02(2H, tt, J=6.0 Hz, 6.0 Hz), 2.30–2.45(8H, m), 3.17(2H, s), 3.42(2H, s), 3.44(2H, s), 3.46(2H, dt, J=6.0 Hz, 6.0 Hz), 3.83(2H, s), 4.06(2H, t, J=6.0 hz), 6.80(1H, d, J=8.0 Hz), 6.90(1H, d, J=8.0 Hz), 6.93(1H, s), 7.15(1H, d, J=5.5 Hz), 7.20(1H, t, J=8.0 Hz), 7.25(1H, s), 7.87(1H, brs), 8.37(1H, d, J=5.5 Hz).

IR (cm$^{-1}$, film, ν) 1650 (C=O).

Mass as C$_{29}$H$_{42}$N$_4$O$_2$S: Calculated: 510.3028. Found: 510.3015.

Compound 81

190 mg of this chloromethylpyridine in 6 ml of dimethylformamide was added dropwise to the solution, and stirred for 90 minutes. The reaction solution was poured on 60 g of ice, and extraction was carried out three times with each 20 ml of benzene. The benzene layer was washed three times with water, and dried over anhydrous sodium sulfate. The solvent was evaporated, and the residue was purified by silica gel column chromatography using methanol:chloroform=1:9 as developing solvent to obtain 220 mg of the compound 82.

Compound 82

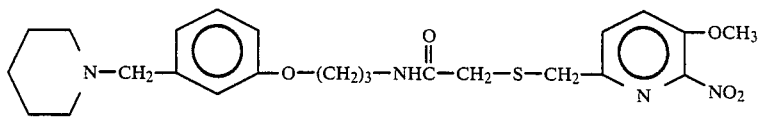

NMR (CDCl$_3$, δ) 1.40–1.65(6H, m), 2.03(2H, tt, J=6.0 Hz, 6.0 Hz), 2.30–2.45(4H, m), 3.15(2H, s), 3.44(2H, s), 3.49(2H, dt, J=6.0 Hz, 6.0 Hz), 3.79(2H, s), 3.97(2H, s), 4.05(2H, t, J=6.0 Hz), 6.77(1H, d, J=7.5 Hz), 6.89(1H, d, J=7.5 Hz), 6.91(1H, s), 7.20(1H, t, J=7.5 Hz), 7.27(1H, brs), 7.48(1H, d, J=8.0 Hz), 7.54(1H, d, J=8.0 Hz).

IR (cm$^{-1}$, film, ν) 1660 (C=O).

Mass as C$_{24}$H$_{32}$N$_4$O$_5$S: Calculated: 488.2093. Found: 488.2099.

Example 93

N-[3-{3-(piperidinomethyl)phenoxy}propyl]-2-(6-chloro-2-pyridylmethylthio)acetamide NMR (CDCl$_3$, δ) 1.40–1.65(6H, m), 2.03(2H, tt, J=6.0 Hz, 6.0 Hz), 2.30–2.45(4H, m), 3.19(2H, s), 3.43(2H, s), 3.48(2H, dt, J=6.0 Hz, 6.0 Hz), 3.79(2H, s), 4.06(2H, t, J=6.0 Hz), 6.79(1H, d, J=8.0 Hz), 6.90(1H, d, J=8.0 Hz), 6.91(1H, s), 7.17–7.23(3H, m), 7.44(1H, brs), 7.61(1H, t, J=8.0 Hz).

IR (cm$^{-1}$, film, ν) 1680 (C=O).

Mass as C$_{23}$H$_{30}$N$_3$O$_2$SCl: Calculated: 447.1547. Found: 447.1573.

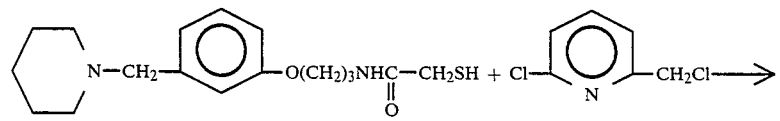

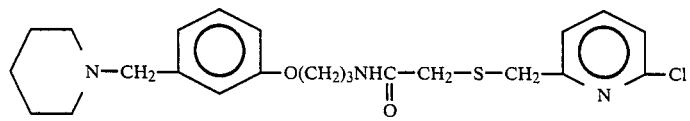

470 mg of N-[3-{3-(piperidinomethyl)phenoxy}propyl]-2-mercaptoacetamide was dissolved in 9 ml of dimethylformamide, 60 mg of sodium hydride was added to the solution at 0° C. under a nitrogen atmosphere, and stirred for 15 minutes. 2-Chloro-6-chloromethylpyridine solution prepared by dissolving Examples 94–98

The compounds 83–87 were produced according to the method of Example 93.

Compound 83

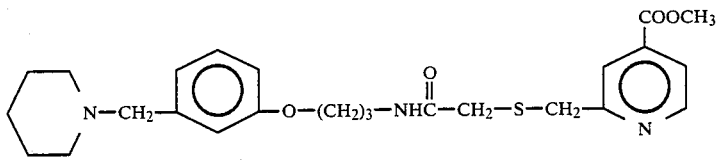

NMR (CDCl$_3$, δ) 1.40–1.70(6H, m), 2.02(2H, tt, J=6.0 Hz, 6.0 Hz), 2.30–2.45(4H, m), 3.19(2H, s), 3.44(2H, s), 3.45(2H, dt, J=6.0 Hz, 6.0 Hz), 3.91(2H, s), 3.94(3H, s), 4.06(2H, t, J=6.0 Hz), 6.79(1H, d, J=8.5 Hz), 6.90(1H, d, J=8.5 Hz), 6.92(1H, s), 7.20(1H, t, J=8.5 Hz), 7.54(1H, brs), 7.72(1H, d, J=5.0 Hz), 7.85(1H, s), 8.62(1H, d, J=5.0 Hz).

IR (cm$^{-1}$, film, ν) 1730 (C=O), 1660 (C=O).

Mass as C$_{25}$H$_{33}$N$_3$O$_4$S: Calculated: 471.2191. Found: 471.2186.

Compound 84

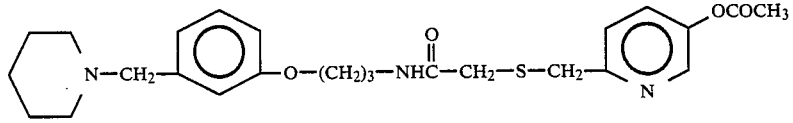

NMR (CDCl$_3$, δ) 1.40–1.65(6H, m), 2.00(2H, tt, J=6.0 Hz, 6.0 Hz), 2.32(3H, s), 2.30–2.45(4H, m), 3.19(2H, s), 3.45(2H, s), 3.46(2H, dt, J=6.0 Hz, 6.0 Hz), 3.84(2H, s), 4.05(2H, t, J=6.0 Hz), 6.81(1H, d, J=8.0 Hz), 6.90(1H, d, J=8.0 Hz), 6.93(1H, s), 7.21(1H, t, J=8.0 Hz), 7.29(1H, d, J=8.5 Hz), 7.43(1H, dd, J=2.0 Hz, 8.5 Hz), 7.53(1H, brs), 8.27(1H, d, J=2.0 Hz).

IR (cm$^{-1}$, film, ν) 1770 (C=O), 1660 (C=O).

Mass as C$_{25}$H$_{33}$N$_3$O$_4$S: Calculated: 471.2191. Found: 471.2174.

Compound 85

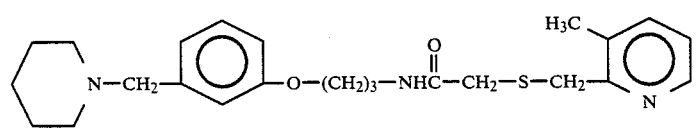

NMR (CDCl$_3$, δ) 1.40–1.65(6H, m), 2.05(2H, tt, J=6.0 Hz, 6.0 Hz), 2.37(3H, s), 2.30–2.45(4H, m), 3.08(2H, s), 3.42(2H, s), 3.50(2H, dt, J=6.0 Hz, 6.0 Hz), 3.87(2H, s), 4.07(2H, t, J=6.0 Hz), 6.79(1H, d, J=8.0 Hz), 6.90(1H, d, J=9.0 Hz), 6.91(1H, s), 7.10(1H, dd, J=7.8 Hz, 5.0 Hz), 7.20(1H, t, J=8.0 Hz), 7.48(1H, d, J=5.0 Hz), 8.02(1H, brs), 8.26(1H, d, J=5.0 Hz).

IR (cm$^{-1}$, film, ν) 1660 (C=O).

Mass as C$_{24}$H$_{33}$N$_3$O$_2$S: Calculated: 427.2293. Found: 427.2292.

Compound 86

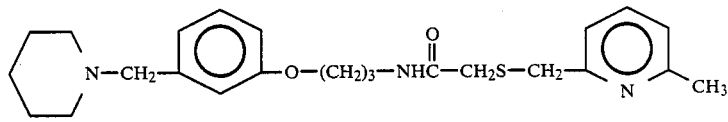

NMR (CDCl$_3$, δ) 1.40–1.65(6H, m), 2.02(2H, tt, J=6.0 Hz, 6.0 Hz), 2.30–2.45(4H, m), 2.50(3H, s), 3.15(2H, s), 3.43(2H, s), 3.47(2H, dt, J=6.0 Hz, 6.0 Hz), 3.80(2H, s), 4.05(2H, t, J=6.0 Hz), 6.79(1H, dd, J=7.4 Hz, 2.0 Hz), 6.90(1H, d, J=7.4 Hz), 6.91(1h, s), 7.03(1H, d, J=7.5 Hz), 7.08(1H, d, J=7.5 Hz), 7.20(1H, t, J=7.4 Hz), 7.55(1H, t, J=7.5 Hz), 7.89(1H, brs).

IR (cm$^{-1}$, film, ν) 1670 (C=O).

Mass as C$_{24}$H$_{33}$N$_3$O$_2$S: Calculated: 427.2293. Found: 427.2301.

Compound 87

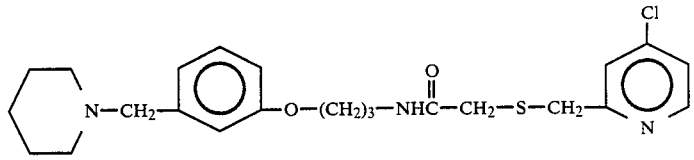

NMR (CDCl$_3$, δ) 1.40–1.65(6H, m), 2.02(2H, tt, J=6.0 Hz, 6.0 Hz), 2.30–2.45(4H, m), 3.20(2H, s), 3.47(2H, s), 3.49(2H, dt, J=6.0 Hz, 6.0 Hz), 3.90(2H, s), 4.08(2H, t, J=6.0 Hz), 6.81(1H, d, J=7.5 Hz), 6.91(1H, d, J=7.5 Hz), 6.97(1H, s), 7.21(1H, t, J=7.5 Hz), 7.36(1H, brs), 7.38(1h, d, J=5.5 Hz), 7.55(1H, brs), 8.66(1H, d, J=5.5 Hz).

IR (cm$^{-1}$, film, ν) 2230 (C≡N), 1660 (C=O).

Mass as $C_{24}H_{30}N_4O_2S$: Calculated: 438.2099. Found: 438.2104.

Example 99

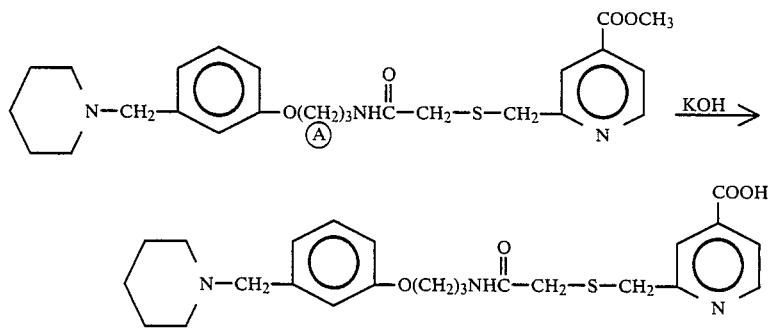

0.22 g of the compound (A) was dissolved in a mixed solvent of 30 ml of methanol and 10 ml of water. 0.04 g of potassium hydroxide was added, and stirred at room temperature for 2 hours. The pH of the reaction solution was adjusted to 7 by adding 5% aqueous hydrochloric acid, and then, water and methanol were evaporated under reduced pressure. 5% methanol-dichloromethane was added to the residue, and stirred. Insoluble materials were removed by filtration, and the solvent was evaporated from the filtrate in vacuo. The residue was purified by silica gel column chromatography using methanol:dichloromethane=15:85 as developing solvent, and 0.20 g of the captioned glassy compound 88 was obtained.

Compound 88

NMR (CDCl$_3$, δ) 1.52(2H, tt, J=6.0 Hz, 6.0 Hz), 1.70-2.20(4H, m), 2.50-2.60(2H, m), 3.12(2H, dt, J=6.0 Hz, 6.0 Hz), 3.45(2H, s), 3.51(2H, t, J=6.0 Hz), 3.60-3.80(2H, m), 3.87(2H, s), 4.09(2H, s), 6.53(1H, brs), 6.79(1H, d, J=7.5 Hz), 6.90(1H, d, J=7.5 Hz), 7.21(1H, t, J=7.5 Hz), 7.25(1H, s), 7.83(1H, d, J=5.0 Hz), 7.96(1H, s), 8.59(1H, d, J=5.0 Hz).

IR (cm$^{-1}$, KBr, ν) 1660 (C=O).

Mass as $C_{24}H_{31}N_3O_4S$: Calculated: 457.2034. Found: 457.2033.

Example 100

(furfurylthio)acetic acid were dissolved in 20 ml of dichloromethane, and cooled in an ice bath. 470 mg (2,477 mmole) of EDC was added to this solution, and stirred at 0° C. for 30 minutes then at room temperature overnight. 20 ml of water and 20 ml of dichloromethane were added to the reaction solution, and organic layer was separated, washed twice with water, and dried over anhydrous magnesium sulfate. The solvent was evaporated in vacuo, and the residue was purified by silica gel column chromatography to obtain 910 mg (90%) of the captioned compound 89.

Compound 89

N-[2-{-(piperidinomethyl)furfurylthio)ethyl]-2-{(furfurylthio)acetamide

NMR (CDCl$_3$, δ) 1.36-1.76(6H, m), 2.32-2.46(4H, m), 2.64(2H, t, J=6.50), 3.21(2H, s), 3.37(2H, dt, J=6.50, 6.50), 3.47(2H, s), 3.72(2H, s), 3.77(2H, s), 6.11(1H, d, J=3.0 Hz), 6.14(1H, d, J=3.0 Hz), 6.22(1H, d, J=3.50), 6.30(1H, dd, J=3.50, 2.0 Hz), 7.03-7.10(1H, m), 7.36(1H, d, J=2.0 Hz).

IR (cm$^{-1}$, film, ν) 1650 (C=O).

Mass as $C_{20}H_{28}N_2O_3S_2$: Calculated: 408.1542. Found: 408.1557.

Examples 101-114

The following compounds 90-103, 104-4 and 104-3 were produced according to the method of Example 100.

Compound 90

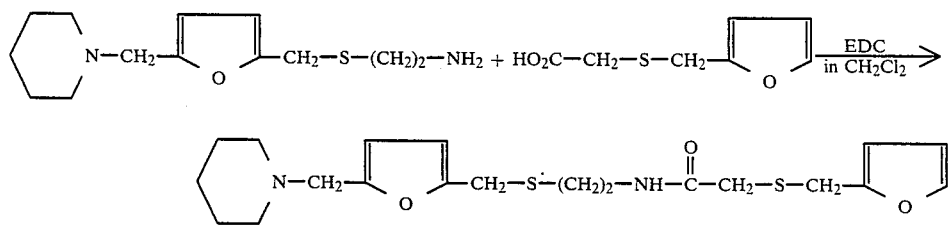

630 mg (2,477 mmole) of 2-{5-(piperidinomethyl)furfurylthio}ethylamine and 430 mg (2,477 mmole) of 2-

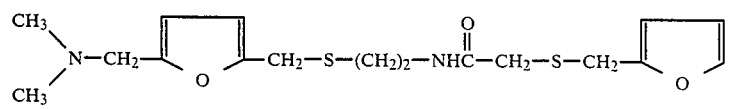

NMR (CDCl₃, δ) 2.25(6H, s), 2.64(2H, t, J=6.50), 3.20(2H, s), 3.35(2H, dt, J=6.50, 6.50), 3.43(2H, s), 3.72(2H, s), 3.78(2H, s), 6.13(1H, d, J=3.50), 6.15(1H, d, J=3.50), 6.22(1H, d, J=3.50), 6.30(1H, dd, J=3.50, 2.00), 7.05–7.15(1H, m), 7.36(1H, d, J=2.00).

IR (cm⁻¹, film, ν) 1665 (C=O).

Mass as C₁₇H₂₄N₂O₃S₂: Calculated: 368.1227. Found: 368.1216.

Compound 91

NMR (CDCl₃, δ) 2.25(6H, s), 2.63–2.78(2H, m), 3.33(1H, d, J=14.5 Hz), 3.41(2H, s), 3.30–3.51(2H, m), 3.60(1H, d, J=14.5 Hz), 3.73(2H, s), 4.21(1H, d, J=14.5 Hz), 4.32(1H, d, J=14.5 Hz), 6.12(1H, d, J=3.0), 6.14(1H, d, J=3.0), 6.39(1H, dd, J=3.50, 2.0 Hz), 6.48(1H, d, J=3.5 Hz), 7.45(1H, d, J=2.0 Hz), 1.75–1.14(1H, m).

IR (cm⁻¹, film, ν) 1660 (C=O), 1030 (S—O).

Mass as C₁₇H₂₄N₂O₄S₂: Calculated: 384.1178. Found: 384.1187.

Compound 93

NMR (CDCl₃, δ) 1.75–1.88(4H, m), 2.50–2.61(4H, m), 2.62(2H, t, J=6.5 Hz), 3.20(2H, s), 3.22(2H, d, J=7.0 Hz), 3.37(2H, dd, J=6.5, 6.5 Hz), 3.76(2H, s), 3.87(2H, s), 6.09(1H, dt, J=15.5, 7.0 Hz), 6.20(1H, d, J=3.0), 6.29(1H, dd, J=3.0, 2.0), 6.59(1H, d, J=15.5), 6.72(1H, d, J=3.5 Hz), 6.78(1H, d, J=3.5 Hz), 6.96–7.05(1H, m), 7.34(1H, d, J=2.0).

IR (cm⁻¹, film, ν) 1650 (C=O).

Mass as C₂₁H₂₈N₂O₂S₃: Calculated: 436.1312. Found: 436.1240.

Compound 94

NMR (CDCl₃, δ) 1.36–1.73(6H, m), 2.37–2.54(4H, m), 2.63(2H, t, J=6.5 Hz), 3.21(2H, s), 3.38(2H, dt, 6.5, 6.5 Hz), 3.66(2H, s), 3.77(2H, s), 3.89(2H, s), 6.21(1H, d, J=3.50), 6.30(1H, dd, J=3.50, 2.00), 6.72(1H, d, J=3.50), 6.78(1H, d, J=3.50), 6.96–7.08(1H, m), 7.35(1H, d, J=2.00).

IR (cm⁻¹, film, ν) 1660 (C=O).

Mass as C₂₀N₂₈N₂O₂S₃: Calculated: 424.1313. Found: 424.1310.

Compound 95

NMR (CDCl₃, δ) 1.40–1.50(2H), 1.50–1.70(4H), 2.40–2.60(4H), 2.65(2H, t, J=6.5 Hz), 3.21(2H, s), 3.42(2H, q, J=6.5 Hz), 3.77(2H×2, s), 3.83(2H, s), 6.21(1H, d, J=3.5 Hz), 6.29(1H, dd, J=2.0 and 3.5 Hz), 7.08(1H), 7.15–7.25(1H), 7.35(1H, d, J=2.0 Hz).

IR (cm⁻¹, film, ν) 1660 (C=O).

Mass as C₁₉H₂₇N₃O₂S₃: Calculated: 425.1266. Found: 425.1272.

Compound 96

NMR (CDCl₃, δ) 2.65(2H, t, J=6.5 Hz), 3.20(2H, s), 3.43(2H, dt, J=6.5, 6.5 Hz), 3.77(2H, s), 3.86(2H, s), 6.21(1H, d, J=3.5 Hz), 6.27(1H, dd, J=3.5, 2.0), 7.19(1H, ddd, J=7.5, 4.50, 1.0), 7.35(1H, d, J=2.00), 7.36(1H, d, J=7.5 Hz), 7.67(1H, td, J=7.5, 2.0 Hz), 8.55(1H, d, J=4.50).

IR (cm⁻¹, film, ν) 1650 (C=O).

Mass as C₁₅H₁₈N₂O₂S₂: Calculated: 322.0809. Found: 322.0808.

Compound 97

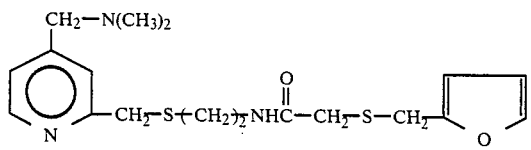

NMR (CDCl₃, δ) 2.25(6H, s), 2.66(2H, t, J=6.5 Hz), 3.20(2H, s), 3.42(2H, s), 3.44(2H, dt, J=6.5 Hz, 6.5 Hz), 3.77(2H, s), 3.85(2H, s), 6.21(1H, d, J=2.5 Hz), 6.30(1H, dd, J=2.5 Hz, 3.5 Hz), 7.15(1H, d, J=4.9 Hz), 7.25(1H, s), 7.35(1H, d, J=3.5 Hz), 8.47(1H, d, J=5.0 Hz).

IR (cm⁻¹, film, ν) 1660 (C=O).

Mass as $C_{18}H_{25}N_3O_2S_2$: Calculated: 379.1389. Found: 379.1391.

Compound 98

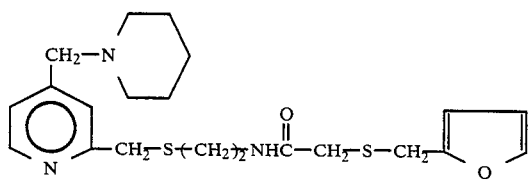

NMR (CDCl₃, δ) 1.40-1.50(2H, m), 1.50-1.65(4H, m), 2.30-2.45(4H, m), 2.66(2H, t, J=6.5 Hz), 3.20(2H, s), 3.44(2H, dt, J=6.5 Hz, 6.5 Hz), 3.45(2H, s), 3.77(2H, s), 3.84(2H, s), 6.21(1H, d, J=3.5 Hz), 6.29(1H, dd, J=3.5 Hz, 2.5 Hz), 7.17(1H, d, J=5.0 Hz), 7.31(1H, s), 7.35(1H, d, J=2.5 Hz), 8.45(1H, d, J=5.0 Hz).

IR (cm⁻¹, film, ν) 1660 (C=O).

Mass as $C_{21}H_{29}N_3O_2S_2$: Calculated: 419.1701. Found: 419.1711.

Compound 99

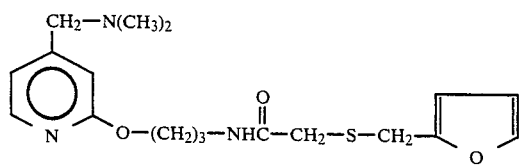

NMR (CDCl₃, δ) 1.96(2H, tt, J=6.5 Hz, 6.5 Hz), 3.24(2H, s), 3.38(2H, s), 3.39(2H, t, d, J=6.5 Hz, 6.5 Hz), 3.75(2H, s), 4.39(2H, t, J=6.5 Hz), 6.19(1H, d, J=1.5 Hz), 6.28(1H, dd, J=1.5 Hz), 6.75(1H, s), 6.89(1H, d, J=6.0 Hz), 7.30(1H, d, J=1.5 Hz), 8.09(1H, d, J=6.6 Hz).

IR (cm⁻¹, film, ν) 1660 (C=O).

Mass as $C_{18}H_{25}N_3O_3S$: Calculated: 363.1616. Found: 363.1600.

Compound 100

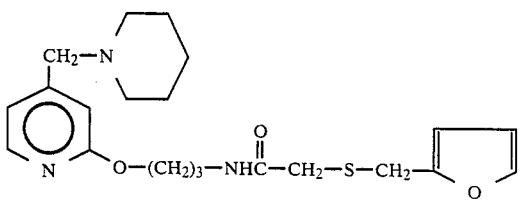

NMR (CDCl₃, δ) 1.40-1.50(2H, m), 1.50-1.65(4H, m), 1.90-2.05(4H, m), 1.96(2H, tt, J=6.5 Hz, 6.5 Hz), 2.30-2.45(4H, m), 3.24(2H, s), 3.39(2H, t, d, J=6.5 Hz, 6.5 Hz), 3.41(2H, s), 3.75(2H, s), 4.39(2H, t, J=6.5 Hz), 6.19(1H, d, J=3.0 Hz), 6.28(1H, dd, J=3.0 Hz, 2.0 Hz), 6.78(1H, s), 6.89(1H, d, J=5.5 Hz), 7.33(1H, d, J=2.0 Hz), 8.07(1H, d, J=5.5 Hz).

IR (cm⁻¹, film, ν) 1660 (C=O).

Mass as $C_{21}H_{29}N_3O_3S$: Calculated: 403.1929. Found: 403.1915.

Compound 101

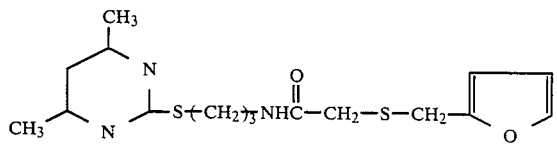

NMR (CDCl₃, δ) 1.93(2H, t, J=6.5 Hz), 2.41(3H×2, s), 3.17(2H, t, J=6.5 Hz), 3.22(2H, s), 3.35(2H, q, J=6.5 Hz), 3.76(2H, s), 6.21(1H, d, J=3 Hz), 6.30(1H, dd, J=2 and 3 Hz), 6.70(1H, s), 6.80-7.00(1H), 7.35(1H, d, J=2 Hz).

IR (cm⁻¹, film, ν) 1650 (C=O).

Mass as $C_{16}H_{21}N_3O_2S_2$: Calculated: 351.1078. Found: 351.1076.

Compound 102

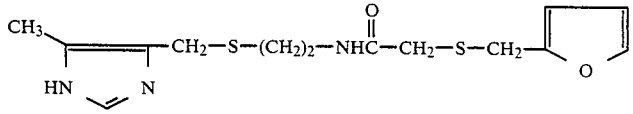

NMR (CDCl₃, δ) 2.23(3H, s), 2.61(2H, t, J=6.5 Hz), 3.22(2H, s), 3.43(2H, d, iJ=6.5 Hz), 3.73(2H, s), 3.78(2H, s), 6.20(1H, d, J=3.5 Hz), 6.28(1H, dd, J=3.5, 20 Hz), 7.34(1H, d, J=2.0 Hz), 7.55(1H, brs).

IR (cm⁻¹, film, ν) 1650 (C=O).

Mass as $C_{14}H_{19}N_3O_2S_2$: Calculated: 325.0918. Found: 325.0905.

Compound 103

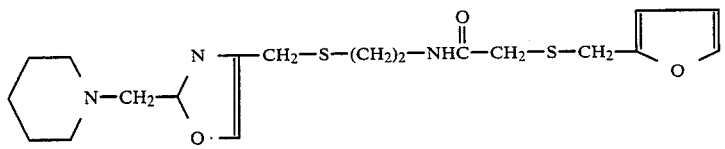

NMR (CDCl₃, δ) 1.40–1.50(2H, m), 1.55–1.65(4H, m), 2.40–2.50(4H, m), 2.67(2H, t, J=6.5 Hz), 3.22(2H, s), 3.44(2H, dt, J=6.5 Hz, 6.5 Hz), 3.63 (2H, s), 3.64(2H, s), 3.78(2H, s), 6.21(1H, d, J=3 Hz), 6.29(1H, dd, J=3.0 Hz, 20 Hz), 7.18(1H, brs), 7.36(1H, d, J=20 Hz), 7.54(1H, s).

IR (cm⁻¹, film, ν) 1660 (C=O).

Mass as $C_{19}H_{27}N_3O_3O_2$: Calculated: 409.1493. Found: 409.1482.

Compound 104-2

0.49 g of 2-guanidino-4-chloromethylthiazole, 0.50 g of the above disulfide and 0.36 g of potassium iodide were dissolved in 20 ml of dry dimethylformamide, and cooled to −15° to −18° C. 0.13 g of 60% sodium hydride was added in an atmosphere of nitrogen gas, and stirred at −15° to −18° C. for 10 hours then at 60° C. for 1 hour. Dimethylformamide was evaporated under reduced pressure, and the residue was purified by silica gel chromatography to obtain 0.58 g (70%) of the captioned compound 104.

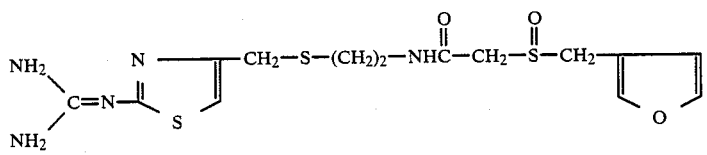

NMR (CDCl₃, δ) 2.67(2H, t, 7.0 Hz), 3.44(2H, dt, 7.0, 3.5 Hz), 3.52(1H, d, 13.0 Hz), 3.63(1H, d, 13.0 Hz), 4.00(1H, d, 14.0 Hz), 4.17(1H, d, 14.0 Hz), 3.69(2H, s), 3.50(5H, brs), 6.51(1H, s), 6.49(1H, d, 1.0 Hz), 7.50(1H, dd, 1.0, 1.0 Hz), 7.58(1H, d, 1.0 Hz).

IR (cm⁻¹, ν) 1655 (C=O).

Compound 104-3

Compound 104

NMR (CDCl₃, δ) 2.63(2H, t, J=7.0 Hz), 3.15(2H, s), 3.41(2Ht, J=7.0 Hz), 3.43(2H, s), 3.74(2H, s), 3.66(5H, brs), 6.82(1H, s), 6.40(1H, brs), 7.37–7.40(2H, m).

IR (cm⁻¹, film, ν) 1603.

Mass as $C_{14}H_{19}N_5O_2S_3$: Calculated: 385.0701. Found: 385.0714.

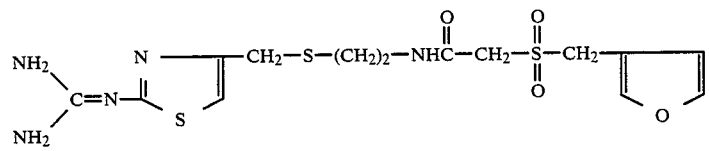

NMR (CDCl₃, δ) 2.48(5H, brs), 2.71(2H, t, 6.5 Hz), 3.44(2H, dt, 6.5, 6.5 Hz), 3.67(2H, s), 3.44(2H, s), 4.38(2H, s), 6.45 (1H, s), 6.58(1H, dd, 1.0, 1.0 Hz), 7.46(1H, dd, 1.0, 1.0 Hz), 7.64(1H, d, 1.0 Hz).

IR (cm⁻¹, ν) 1655 (C=O), 1615.

Example 115

Examples 116–121

The compounds 105–110 were produced according to the method of Example 115.

Compound 105

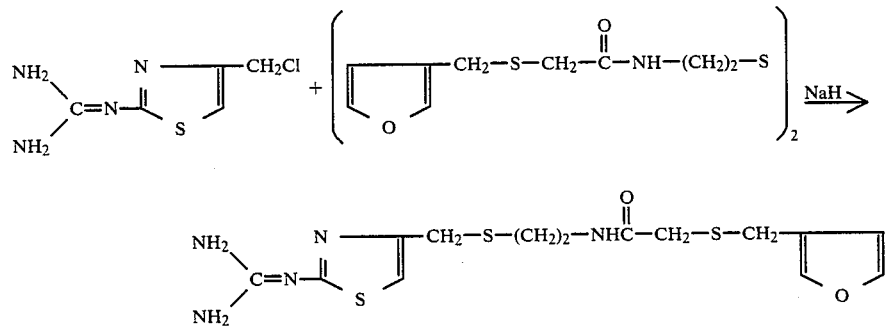

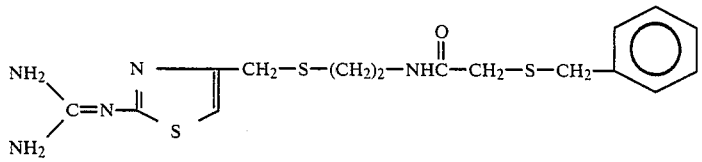

NMR (CDCl$_3$, δ) 2.64(2H, t, J=6.5 Hz), 3.13(2H, s), 3.37(2H, dt, J=6.5, 6.5 Hz), 3.67(2H, s), 3.74(2H, s), 5.93(4H, brs), 6.47(1H, s), 6.97–7.07(1H, m), 7.24–7.37(5H, m).

IR (cm$^{-1}$, KBr, ν) 1650 (C=O).

Mass as C$_{16}$H$_{21}$N$_5$OS$_3$: Calculated: 395.0908. Found: 395.0919.

Compound 106

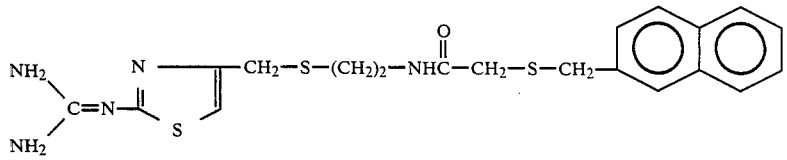

Mass as C$_{16}$H$_{27}$N$_5$OS$_3$: Calculated: 401.1377. Found: 401.1356.

Compound 108

NMR (CDCl$_3$, δ) 2.54(2H, t, J=7.0 Hz), 3.27(2H, t, J=7.0 Hz), 3.11(2H, s), 3.74(2H, s), 3.96(2H, s), 4.84(5H, brs), 6.91(1H, s), 7.43–7.56(3H, m), 7.72–7.90(4H, m).

IR (cm$^{-1}$, KBr, ν) 1615.

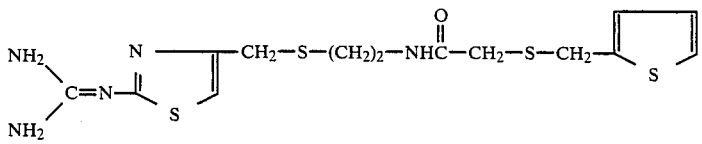

NMR (CDCl$_3$, δ) 2.62(2H, t, J=6.5 Hz), 3.20(2H, s), 3.37(2H, s), 3.43(2H, t, J=6.5 Hz), 3.75(2H, s), 4.04(5H, brs), 6.86(1H, s), 6.90–7.00(2H, m), 7.34(1H, dd, J=5.0, 1.0 Hz).

IR (cm$^{-1}$, KBr, ν) 1685, 1615.

Mass as C$_{14}$H$_{19}$N$_5$OS$_4$: Calculated: 401.0473. Found: 401.0473.

Compound 107

Mass as C$_{20}$H$_{23}$N$_5$OS$_3$ Calculated: 445.1064 Found: 445.1043

Compound 109

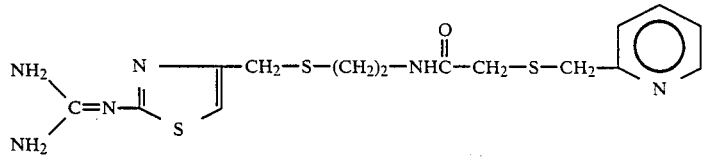

NMR (CDCl$_3$, δ) 2.64(2H, t, J=6.5 Hz), 3.15(2H, s), 3.38(2H, t, J=6.5 Hz), 3.80(2H, s), 3.92(2H, s), 4.85(5H, brs), 7.05(1H, s), 7.31(1H, ddd, J=7.5, 5.0, 1.0 Hz), 7.47(1H, d, J=7.5 Hz), 7.80(1H, ddd, J=7.5, 7.5, 1.5 Hz), 8.47(1H, dd, J=5.0, 1.5 Hz).

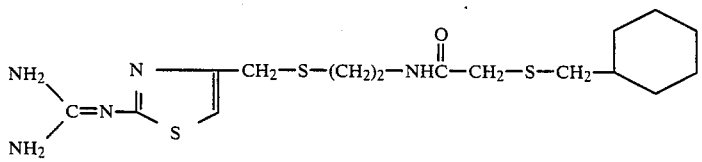

NMR (CDCl$_3$, δ) 0.87–1.88(11H, m), 2.45(2H, d, J=7.0 Hz), 2.66(2H, t, J=6.5 Hz), 3.20(2H, s), 3.46(2H, t, J=6.5 Hz), 3.74(2H, s), 3.59(5H, brs), 6.79(1H, s).

IR (cm$^{-1}$, KBr, ν) 1690, 1618.

IR (cm$^{-1}$, KBr, ν) 1650 (C=O).

Mass as C$_{15}$H$_{20}$N$_6$OS: Calculated: 396.0861. Found: 396.0866.

Compound 110

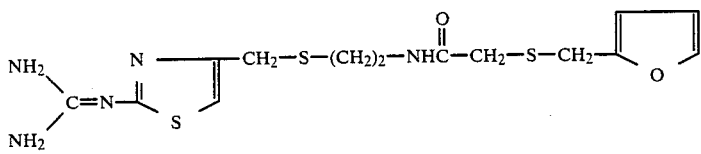

NMR (CDCl₃, δ) 2.66(2H, t, J=6.50), 3.21(2H, s), 3.39(2H, dt, J=6.50, 6.50), 3.67(2H, s), 3.76(2H, s), 1.64(4H, brs), 6.21(1H, d, J=3.0 Hz), 6.30(dd, J=3.0, 2.0 Hz), 6.46(1H, s), 6.98–7.07(1H, m), 7.36(1H, d, J=2.0 Hz).

IR (cm⁻¹, film, ν) 1650 (C=O).

Mass as C₁₄H₁₉N₅O₂S₃: Calculated: 385.0701. Found: 385.0710.

Example 122

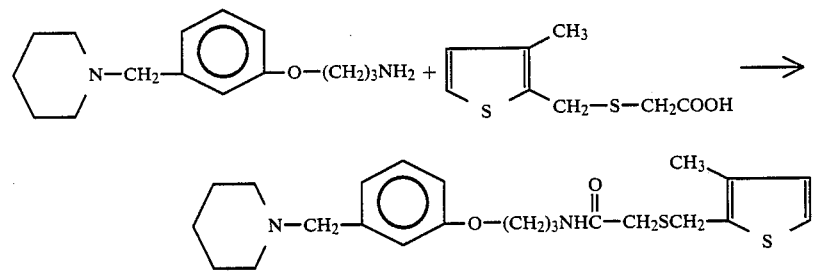

122 mg (0.6 mmol) of 2-{(3-methyl-2-thienyl)methylthio}acetic acid and 124 mg (0.5 mmol) of 3-{3-(piperidinomethyl)phenoxy)propylamine were dissolved in 20 ml of dichloromethane. 115 mg of EDC was added under cooling in an ice bath, and stirred for 18 hours. This reaction solution was washed by adding water, and the organic layer was dried over anhydrous magnesium sulfate. The solvent was evaporated in vacuo, and the residue was purified by silica gel column chromatography using chloroform:methanol=12:1 as developing solvent to obtain 170 mg of the captioned compound 111.

Compound 111

N-[3-{3-(piperidinomethyl)phenoxy}propyl]-2-{(3-methyl-2-thienyl)methylthio}acetamide NMR (CDCl₃, δ) 1.40–1.55(2H, m), 1.55–1.65(4H, m), 1.99(2H, tt, J=5.8 Hz, 5.8 Hz), 2.16(3H, s), 2.35–2.45(4H, m), 3.21(2H, s), 3.44(2H, s), 3.45(2H, dt, J=5.8 Hz, 5.8 Hz), 3.88(2H, s), 4.05(2H, t, J=5.8 Hz), 6.76(1H, d, J=5.4 Hz), 6.80(1H, d, J=7.8 Hz), 6.91(1H, d, J=7.8 Hz), 6.94(1H, s), 7.09(1H, d, J=5.4 Hz), 7.19(1H, brs), 7.21(1H, d, J=7.8 Hz).

IR (cm⁻¹, film, ν) 1650 (C=O).

Mass as C₂₃H₃₂N₂O₂S₂: Calculated: 432.1904. Found: 432.1887.

Examples 123–125

The compounds 112–114 were produced according to the method of Example 122.

Compound 112

N-[3-{3-(piperidinomethyl)phenoxy}propyl]-2-{(5methyl-2-thienyl)methylthio}acetamide

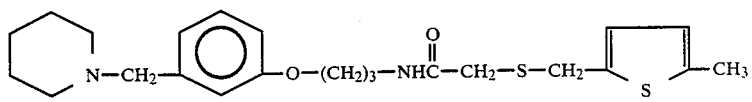

NMR (CDCl₃, δ) 1.40–1.55(2H, m), 1.55–1.65(4H, m), 1.99(2H, tt, J=6.3 Hz, 6.3 Hz), 2.35–2.45(4H, m), 2.42(3H, s), 3.21(2H, s), 3.45(2H, td, J=6.3 Hz, 6.3 Hz), 3.46(2H, s), 3.86(2H, s), 4.05(2H, t, J=6.3 Hz), 6.52(1H, d, J=3.4 Hz), 6.66(1H, d, J=3.4 Hz), 6.75–7.25(5H, m).

IR (cm⁻¹, film, ν) 1650 (C=O).

Mass as C₂₃H₃₂N₂O₂S₂: Calculated: 432.1905. Found: 432.1886.

Compound 113

N-[3-{(piperidinomethyl)phenoxy}propyl]-2-{(5-chloro-2-thienyl)methylthio}acetamide

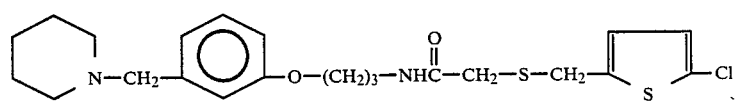

NMR (CDCl₃, δ) 1.40–1.55(2H, m), 1.55–1.65(4H, m), 2.00(2H, tt, J=5.9 Hz, 5.9 Hz), 2.35–2.45(4H, m), 3.20(2H, s), 3.46(2H, dt, J=5.9 Hz, 5.9 Hz), 3.46(2H, s), 3.83(2H, s), 4.07(2H, t, J=5.9 Hz), 6.67(1H, d, J=3.9 Hz), 6.68(1H, d, J=3.9 Hz), 6.81(1H, d, J=7.8 Hz), 6.91(1H, d, J=7.8 Hz), 6.96(1H, s), 7.11(1H, brs), 7.22(1H, t, J=7.8 Hz).

IR (cm$^{-1}$, film, ν) 1670 (C=O).

Mass as $C_{22}H_{29}N_2O_2S_2Cl$: Calculated: 452.1359. Found: 452.1366.

Compound 114

N-[3-{3-(piperidinomethyl)phenoxy}propyl]-2-{(2-chloo-3-thienyl)methylthio}acetamide

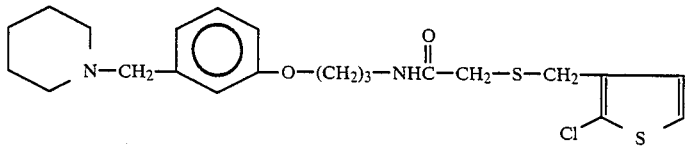

NMR (CDCl$_3$, δ) 1.35–1.50(2H, m), 1.50–1.70(4H, m), 2.00(2H, tt, J=5.9 Hz, 5.9 Hz), 2.30–2.45(4H, m), 3.20(2H, s), 3.45(2H, s), 3.46(2H, dt, J=5.9 Hz, 5.9 Hz), 3.71(2H, s), 4.06(2H, t, J=5.9 Hz), 6.81(1H, dd, J=7.2 Hz, 2.3 Hz), 6.88(1H, d, J=5.8 Hz), 6.91(1H, d, J=7.5 Hz), 6.94(1H, d, J=1.3 Hz), 7.06(1H, d, J=5.7 Hz), 7.22(1H, t, J=7.8 Hz), 7.17(1H, br-s).

IR (cm$^{-1}$, film, ν) 1660 (C=O).

Mass as $C_{22}H_{29}N_2O_2S_2Cl$: Calculated: 452.1358. Found: 452.1355.

EXAMPLE 126

Compound 115

N-[3-{3-(piperidinomethyl)phenoxy}propyl]-2-{(5-methoxycarbonyl-2-thienyl)methylthio}acetamide NMR (CDCl$_3$, δ) 1.40–1.55(2H, m), 1.55–1.65(4H, m), 2.01(2H, tt, J=5.8 Hz, 5.8 Hz), 2.45–2.55(4H, m), 3.21(2H, s), 3.45(2H, s), 3.47(2H, dt, J=5.8 Hz, 5.8 Hz), 3.86(3H, s), 3.93(2H, s), 4.07(2H, t, J=5.8 Hz), 6.81(1H, d, J=7.8 Hz), 6.91(1H, d, J=3.9 Hz), 6.92(1H, d, J=7.8 Hz), 6.96(1H, s), 7.11(1H, brs), 7.22(1H, t, J=7.8 Hz), 7.60(1H, d, J=3.9 Hz).

IR (cm$^{-1}$, film, ν) 1710 (—COOCH$_3$), 1660 (—CONH—).

Mass as $C_{24}H_{32}N_2O_4S_2$: Calculated: 476.1804. Found: 476.1811.

Example 127

The compound 116 was produced according to the method of Example 126.

Compound 116

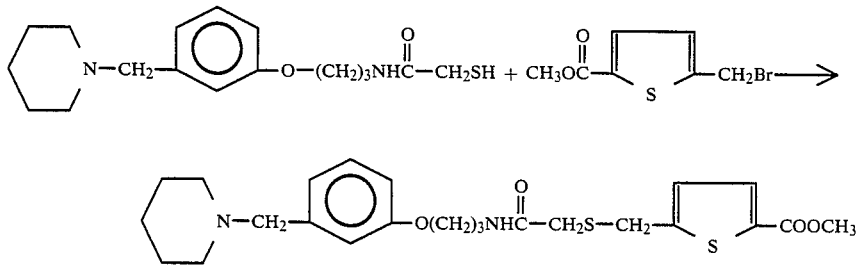

322 mg (1 mmol) of N-[3-{3-(piperidinomethyl)-phenoxy}propyl]-2-mercaptoacetamide was dissolved in 5 ml of dimethylformamide under a nitrogen atmosphere. 67 mg (1 mmol) of 60% sodium hydride was added under cooling in an ice bath, and stirred for 20 minutes. The solution prepared by dissolving 235 mg (1 mmol) of methyl-5-bromomethyl-2-thiophene carboxylate in 4 ml of dimethylformamide was added dropwise, and stirred at room temperature for 2 hours. The reaction solution was poured into ice water, and the product was extracted with benzene. The benzene layer was washed with water, and dried over anhydrous sodium sulfate. The solvent was evaporated in vacuo, and the residue was purified by silica gel chromatography using chloroform:methanol=9:1 to obtain 104 mg of the captioned colorless oily compound 115.

N-[3-{3-(piperidinomethyl)phenoxy}propyl]-2-{(3-acetamide-2-thienyl)methylthio}acetamide

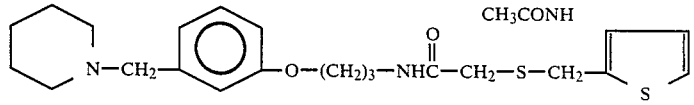

NMR (CDCl$_3$, δ) 1.40–1.50(2H, m), 1.50–1.70(4H, m), 2.03(2H, tt, J=6.1 Hz, 6.1 Hz), 2.18(3H, s), 2.20–2.50(4H, m), 2.93(2H, s), 3.44(2H, s), 3.52(2H, dt, J=6.1 Hz, 6.1 Hz), 3.96(2H, s), 4.08(2H, t, J=6.1 Hz), 6.50(1H, brs), 6.76(1H, d, J=7.4 Hz), 6.91(1H, d, J=7.4 Hz), 6.92(1H, s), 7.20(1H, t, J=5.5 Hz), 7.25(1H, d, J=5.2 Hz), 7.46(1H, d, J=5.2 Hz), 9.60(1H, s).

IR (cm$^{-1}$, film, ν) 1650 (C=O).

EXAMPLES OF PRODUCTION OF RAW MATERIALS

Example 128

2.4 g 3-{3-(piperidinomethyl)phenoxy}-propylamine was dissolved in 50 ml of dichloromethane, and cooled in an ice bath. 1.92 g of EDC was added, and stirred at 0° C. for 30 minutes then at room temperature overnight. 30 ml of water and 30 ml of dichloromethane were added to the reaction solution, and the organic layer was separated, dried over anhydrous magnesium sulfate, and the solvent was evaporated in vacuo to obtain oily N-[3-{3-(piperidinomethyl)phenoxy}propyl]-2-chloroacetamide.

Yield: 1.97 g.

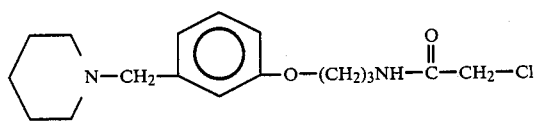

IR (film, cm$^{-1}$, $\nu$) 1670.

NMR (CDCl$_3$, $\delta$) 1.40–1.70(6H, m), 2.06(2H, tt, J=6.2 Hz), 2.30–2.50(4H, m), 3.46(2H, s), 3.56(2H, t, J=6.2 Hz), 4.07(2H, s), 4.10(2H, t, J=6.2 Hz), 6.80–7.30(5H, m).

Example 129

Colorless oily N-[3-{3-(piperidinomethyl)phenoxy{propyl]-4-chlorobutylamide was produced in the same method as Example 128 except that 1.30 g of 4-chlorobutyric acid was employed instead of 1.0 g of monochloroacetic acid.

Yield: 2.2 g.

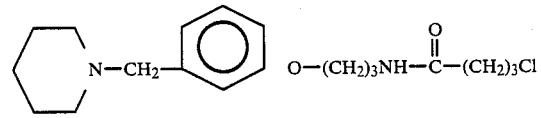

IR (film, cm$^{-1}$, $\nu$) 1650.

NMR (CDCl$_3$, $\delta$) 1.30–1.70(6H, m), 1.80–2.50(10H, m), 3.38(2H, t, J=6 Hz), 3.41(2H, s), 3.54(2H, t, J=6 Hz), 4.00(2H, t, J=6 Hz), 6.05–7.30(5H, m).

Example 130

Colorless oily N-[3-{3-(piperidinomethyl)phenoxy}propyl]-6-bromohexylamide was produced in the same method as Example 128 except that 2.06 g of 6-bromocaproic acid was employed instead of 1.0 g of monochloracetic acid.

Yield: 2.5 g.

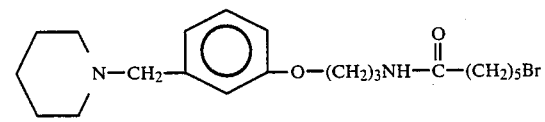

IR (film, cm$^{-1}$, $\nu$) 1650.

NMR (CDCl$_3$, $\delta$) 1.40–2.30(16H, m), 2.35–2.65(4H, m), 3.20–3.60(4H, m), 3.55(2H, s), 4.00(2H, t, J=6 Hz), 6.10(1H, brs), 6.60–7.20(4H, m).

Example 131

0.22 g of 3-{3-(1-perhydroazepinylmethyl)phenoxy} propylamine was dissolved in 10 ml of dichloromethane, and cooled in an ice bath. 0.1 g of monochloroacetic acid and 0.2 g of EDC were added to this solution, and stirred at 0° C. for 30 minutes then at room temperature overnight. 10 ml of water and 10 ml of dichloromethane were added to the reaction solution, and the organic layer was separated, dried over anhydrous magnesium sulfate, and the solvent was evaporated in vacuo to obtain colorless oily N-[3-{3-(1-perhydroazepinylmethyl)phenoxy}propyl]-2-chloroacetamide. Yield: 0.15 g.

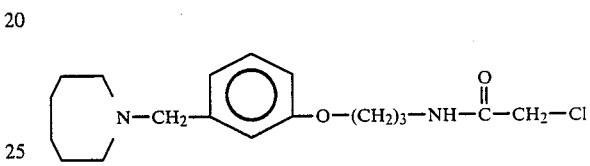

IR (film, cm$^{-1}$, $\nu$) 1670.

NMR (CDCl$_3$, $\delta$) 1.50–1.70(8H, m), 2.05(2H, tt, J=6.3 Hz), 2.55–2.70(4H, m), 3.67(2H, s), 4.07(2H, s), 4.10(2H, t, J=6.3 Hz), 6.75–7.30(5H, m).

Example 132

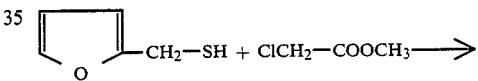

20.00 g of furfurylmercaptane and 19.01 g of methylchloroacetate were dissolved in 400 ml of acetnitrile. 29.02 g of anhydrous potassium carbonate and 2.90 g of potassium iodide were added to this solution, and refluxed for 3 hours. After cooling, insoluble materials were removed by filtration, and acetnitrile was evaporated from the filtrate in vacuo. The product was extracted from the residue by 400 ml of benzene, and washed with water. The benzene layer was dried over anhydrous magnesium sulfate, and the solvent was evaporated in vacuo to obtain the captioned colorless oily product. Yield: 30.45 g bp 96°–98° C./1 mmHg.

NMR (CDCl$_3$, $\delta$) 3.20(2H, s), 3.74(3H, s), 3.86(2H, s), 6.24(1H, d, J=3.0 Hz), 6.30–6.35(1H, m), 7.38(1H, d, J=2.0 Hz).

The following compounds were produced similarly.

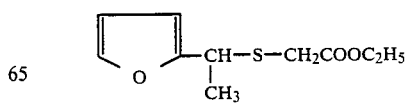

Purification: Distillation.

NMR (CDCl₃, δ) 1.28(3H, t, J=7.0 Hz), 1.61(3H, d, J=7.5 Hz), 3.14(2H, s), 4.16(2H, d, t, J=7.0 Hz, 7.0 Hz), 4.23(1H, q, J=7.5 Hz), 6.21(1H, d, J=3.0 Hz), 6.30(1H, dd, J=3.0 Hz, 2.0 Hz), 7.37(1H, d, J=2.0 Hz).

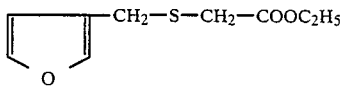

Purification: Column Chromatography AcOEt/Hexane=1/19.

NMR (CDCl₃, δ) 1.29(3H, t, J=7.0 Hz), 3.10(2H, s), 3.68(2H, s), 4.18(2H, dt, J=7.0 Hz, 7.0 Hz), 6.41(1H, d, J=1.5 Hz), 7.38(1H, s), 7.39(1H, d, J=1.5 Hz).

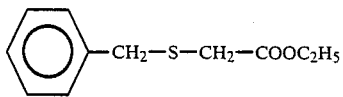

Purification: Distillation.
b.p. 99°–103° C./2 mmHg.
NMR (CDCl₃, δ) 1.29(3H, t, J=7.0 Hz), 3.06(2H, s), 3.88(2H, s), 4.20(2H, dt, J=7.0 Hz, 7.0 Hz), 7.25–7.35(5H, m).

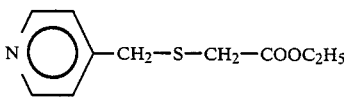

Purification: Distillation.
b.p. 127°–134° C./1 mmHg.
NMR (CDCl₃, δ) 1.29(3H, t, J=7.0 Hz), 3.05(2H, s), 3.80(2H, s), 4.19(2H, dt, J=7.0), 7.28(2H, d, J=5.5 Hz), 8.57(2H, d, J=5.5 Hz).

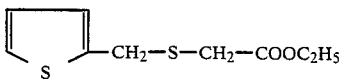

Purification: Distillation.
b.p. 91°–95° C./8 mmHg.
NMR (CDCl₃, δ) 1.30(3H, t, J=7.0 Hz), 3.15(2H, s), 4.07(2H, s), 4.19(2H, dt, J=7.0), 6.90–7.00(2H, m), 7.20–7.30(1H, m).

Example 133

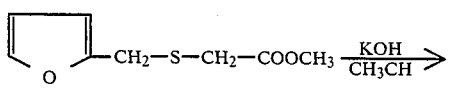

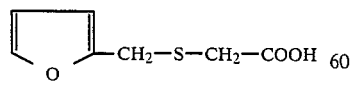

10 g of methyl-2-(furfurylthio)acetate was dissolved in 60 ml of methanol, and the solution prepared by dissolving 4.25 g of 85% potassium hydride in 15 ml of water was added dropwise. The mixture was stirred for 2 hours at room temperature, and pH was adjusted to 5 by adding 2N aqueous hydrochloric acid. Water and methanol were evaporated under reduced pressure. 100 ml of ethyl acetate and 100 ml of water were added to the residue and extraction was carried out. The ethyl acetate layer was dried over anhydrous magnesium sulfate, and the solvent was evapoated in vacuo to obtain the captioned 2-(furfurylthio)acetic acid. Yield: 9.2 g.

NMR (CDCl₃, δ) 3.22(2H, s), 3.89(2H, s), 6.28(1H, d, J=3.0 Hz), 6.32(1H, dd, J=3.0 Hz, 2.0 Hz), 7.39(1H, d, J=2.0 Hz).

The following compounds were produced similarly.

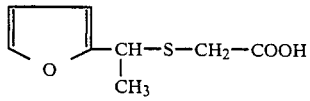

NMR (CDCl₃, δ) 1.60(3H, d, J=7.5 Hz), 2.18(2H, s), 3.18(2H, s), 4.21(1H, q, J=7.5 Hz), 6.20(1H, d, J=3.0 Hz), 6.29(1H, dd, J=3.0, 2.0 Hz), 7.37(1H, d, J=2.0 Hz), 10.3(1H, brs).

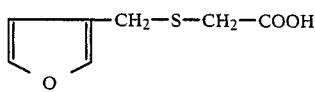

NMR (CDCl₃, δ) 3.18(2H, s), 3.80(2H, s), 6.40(1H, d, J=1.5 Hz), 7.38(1H, s), 7.40(1H, d, J=1.5 Hz).

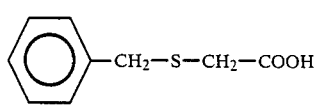

NMR (CDCl₃, δ) 3.11(2H, s), 3.87(2H, s), 7.25–7.40(5H, m).

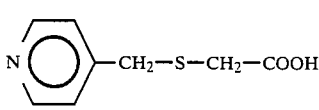

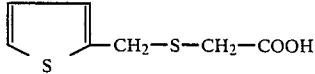

NMR (CDCl₃, δ) 3.18(2H, s), 4.02(2H, s), 6.80–7.00(2H, m), 7.10–7.20(1H, m).

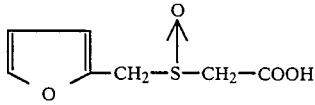

NMR (CDCl₃, δ) 3.58(1H, d, J=14 Hz), 3.72(1H, d, J=14 Hz), 4.20(1H, d, J=14 Hz), 4.31(1H, d, J=14 Hz), 6.34(1H, d, J=3.0 Hz), 6.42(1H, dd, J=2.0 Hz, 3.0 Hz), 7.40(1H, d, J=2.0 Hz), 7.85(1H, brs).

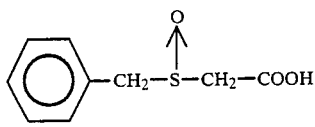

NMR (CDCl₃, δ) 3.53(1H, d, J=14.5 Hz), 3.64(1H, d, J=14.5 Hz), 4.16(1H, d, J=14.5 Hz), 4.21(1H, d, J=14.5 Hz), 7.20-7.40(5H, m), 10.5(1H, brs).

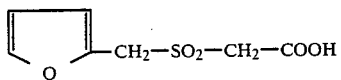

NMR (CDCl₃, δ) 3.33(2H, s), 4.75(2H, s), 6.45(1H, d, J=3.0 Hz), 6.56(1H, dd, J=3.0, 2.0 Hz). 7.55(1H, d, J=2.0 Hz).

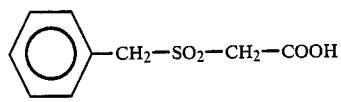

NMR (CDCl₃, δ) 3.83(2H, s), 4.54(2H, s), 7.40-7.55(5H, m).

Example 134

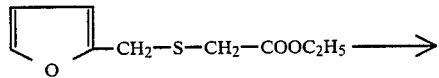

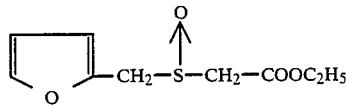

2.00 g of ethyl-2-(furfurylthio)acetate was dissolved in 40 ml of methanol, and stirred under cooling in an ice bath. 2.50 g of sodium metaperiodate dissolved in 20 ml of water was added dropwise, and stirred overnight at room temperature. The reaction product was extracted by adding 100 ml of dichloromethane, and washed with water. Dichloromethane was evaporated in vacuo, and the residue was purified by column chromatography using benzene:ethyl acetate=4:1 as developing solvent to obtain the captioned ethyl-2-(furfurylsulfinyl)acetate. Yield: 1.93 g.

NMR (CDCl₃, δ) 1.32(3H, t, J=7.0 Hz), 3.57(1H, d, J=14 Hz), 3.66(1H, d, J=14 Hz), 4.23(2H, dt, J=7.0 Hz, 7.0 Hz), 4.17(1H, d, J=14 Hz), 4.32(1H, d, J=14 Hz), 6.41(1H, d, J=3.0 Hz), 6.46(1H, dd, J=3.0 Hz, 2.0 Hz), 7.46(1H, d, J=2.0 Hz).

The following compounds were produced similarly.

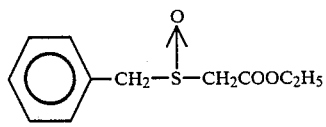

NMR (CDCl₃, δ) 1.31(3H, t, J=7.0 Hz), 3.47(1H, d, J=14 Hz), 3.57(1H, d, J=14 Hz), 4.12(1H, d, J=14 Hz), 4.24(2H, dt, J=7.0 Hz, 7.0 Hz), 4.25(1H, d, J=14 Hz), 7.30-7.45(5H, m).

Example 135

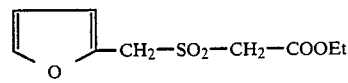

2.00 g of ethyl-2-(furfurylthio)acetate was dissolved in acetic acid, and heated to 90° C. To the solution was added dropwise 5.4 ml of 30% aqueous hydrogen peroxide, and stirred for 30 minutes in an oil bath of 90° C. The reaction solution was cooled, and extraction was carried out by using 300 ml of dichloromethane. The dichloromethane layer was washed with water, and dried over anhydrous magnesium sulfate. The solvent was evaporated in vacuo, and the residue was purified by column chromatography using benzene:ethyl acetate=4:1 as developing solvent to obtain the captioned ethyl-2-(furfurylsulfonyl)acetate.

Yield: 0.37 g.

NMR (CDCl₃, δ) 1.35(3H, t, J=7.0 Hz), 3.92(2H, s), 4.31(2H, dt, J=7.0 Hz, 7.0 Hz), 4.63(2H, s), 6.44(1H, d, J=3.0 Hz), 6.57(1H, dd, J=3.0 Hz, 2.0 Hz), 7.49(1H, d, J=2.0 Hz).

The following compound was produced similarly.

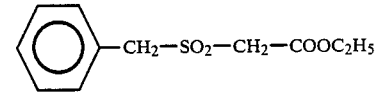

NMR (CDCl₃, δ) 1.35(3H, t, J=7.0 Hz), 3.77(2H, s), 4.31(2H, dt, J=7.0 Hz, 7.0 Hz), 4.53(2H, s), 7.40-7.55(5H, m).

Example 136

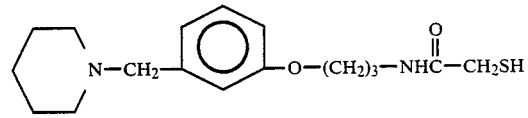

2.94 g of 3-{3-(piperidinomethyl)phenoxy}propylamine was dissolved in 80 ml of dichloromethane, and stirred under cooling in an ice bath. 1.60 g of 2-(acetylthio)acetic acid and 2.26 g of EDC were added to this solution, and stirred at 0° C. for 30 minutes then at room temperature overnight. 100 ml of water and 50 ml of dichloromethane were added to the reaction solution, and extraction was carried out. The dichloromethane layer was washed twice with water, and dried over anhydrous magnesium sulfate. The solvent was evaporated in vacuo, and the residue was purified by silica gel column chromatography using methanol:dichloromethane=1:15 as developing solvent to obtain the colorless oily N-[3-{3-(piperidinomethyl)phenoxy}propyl]-2-(acetylthio)acetamide. Yield: 2.23 g.

NMR (CDCl₃, δ) 1.40-1.70(6H, m), 1.97(2H, tt, J=5.9 Hz, 5.9 Hz), 2.36(3H, s), 2.30-2.45(4H, m), 3.44(2H, s), 3.46(2Hm, dt, J=5.9 Hz, 5.9 Hz), 3.55(2H, s), 4.02(2H, t, J=5.9 Hz), 6.58(1H, brs), 6.75-6.95(3H, m), 7.15-7.25(1H, m).

2.23 g of this acetamide was dissolved in a mixed solvent of 30 ml of methanol and 3 ml of water, and cooled in an ice bath. 0.48 g of 85% potassium hydroxide was added to this solution, and stirred at 0° C. for 1.5 hours. pH of the reaction solution was adjusted to 7 by adding 2N aqueous hydrochloric acid, and extraction was carried out by adding 100 ml of dichloromethane and 50 ml of water. The dichloromethane layer was washed twice with water, and dried over anhydrous magnesium sulfate. The solvent was evapoated in vacuo to obtain the captioned colorless oily N-[3-{3-(piperidinomethyl)phenoxy}propyl]-2-mercaptoacetamide. Yield: 1.86 g.

NMR (CDCl$_3$, δ) 2.35(1H, brs), 1.40–1.65(6H, m), 2.05(2H, tt, J=6.3 Hz, 6.3 Hz), 2.30–2.45(4H, m), 3.26(2H, s), 3.44(2H, s), 3.54(2H, dt, J=6.3 Hz, 6.3 Hz), 4.08(2H, t, J=6.3 Hz), 6.80–7.00(3H, m), 7.15–7.30(2H, m).

Examples 137–139

(Example 137)

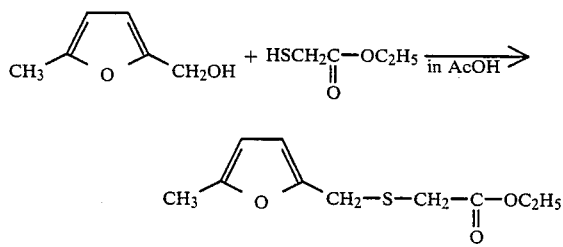

1.23 g of 2-methyl-5-hydroxymethylfuran and 1.32 g of thioglycollic acid ethyl ester were dissolved in 10 ml of acetic acid, and refluxed 3 hours. Acetic acid was evaporated and the residue was dissolved in benzene. This benzene solution was washed with satutrated aqueous sodium hydrogen carbonate solution and then washed with water. The benzene layer was dried over anhydrous magnesium sulfate, and benzene was evaporated under reduced pressure to obtain 730 mg (31%) of the captioned product.

(Example 138)

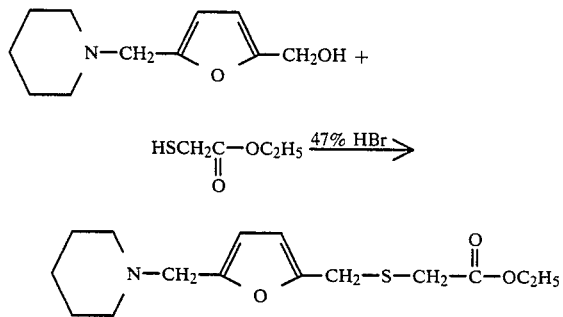

300 mg of 2-piperidinomethyl-5-hydroxymethylfuran and 185 mg of thioglycollic acid ethyl ester were dissolved in 1.8 ml of 47% hydrobromic acid, and allowed to react for 5 days at room temperature. The reaction solution was made alkaline by using sodium hydrogen carbonate, and the product was extracted with dichloromethane. The dichloromethane layer was dried over anhydrous magnesium sulfate, and the solvent was evaporated under reduced pressure to obtain 30 mg of the captioned product.

(Example 139)

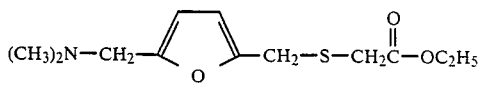

was produced from

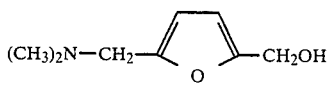

in the same method as Example 138.

Product NMR (CDCl$_3$, δ)

Ex. 137: 1.29(3H, t, J=6.8 Hz), 2.27(3H, s), 3.17(2H, s), 3.81(2H, s), 4.19(2H, q, J=6.8 Hz), 5.88(1H, d, J=3.0 Hz), 6.10(1H, d, J=3.0 Hz).

Ex. 138: 1.29(3H, t, J=7.3 Hz), 1.35–1.50(2H, m), 1.50–1.70(4H, m), 2.35–2.50(4H, m), 3.17(2H, s), 3.51(2H, s), 3.84(2H, s), 4.19(2H, q, J=7.3 Hz), 6.12(1H, d, J=3.4 Hz), 6.16(1H, d, J=3.4 Hz).

Ex. 139: 1.29(3H, t, J=6.7 Hz), 2.25(6H, s), 3.17(2H, s), 3.43(2H, s), 3.84(2H, s), 4.21(2H, q, J=6.7 Hz), 6.11(1H, d, J=2.9 Hz), 6.17(1H, d, J=2.9 Hz).

The following 5 carboxylic acids were produced by hydrolysis with KOH/CH$_3$OH in H$_2$O.

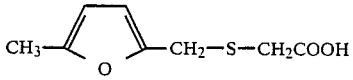

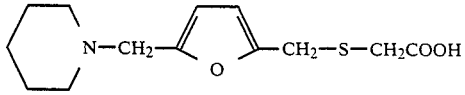

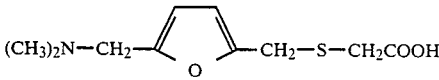

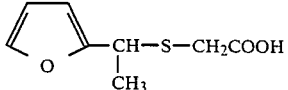

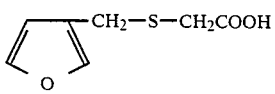

NMR of newly produced carboxylic acids are as follows:

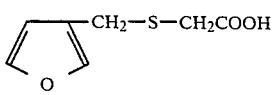

NMR (CDCl$_3$, δ) 3.18(2H, s), 3.80(2H, s), 6.40(1H, d, J=1.5 Hz), 7.38(1H, s), 7.40(1H, d, J=1.5 Hz).

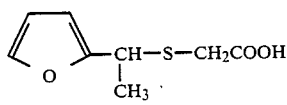

NMR (CDCl$_3$, δ) 1.60(3H, d, J=7.5 Hz), 2.18(2H, s), 3.18(2H, s), 4.21(1H, q, J=7.5 Hz), 6.20(1H, d, J=3.0 Hz), 6.29(1H, dd, J=3.0, 2.0 Hz), 7.37(1H, d, J=2.0 Hz), 10.3(1H, brs).

Example 140

Synthesis of

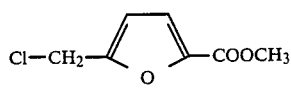

(Methyl-5-chloromethyl-2-furan carboxylate)

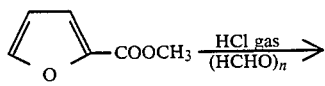 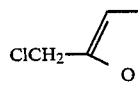

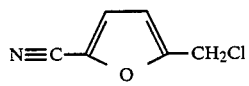

Ann., 580 176 (1953), O. Moldenhauer.

Example 141

Synthesis of

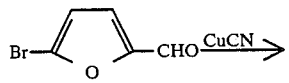

(2-Chloromethyl-5-cyanofuran)

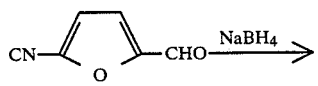

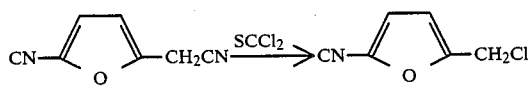

"Yakugaku-Zasshi, 93(11), 1526–1529(1973), H. Nakao et al.

Example 142

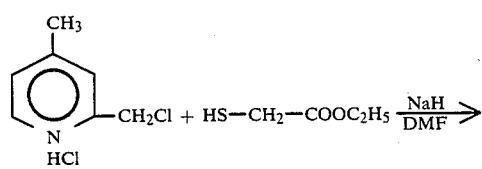

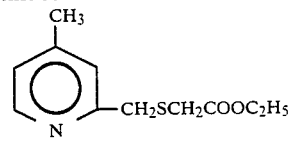

0.60 g (5 mmol) of thioglycollic acid ethyl ester was dissolved in 5 ml of dimethylformamide, and cooled in an ice bath. 0.40 g (10 mmol) of 60% sodium hydride was added, and stirred for 15 minutes. 0.88 g (5 mmol) of 4-methyl-2-chloromethylpyridine hydrochloride was dissolved in 8 ml of dimethylformamide, and added to this solution. Stirring was continued for 2 hours under cooling. The reaction solution was poured into ice water, and the product was extracted three times with benzene. The benzene extracts were combined, and the product was extracted with 30 ml of 5% aqueous hydrochloric acid. The hydrochloric acid layer was adjusted to pH 8 by using aqueous potassium carbonate solution, and extracted three times with each 30 ml of ethyl acetate. The ethyl acetate layer was dried over anhydrous sodium sulfate, and the solvent was evaporated in vacuo to obtain the captioned oily product.

Yield: 0.71 g (67%).

NMR (300 MHz, COCl$_3$, δ) 1.28(3H, t, J=7.0 Hz), 2.35(3H, s), 3.22(2H, s), 3.92(2H, s), 4.17(2H, q, J=7.0 Hz), 7.00(1H, d, J=3.0 Hz), 7.18(1H, s), 8.41(1H, d, J=3.0 Hz).

Example 143

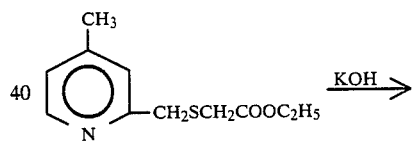

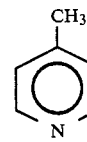

0.71 g (3.3 mmol) of ethyl-2-(4-methylpyridyl-2-methylthio)acetate was dissolved in 15 ml of methanol. 0.28 g (6.6 mmol) of potassium hydroxide was added to the solution, and stirred overnight at room temperature. The reaction solution was adjusted to pH 4 with 5% aqueous hydrochloric acid, and methanol and water were evaporated under reduced pressure. The product was extracted from the residue by using 100 ml of dichloromethane:methanol=9:1, and the captioned oily product was obtained. Yield: 0.60 g (92%)

The following compounds were produced similarly.

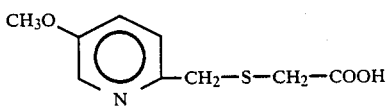

-continued

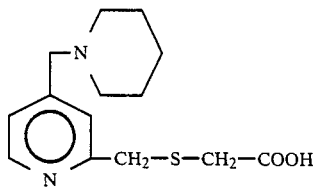

Example 144
Syntheses of

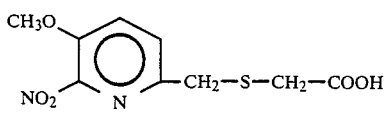

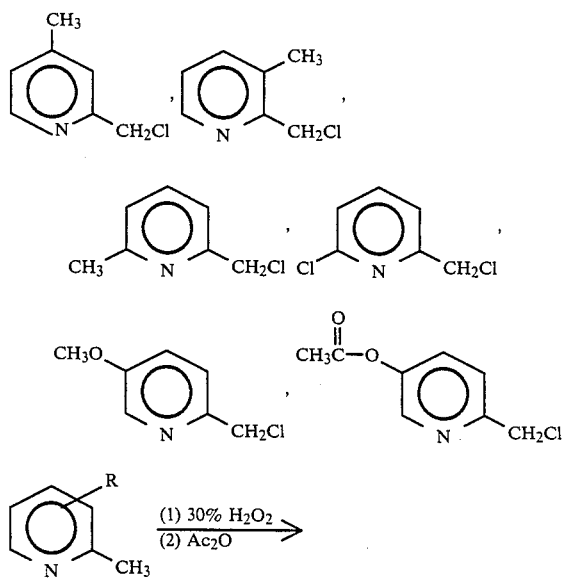

The compound 1 was dissolved in acetic acid, and 30% aqueous hydrogen peroxide was added to the solution. This mixture was stirred at 85°-90° C. for 6 hours. Water was added to this reaction solution, and solvent was evaporated. Acetic acid anhydride was added to the residue, and distillation under reduced pressure was carried out to obtain the compound 2 (Reference: S. Ginsburg and I. B. Wilson, J. Am. Chem. Soc., vol. 79, p481(1957)).

The compound 2 was dissolved in methanol-water, and potassium hydroxide was added. This solution was stirred at room temperature, and then solvent was evaporated. The product was extracted with chloroform, and the chloroform layer was dried over anhydrous magnesium sulfate. Then, the solvent was evaporated in vacuo to obtain the compound 3.

The compound 3 was dissolved in chloroform, and thionyl chloride was added under cooling in an ice bath. This solution was stirred at room temperature for 2 hours, and solvent was evaporated under reduced pressure to obtain the compound 4.

Synthesis of

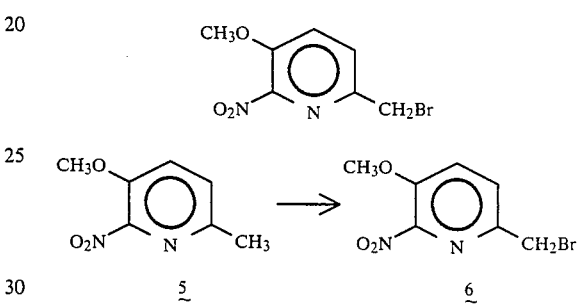

The compound 5 was dissolved in carbon tetrachloride, and N-bromosuccinic acid imide and benzoyl peroxide were added. This mixture was refluxed for 23 hours. The reaction solution was cooled, and insoluble materials were filtered off. The carbon tetrachloride layer was washed with saturated A brine, and dried over anhydrous magnesium sulfate. The solvent was evaporated in vacuo, and the residue was purified by silica gel column chromatography using benzene to obtain the compound 6.

Syntheses of

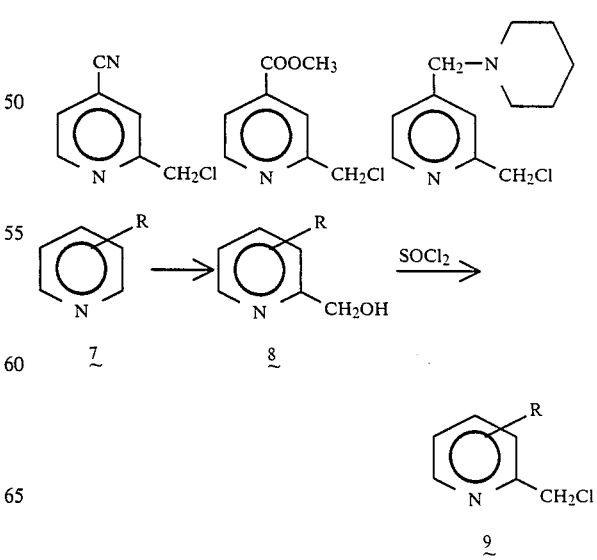

The compound 7 was dissolved in methanol-water, and sulfuric acid was added. Ammonium persulfate dissolved in water under refluxing was added, and refluxed for 4 hours. Water was added to the reaction solution, and the solvent was evaporated. The residue was neutralized with 1N aqueous soldium hydroxide, and the product was extracted with chloroform. The chloroform layer was dried over anhydrous magnesium sulfate, and the solvent was evaporated in vacuo to obtain the compound 8 (Reference: Japanese Patent KOKAI No. 57-91986).

The compound 8 was dissolved in chloroform, and thionyl chloride was added under cooling in an ice bath. The mixture was stirred at room temperature for 2 hours, and solvent was evaporated under reduced pressure to obtain the compound 9.

Example 145

The raw amine compounds of Examples 100–102 were prepared according to the method disclosed in Belgian Patent No. 857388 (Japanese Patent KOKAI No. 54-115385).

The raw amine compounds of Examples 103 and 104 were prepared as follows:

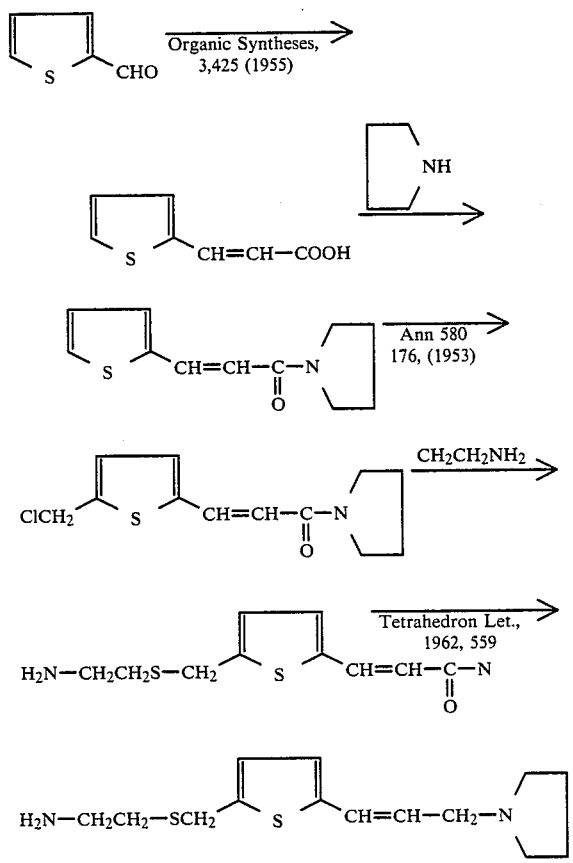

The raw amine compound of Example 105 was produced according to the method disclosed in Japanese Patent KOKAI No. 55-10591 where piperidine was employed instead of dimethylamine.

The raw amine compound of Example 106 was produced according to the method disclosed in Japanese Patent KOKAI No. 57-91980.

The raw amine compound of Example 107 was produced as follows:

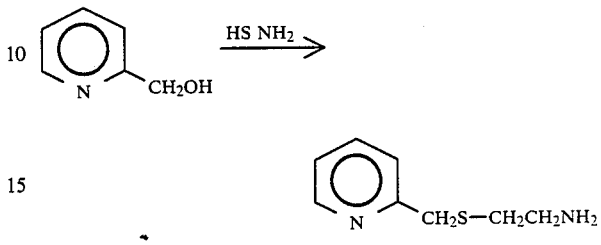

The raw amine compound of Example 108 was produced according to the method disclosed in Japanese Patent KOKAI No. 57-91986.

The raw amine compound of Example 109 was produced according to the method disclosed in Japanese Patent KOKAI No. 57-91986 where dimethylamine was replaced by piperidine.

The raw amine compound of Example 110 was produced according to the method disclosed in Japanese Patent KOKAI No. 58-170779.

The raw amine compound of Example 111 was produced according to the method of Example 1 of Japanese Patent KOKAI No. 58-170779 where piperidine was employed instead of dimethylamine.

The raw amine compound of Example 112 was produced as follows:

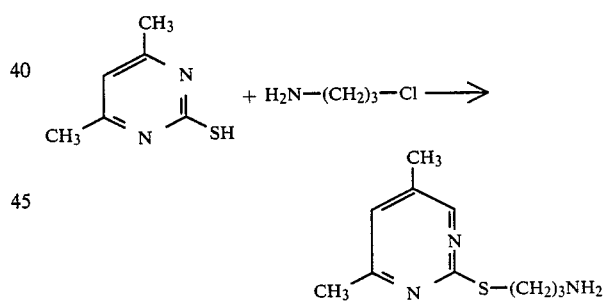

The raw amine compound of Example 113 was produced according to the method of Example 1 of Japanese Patent KOKAI No. 49-102668.

The raw amine compound of Example 114 was produced as follows:

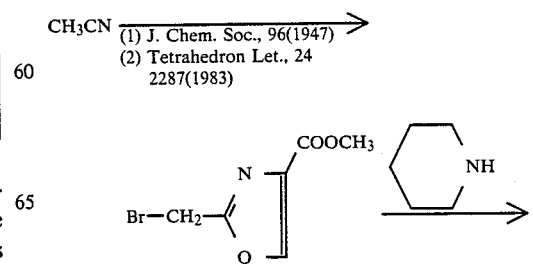

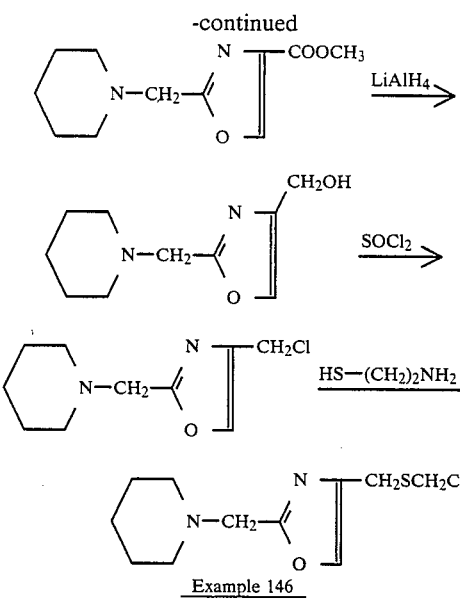

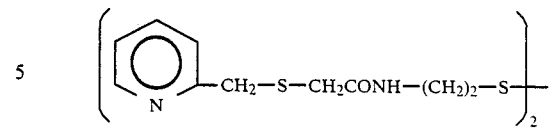

NMR (CDCl₃, δ) 2.85(6H, t, J=6.5 Hz), 3.14(4H, s), 3.60(4H, dt, J=6.5 Hz), 3.89(4H, s), 7.20–7.35(4H, m), 7.65–7.75(2H, m), 7.98(2H, brs), 8.50–8.60(2H, m).

Example 147

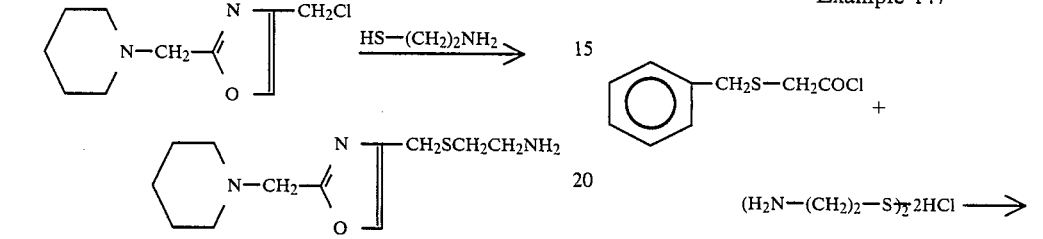

Example 146

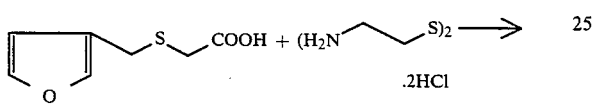

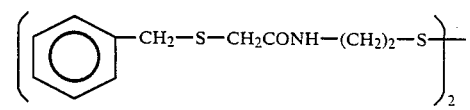

2.37 g (0.0105 mol) of cystamine dichloride was dissolved in 70 ml of dimethylformamide. 1.01 g (0.0253 mol) of 60% sodium hydride was added under cooling in an ice bath, and stirred at room temperature for 30 minutes. This mixture was cooled again in an ice bath. 3.63 g (0.021 mol) of 2-(3-furylmethylthio)acetic acid dissolved in 30 ml of dimethylformamide and 4.84 g (0.025 mol) of EDC were added, and stirred for 18 hours. Extraction was carried out using 200 ml of water and 200 ml of benzene, and the benzene layer was dried over anhydrous magnesium sulfate. The solvent was evaporated in vacuo to obtain white crystals of the object compound. Yield: 1.82 g.

m.p.: 81.6°–83.0° C.

NMR (CDCl₃, δ) 2.82(6H, t, J=6.5 Hz), 3.17(4H, s), 3.58(4H, dt, J=6.5 Hz, 6.5 Hz), 3.61(4H, s), 6.39(2H, s), 7.15(2H, brs), 7.35–7.40(4H, m).

The following compound was produced similarly.

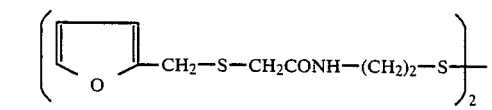

m.p.: 82.8°–83.9° C.

NMR (CDCl₃, δ) 2.80(6H, t, J=6.5 Hz), 3.28(4H, s), 3.54(4H, dt, J=6.5 Hz, 6.5 Hz), 3.78(4H, s), 6.28(2H, d, J=3.0 Hz), 6.32(2H, dd, J=3.0 Hz, J=2.0 Hz), 7.15(2H, brs), 7.39(2H, d, J=2.0 Hz).

2.81 g (0.0125 mol) of cystamine dichloride was dissolved in 100 ml of water, and 6.99 g (0.0506 mol) of potassium carbonate was added to the solution. 5.10 g (0.0253 mol) of 2-(benzylthio)acetylchloride dissolved in 50 ml of chloroform was added dropwise with vigorous stirring under cooling in an ice bath, and the stirring was continued for one and a half hours. The product was extracted with 50 ml of chloroform. The chloroform layer was washed with water, and dried over anhydrous magnesium sulfate. The solvent was evaporated in vacuo, and yellow crystals deposited were purified by silica gel column chromatography using methanol:dichloromethane=3:97 to obtain white crystals of the object compound. Yield: 4.32 g.

m.p.: 87.9°–89.0° C.

NMR (CDCl₃, δ) 2.76(6H, t, J=6.5 Hz), 3.15(4H, s), 3.52(4H, dt, J=6.5 Hz, 6.5 Hz), 3.75(4H, s), 7.10(2H, brs), 7.20–7.40(10H, m).

The following compounds were produced similarly.

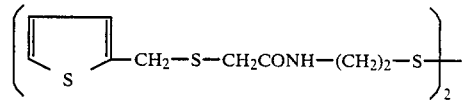

m.p.: 64.9°–65.5° C.

NMR (CDCl₃, δ) 2.79(6H, t, J=6.5 Hz), 3.22(4H, s), 3.55(4H, dt, J=6.5 Hz, 6.5 Hz), 3.99(4H, s), 6.9–7.0(4H, m), 7.11(2H, brs), 7.20–7.30(2H, m).

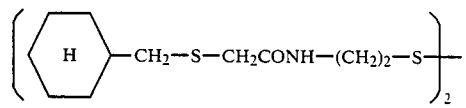

NMR (CDCl₃, δ) 0.90-1.90(22H, m), 2.44(4H, d, J=7.0 Hz), 2.85(4H, t, J=6.5 Hz), 3.22(4H, s), 3.64(4H, dt, J=6.5 Hz, 6.5 Hz), 7.36(2H, brs).

m.p.: 77.6°-79.0° C.

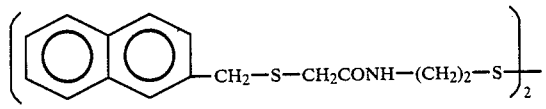

NMR (CDCl₃, δ) 2.61(6H, t, J=6.5 Hz), 3.15(4H, s), 3.43(4H, dt, J=6.5 Hz, 6.5 Hz), 3.90(4H, s), 7.05(2H, brs), 7.40-7.85(14H, m).

m.p.: 155.1°-157.3° C.

EXAMPLES OF FUNCTION

Example 148

Histamine $H_2$-receptor antagonistic actions of the exemplified compounds were measured. Male Guinea-Pig weighing 300 to 350 g was killed by a blow on the head. After thoracotomy, the right atrium was isolated rapidly, and the surrounding tissues of the right atrium was carefully dissected. The preparation was mounted isometrically in 30 ml organ bath containing an oxygenated ($O_2$ 95%+$CO_2$ 5%) Krebs-Henselite solution at 32° C. 1 g of resting tension was loaded through the experiment. Contraction of the right atrium to histamine was measured with a force-displacement transducer, and heart rate was measured with a heart rate meter. After the control dose-response curve in the presence of tested compound ($1 \times 10^{-6}$M or $1 \times 10^{-7}$M) was determined.

The $pA_2$ value of each compound was determined from these two curves by the method of J. M. Van Rossum (Arch. Int. Pharmacodyn. Ther 143-299 (1963)).

The results are shown in Table 1.

TABLE 1

|  | $pA_2$ |
|---|---|
| Compound 1 | 7.5 |
| Compound 12 | 7.3 |
| Compound 16 | 7.9 |
| Compound 19 | 7.3 |
| Compound 44 | 6.6 |
| Compound 48 | 7.5 |
| Compound 57 | 7.5 |
| Compound 58 | 7.5 |
| Compound 69 | 8.4 |
| Compound 72 | 7.0 |
| Compound 73 | 7.3 |
| Compound 74 | 6.2 |
| Compound 75 | 7.7 |
| Compound 79 | 8.1 |
| Compound 82 | 7.7 |
| Compound 86 | 7.6 |
| Compound 94 | 6.5 |
| Compound 100 | 7.0 |
| Compound 104 | 6.7 |
| Compound 105 | 7.1 |
| Compound 106 | 6.7 |
| Compound 107 | 6.1 |
| Compound 109 | 7.6 |
| Compound 110 | 7.1 |
| Compound 112 | 7.8 |
| Compound 113 | 7.6 |
| Compound 114 | 7.4 |
| Compound 116 | 7.5 |

In a comparison, $pA_2$ value of cimetidine was measured in the same manner as above, and it was found to be 6.5.

Example 149

Cytoprotective actions of the exemplified compounds were examined.

Male Donryu rats weighing 150-250 g were used after fasting for 24 hours. 10 mg/kg P.O. of the test compound was administrated, and 5 ml/kg of a necrotizing agent (0.4N HCl+50% EtOH) was orally administrated after 30 minutes. After 1 hour from the administration of the necrotizing agent, its stomach was dissected out, and fixed with formalin. Total area of gastric mucosal leasion was measured, and compared with a control group to determine inhibition %.

The results are shown in Table 2.

TABLE 2

|  | Repression % |
|---|---|
| Compound 1 | 59 |
| Compound 14 | 55 |
| Compound 19 | 63 |
| Compound 20 | 45 |
| Compound 21 | 60 |
| Compound 30 | 62 |
| Compound 35 | 61 |
| Compound 44 | 73 |
| Compound 45 | 72 |
| Compound 46 | 72 |
| Compound 47 | 85 |
| Compound 57 | 69 |
| Compound 69 | 59 |
| Compound 72 | 60 |
| Compound 73 | 88 |
| Compound 74 | 50 |
| Compound 79 | 53 |
| Compound 82 | 61 |
| Compound 87 | 43 |
| Compound 89 | 46 |
| Compound 93 | 43 |
| Compound 100 | 35 |
| Compound 104 | 50.6 |
| Compound 107 | 52.3 |
| Compound 108 | 51.2 |
| Compound 110 | 58 |

We claim:

1. A compound of the formula

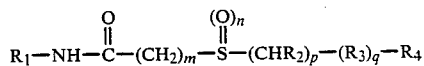

in which $R_1$ represents

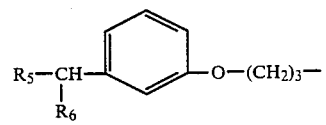

wherein $R_5$ represents piperidino, 2 methylpiperidino, 3-methylpiperidino, 4-methylpiperidino, dimethylamino, 1-pyrrolidinyl or 1-perhydro-azepinyl and $R_6$ represents hydrogen or methyl, m represents an integer from 1 to 5 inclusive, n represents zero or an integer from 1 to 2 inclusive, R₂ represents hydrogen, alkyl having 1 to 3 carbon atoms or phenyl, p represents zero or one, R₃ represents a saturated or unsaturated chain hydrocarbon residue having 1 to 4 carbon atoms, q represents zero or one, R₄ represents a phenyl group or a phenyl group substituted with an alkyl group or alkoxy group having 1 to 3 carbon atoms, a methoxy carbonyl group, a carboxyl group, a cyano group, a halogen atom, a benzothiazolyl group, nitro, two of said alkoxy groups, acetoxy, hydroxyl, methylenedioxy, acetamide, or trifluoromethyl, a pyridyl group or a pyridyl group substituted which may have 1 or 2 substituents which may be alkyl having 1 to 3 carbon atoms, halogen atoms, cyano groups, alkoxy groups having 1 to 3 carbon atoms, aminoalkyl in which the alkyl moiety has 1 or 2 carbon atoms and the amino moiety is a secondary amino group, nitro, carbomethoxy, carboxyl or acetoxy, a furyl group or a furyl group substituted by cyano, methoxycarbonyl, carboxyl, methyl, piperidino methyl or dimethylamino methyl, a thienyl group or a substituted thienyl group which may have an alkyl group having 1 to 3 carbon atoms, a halogen atom, a methoxy carbonyl group, an ethoxy carbonyl group or an amide group or a pharmaceutically acceptable acid addition salt of any of the above compounds.

2. An alkylamide derivative as claimed in claim 1 in which

R₁ represents

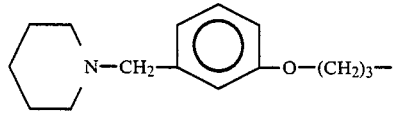

m represents 1 n represents 0, 1 or 2

R₂ represents hydrogen atom or an alkyl group of which number of carbon atom is 1 to 3 p represents 1 q represents 0

R₄ represents methoxycarbonylfuryl group, carboxylfuryl group, methylfuryl group, cyanofuryl group, piperidinomethylfuryl group, dimethylaminomethylfuryl group, or a or a salt thereof.

3. An alkylamide derivative as claimed in claim 1 in which

R₁ represents

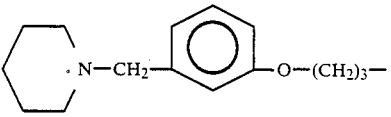

m represents 1 n represents 0

R₂ represents hydrogen atom p represents 1 q represents 0

R₄ represents a substituted pyridyl group of one or two hydrogen atoms are substituted with alkyl group(s) of which number of carbon atom is 1 to 3, haogen atom(s), cyano group(s), alkoxyl group(s), aminoalkyl group(s), nitro group(s), carbomethoxy group(s), carboxyl group(s) or acetoxy group(s), or a salt thereof.

4. An aalkyl amide derivative as claimed in claim 1 in which

R₁ represents

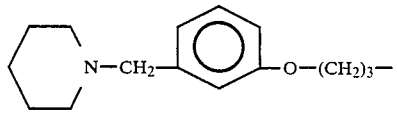

n represents 0

R₂ represents hydrogen atom p represents 1 q represents 0

R₄ represents a substituted thienyl group of which one hydrogen atom is substituted with an alkyl group of which number of carbon atom is 1 to 3, a halogen atom, methoxycarbonyl group, ethoxycarbonyl group or an amide group of which number of carbon atom is 1 or 2, or a salt therof.

5. A compound having the formula

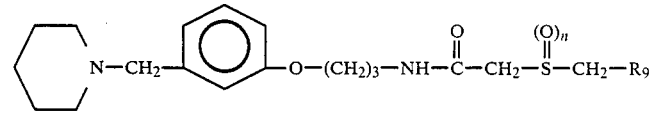

wherein n is an integer of 0, 1 or 2, and R₉ is selected from the group consisting of phenyl, furyl, pyridyl and thienyl.

6. A compound as claimed in claim 5 in which n is 1 and R₉ is 2-furyl or 3-furyl.

7. A compound as claimed in claim 5 in which n is 2 and R₉ is 2-furyl or 3-furyl.

8. A compound as claimed in claim 5 having the formula

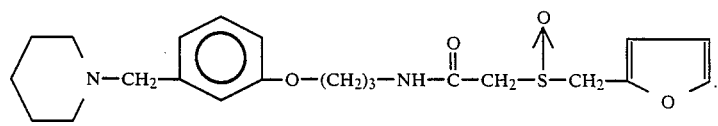

9. A compound as claimed in claim 5 having the formula

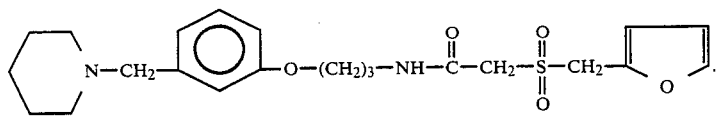
10. A compound as claimed in claim 5 having the formula
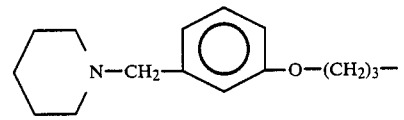
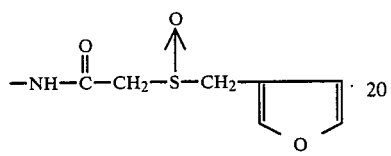
11. A compound as claimed in claim 5 having the formula
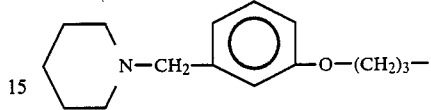
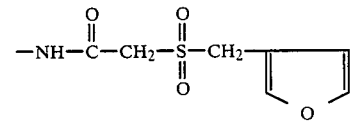
* * * * *

UNITED STATES PATENT AND TRADEMARK OFFICE
CERTIFICATE OF CORRECTION

PATENT NO. : 4 837 316

DATED : June 6, 1989

INVENTOR(S) : Yasuo SEKINE et al

It is certified that error appears in the above-identified patent and that said Letters Patent is hereby corrected as shown below:

Column 98, line 30; insert ---m represents 1---.

Signed and Sealed this

Third Day of April, 1990

*Attest:*

HARRY F. MANBECK, JR.

*Attesting Officer*      *Commissioner of Patents and Trademarks*